US008779088B2

(12) United States Patent
Kirsebom et al.

(10) Patent No.: US 8,779,088 B2

(45) Date of Patent: Jul. 15, 2014

(54) VACCINE FOR THE TREATMENT OF *MYCOBACTERIUM* RELATED DISORDERS

(75) Inventors: Leif Kirsebom, Uppsala (SE); Santanu Dasgupta, Uppsala (SE); Pontus Larsson, Uppsala (SE); Jaydip Ghosh, Bordeaux Cedex (FR)

(73) Assignee: Marfl AB, Uppsala (SE)

( * ) Notice: Subject to any disclaimer, the term of this patent is extended or adjusted under 35 U.S.C. 154(b) by 283 days.

(21) Appl. No.: 12/808,982

(22) PCT Filed: Dec. 17, 2008

(86) PCT No.: PCT/SE2008/051486

§ 371 (c)(1), (2), (4) Date: Jan. 19, 2011

(87) PCT Pub. No.: WO2009/078799

PCT Pub. Date: Jun. 25, 2009

(65) Prior Publication Data

US 2011/0104180 A1 May 5, 2011

Related U.S. Application Data

(60) Provisional application No. 61/007,893, filed on Dec. 17, 2007.

(30) Foreign Application Priority Data

Dec. 17, 2007 (SE) ...................................... 0702802

(51) Int. Cl.

*A61K 39/04* (2006.01)
*A61K 38/00* (2006.01)
*G01N 33/53* (2006.01)

(52) U.S. Cl.

USPC .......... 530/300; 424/9.1; 424/9.2; 424/184.1; 424/185.1; 424/190.1; 424/234.1; 424/248.1; 435/4; 435/7.1; 435/7.2; 435/7.32; 530/350; 536/23.1; 536/23.7

(58) Field of Classification Search

USPC .................. 424/9.1, 9.2, 184.1, 185.1, 190.1, 424/234.1, 248.1; 435/4, 7.1, 7.2, 7.32; 530/300, 350; 536/23.1, 23.7

See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu |
| 4,670,417 | A | 6/1987 | Iwasaki et al. |
| 4,791,192 | A | 12/1988 | Nakagawa et al. |
| 5,057,540 | A | 10/1991 | Kensil et al. |
| 5,208,036 | A | 5/1993 | Eppstein et al. |
| 5,264,618 | A | 11/1993 | Felgner et al. |
| 5,279,833 | A | 1/1994 | Rose |
| 5,283,185 | A | 2/1994 | Epand et al. |
| 5,314,813 | A | 5/1994 | Peterson et al. |
| 5,399,346 | A | 3/1995 | Anderson et al. |
| 6,133,429 | A | 10/2000 | Gonzalez et al. |
| 6,590,087 | B1 | 7/2003 | Bishai et al. |
| 6,703,199 | B1 | 3/2004 | Koide |
| 7,630,836 | B2 * | 12/2009 | Omura et al. .................. 702/19 |
| 2002/0150594 | A1 * | 10/2002 | Goldman et al. .......... 424/234.1 |
| 2003/0119018 | A1 * | 6/2003 | Omura et al. ..................... 435/6 |
| 2005/0238646 | A1 | 10/2005 | Ledbetter et al. |
| 2007/0042383 | A1 | 2/2007 | Kapur et al. |
| 2007/0118916 | A1 * | 5/2007 | Puzio et al. .................. 800/278 |
| 2007/0224217 | A1 | 9/2007 | Trucksis |

FOREIGN PATENT DOCUMENTS

| | | | |
|---|---|---|---|
| GB | 2220211 | A | 1/1990 |
| JP | 2006514551 | T | 5/2006 |
| WO | WO 9007861 | A1 | 7/1990 |
| WO | WO 9014837 | A1 | 12/1990 |
| WO | WO 9110741 | A1 | 7/1991 |
| WO | WO 9117271 | A1 | 11/1991 |
| WO | WO 9118980 | A1 | 12/1991 |
| WO | WO 9201047 | A1 | 1/1992 |
| WO | WO 9306121 | A1 | 4/1993 |
| WO | WO 9312227 | A1 | 6/1993 |
| WO | WO 9408051 | A1 | 4/1994 |
| WO | WO 9412629 | A1 | 6/1994 |
| WO | WO 9505853 | A1 | 3/1995 |
| WO | WO 9512608 | A1 | 5/1995 |
| WO | WO 9530642 | A1 | 11/1995 |
| WO | WO 9535503 | A1 | 12/1995 |
| WO | WO 9717613 | A1 | 5/1997 |
| WO | WO 9717614 | A1 | 5/1997 |
| WO | WO 9735611 | A1 | 10/1997 |
| WO | WO 03080653 | A1 | 10/2003 |
| WO | WO 03076898 | A2 | 8/2006 |
| WO | WO 2006087576 | A1 | 8/2006 |

OTHER PUBLICATIONS

Ghosh, J., et al. Sporulation in mycobacteria. Proceedings of the National Academy of Sciences, vol. 106, No. 26, pp. 10781-10786, 2009.*

Tragg, B.A., et al. Do mycobacteria produce endospores? Proceedings of the National Academy of Sciences, vol. 107, No. 2, pp. 878-881, 2010.*

Orme, I.M. Current progress in tuberculosis vaccine development. Vaccine 23:2105-2108, 2005.*

Giorno, et al., "Morphogenesis of the *Bacillus anthracis* Spore", Journal of Bacteriology, Feb. 2007, pp. 691-705, vol. 189, No. 3.

Duc, et al., "Bacterial Spores as Vaccine Vehicles", Infection and Immunity, May 2003, pp. 2810-2818, vol. 71, No. 5.

(Continued)

*Primary Examiner* — Rodney P Swartz

(74) *Attorney, Agent, or Firm* — Browdy and Neimark, PLLC

(57) ABSTRACT

The invention relates to genes and proteins involved in the sporulation of Mycobacteria and the use thereof in the technical fields of immunology and medicine. A vaccine comprising spore forming peptides, such as CotA or CotD, or antibodies thereto is used for the treatment of diseases caused by *Mycobacterium* such as leprosy and tuberculosis.

7 Claims, 10 Drawing Sheets

(56) References Cited

OTHER PUBLICATIONS

Mulder, et al., “Characterization of a *Mycobacterium tuberculosis* homologue of the *Streptomyces coelicolor* whiB gene”, Tubercle and Lung Disease, 1999, pp. 299-308, vol. 79, No. 5.
Bett, et al., “Packaging capacity and stability of human advenovirus type 5 vectors”, Journal of Virology, Oct. 1993, pp. 5911-5921, vol. 67, No. 10.
Boris-Lawrie, et al., “Recent advances in retrovirus vector technology”, Current Opinion in Genetics and Development, 1993, pp. 102-109.
Cevc, et al., “Ultrafleible vesicles,Transfersomes, have an extremley low pore penetration and transport therapeutic amounts of insulin across the intact mammalian skin”. Biochimica et Biophysica Acta, 1998, pp. 201-215.
Chakrabarty, et al., “*Bacillus anthracis* spores stimulate cytokine and chemoskine innate repsonses in human alveolar macrophages through multiple mitogenactivated protein kinase pathways”, Infection and Immunity Aug. 2006, pp. 4430-4438, vol. 74, No. 8.
Chang, et al., “Adjuvant activity of incomplete Freund’s adjuvant”, Adv Drug Deliv Rev., Jul. 6, 1998, 1 page.
Cole, et al., “Deciphering the biology of *Mycobacterium tuberculosis* from the complete genome sequence”, Nature, Nov. 1998, pp. 537-544, vol. 396.
Dubensky, et al., “Sindbis virus DNAbased expressed vectors: utility for in vitro and in vivo gene transfer”, Journal of Virology, Jan. 1996, pp. 508-519, vol. 70, No. 1.
Erlendsson, et al., “*Bacillus sbutilis* StoA is a thioldisulfide oxidoreductase important for spore cortex synthesis”, Journal of Bacteriology, Sep. 2004, pp. 6230-6238, vol. 186, No. 18.
Fleischmann, et al., “Whole-Genome Comparison of *Mycobacteria tuberculosis* Clinical and Laboratory Strains”, Journal of Bacteriology, Oct. 2002, pp. 5479-5490.
Glenn et al., “Skin immunizationmade possible by cholera toxin”, Nature, Feb. 26, 1998, 1 page, vol. 391.
Gruber, et al., “Multiple sigma subunits and the partioning of bacterial transcription space”, Annu. Rev. Microbiol, 2003, pp. 441-466.
Hanes, et al., “New advances in mircropsherebased singledose vaccines”, Advanced Drug Delivery Reviews, 1997, pp. 97-119.
Harlow, et al., “Antibodies, a Laboratory Manual”, Cold Spring Fiattior Laboratory, 1988, 8 pages.
Haydel, et al., “The *Mycobacterium tuberculosis* TrcR response regulator represses transcription of the expressed RV1057 gene”, Journal of Bacteriology, Jan. 2006, pp. 150-159, vol. 188, No. 1.
Hitchins, et al., “Interferance contrast and phase contrast microscopy of sporulation and germination in *Bacillus megaterium*”, Journal of Bacteriology, Nov. 1968, pp. 1811-1817, vol. 96, No. 5.
Holliger, et al., “Engineered antibody fragments and the rise of single domains”, Nature Biotechnology, Sep. 2005, 1 page.
Jansen, et al., :Immunotoxins: Hybrid molecultes combining high specificity and potent cytotoxixity, Immunological Rev., 1982, 1 page, vol. 92.
Kensil et al,. “Vaccine Design: The Subunit and Adjuvant Approach”, Plenum Press, 1995, 22 pages.
Lackner, et al., “Scanning electron microscopy of the neuropathology of murine cereberal malaria”, Malaria Journal, 2006, pp. 1-5.
Langer, “New Methods of Drug Delivery”, Science, Sep. 28, 1990, pp. 1527-1533.
Lister, “On Lactic fermentation and its bearing on pathology”, Trans. Pathol. Soc. of London, 1878, pp. 425-467.
Livingston, et al., “The Hepatitis B Virus-Specific CTL Responses Induced in Humans by Lipopeptide Vaccination Are Comparable to Those Elicited by Acute Viral Infection”, Journal of Immunology, 1997, pp. 1383-1392.
Maisnier, et al., “Conversion to bidirectional replication after unidirectional initiation from R1 plasmid origin integrated at oriC in *Escherichia coli*, ”Molecular Microbiology, 1998, pp. 1067-1079.
Moszer, et al., “SubtiList: a general relational databas edor the *Bacillus subtilis* genome”, Microbiology, 1995, pp. 261-268.
Ohe, et al., “Construction of a novel bovine papillomavirus vector without detectable transforming activity suitable for gene transfer”, Human Gene Therapy, 1995, pp. 325-333.
Paul, et al., “Transdermal immunization with large proteins by means of ultradeformable drug carriers”, Eur. J. Immunol. 1995, pp. 3521-3524.
Peterson, et al., “The Comprehensive Microbial Resource”, Nucleic Acids Research, 2001, pp. 123-125, vol. 29, No. 1.
Piggot, et al., “Sporulation of *Bacillus subtillis*”, Current Opinion in Microbiology, 2004, pp. 579-586.
Queen, et al., “A humanized antibody that binds to the interleukin 2 receptor”, Proc. Natl. Acad. Sci. USA, Dec. 1989, pp. 10029-10033.
Rivera, et al. “Genomic evidence for two functionally distinct gene classes”, Proc. Natl. Acad Sci. USA, May 1998, pp. 6239-6244, vol. 95.
Stoute, et al., “A preliminary evaluation of a recombinant circumsporozite protein vaccine against *Plasmodium falciparum* malaria”, The New England Journal of Medicine, Jan. 9, 1997, pp. 86-91, vol. 336, No. 2.
Wall, et al., “Detecting putative orthologs” Bioinformatics, 2003, pp. 1710-1711, vol. 19, No. 13.
Wang, et al., “Maintaining the transcription factor SpoIIID level late during sporulation causes spore defects in *Bacillus subtilis*”, Journal of Bateriology, Oct. 2007, pp. 7302-7309, vol. 189, No. 20.
Xiao, et al., “High efficiency, longterm clinical expression of cottontail rabbit papillomavirus (CRPV) DNA in rabbit skin following particlemediated DNA transfer”, Nucleic Acids Research, 1996, pp. 2620-2622, vol. 24, No. 13.
Zhou, et al., Adeno-associated Virus 2-mediated High Efficiency Gene Transfer into Immature and Mature Subsets of Hematopoietic Progenitor Cells in Human Umbilical Cord Blood, J. Exp. Med., Jun. 1994, pp. 1867-1875, vol. 179.
Ghosh et al, Sporulation in mycobacteria, PNAS, 106(26):10781-10786 (2009).
Ramakrishnan, Using *Mycobacterium marinum* and its hots to study tuberculosis, Current Science, 86(1):82-92 (2004).
Singh et al, Growth, cell division and sporulation in mycobacteria, Antonie van Leeuwenhoek 98:165-177 (2010).
Supplementary European Search Report in corresponding European application No. 08862701, dated Feb. 14, 2013.
Anna Csillag, Spore formation and ‘Dimorphism’ in the mycobacteria, J. Gen. Microbiol., 26:97-109 (1961).
Hutter et al., Molecular genetic characterisationof whiB3, a mycobacterial homologue, of as *Streptomyces* sporulation factor, Res. Microbiol., 150:295-301 (1999).
Li et al., The complete genome sequence of *Mycobacterium avium* subspecies paratuberculosis, PNAS, 102 (35):12344-12349 (2005).
Garnier et al., The complete genome sequence of *Mycobacterium bovis*, PNAS, 100(13):7877-7882 (2003).
Barrell et al., Deciphering the biology of *Mycobacterium tuberculosis* from the complete genome sequence, Nature, 393-537-544 (1998).

* cited by examiner

SEQUENCE LISTING

<160> NUMBER OF SEQ ID NOS: 41

<210> SEQ ID NO 1
<211> LENGTH: 1641
<212> TYPE: DNA
<213> ORGANISM: Mycobacterium marinum

<400> SEQUENCE: 1

```
gtgaatcgca gggcgttcct ggctcttatg gcggcaactg gcgcggccgg cgcgataaga     60
ggcgcatcgg cgccagcaca cgcgggcggt gacgagcttc gtgaccttcc cgaattctca    120
agcgcaaacg gtgttttgga tacagagttg agcgccgtca ccaatgttgt cgaactcgat    180
ggccgtcaac tgaccttgga gacgttcaac ggccagctac ccgggcccat cctgcgaatc    240
cggccgggtg acaatctgcg ggtcttgctc aagaaccgga ttgtcccggt cgggatcccc    300
accaacaacg tattcatgct gccctattgc gcctccaagt ccaacgacgc gcgttatgac    360
acccggcggg cctgtgtcca cgacctgtgg aacaagtggg agagacggca aacgctcgcg    420
caagaggatg tcgacatcaa cttgcacacc catggcctcc aagtgagccc agaagacccc    480
gcggacaacg tctttctgca gatcggcccg ctaaacgatc accaatacag ctacgacatc    540
ccaaaggatc agccggctgg cttgtattgg taccaccccc atttccacac ggcgaccgca    600
catcagggct ggaacgggct ctccggcgca atcatcgtcg agggcgacat tgacgcggtg    660
cccgagatcg ccgccatgcg tgagcgcacc atcgtgatca acgagctgtg gatcgccgat    720
gacagcggtg aggttccgtt caccgtggtg gcgcccatcg cgggcgatgt gccgttcgcc    780
tcctttccct cagtgccgtc gagcatgtac tacaccgtca acggccaact catcccagac    840
atcaccatgc aaccgggtga agcccagcgc tttcgggtgc tcaacgcgtg cccgcatcgg    900
tcgatatggc tgcacgtgga agggcattca ctcgagcaga tcggaaccga tgggacgccc    960
tacgccgccc cgcgcacgcg ccagcacatt ttcttggcct cggccaaccg ggccgagttc   1020
atcatcaaag cgggcgagcc cgggcgctac cggatctacg ccgaagccta cgaccaggga   1080
caccccggtg gcccccgccc ttatctgccg ctggccaccc tggtggtgcg cggcaaaccg   1140
accgacacac cgatgccgaa gaccctggtg gagccgccac ggatgccgaa cctgccggtg   1200
tcgcggcgcc gggttctggt gttctccggc gatatcagcg ggcggaccgg tatgggaatc   1260
cagttcctca tcgacggtaa ggagatgaat atggaccgga ttgatcagga ggtcgagggt   1320
ggcacggtcg aggagtggac gatagtcaat gaggacgtct tccagcaccc cttgcatatc   1380
cacataaacc cgttccaggt tgtcgacgtc caagggatcc cagcaggtga caccagttgg   1440
gcggcggcct acgagcccga catctggtgg gacacattcc gcctaccgcc gtacggcagg   1500
tatacgttgc ggacctactt ccgtccggac gtgaccggca agaccgtcta tcactgtcac   1560
```

-continued

```
atcctgcccc acgaagacag gggaatgatg ggcatcttgc tcgtcgatcc cccagggcag   1620

tatccgaagg gggcgccgtg a                                             1641


<210> SEQ ID NO 2
<211> LENGTH: 546
<212> TYPE: PRT
<213> ORGANISM: Mycobacterium marinum

<400> SEQUENCE: 2

Val Asn Arg Arg Ala Phe Leu Ala Leu Met Ala Ala Thr Gly Ala Ala
1               5                   10                  15

Gly Ala Ile Arg Gly Ala Ser Ala Pro Ala His Ala Gly Gly Asp Glu
            20                  25                  30

Leu Arg Asp Leu Pro Glu Phe Ser Ser Ala Asn Gly Val Leu Asp Thr
        35                  40                  45

Glu Leu Ser Ala Val Thr Asn Val Val Glu Leu Asp Gly Arg Gln Leu
    50                  55                  60

Thr Leu Glu Thr Phe Asn Gly Gln Leu Pro Gly Pro Ile Leu Arg Ile
65                  70                  75                  80

Arg Pro Gly Asp Asn Leu Arg Val Leu Leu Lys Asn Arg Ile Val Pro
                85                  90                  95

Val Gly Ile Pro Thr Asn Asn Val Phe Met Leu Pro Tyr Cys Ala Ser
            100                 105                 110

Lys Ser Asn Asp Ala Arg Tyr Asp Thr Arg Arg Ala Cys Val His Asp
        115                 120                 125

Leu Trp Asn Lys Trp Glu Arg Arg Gln Thr Leu Ala Gln Glu Asp Val
    130                 135                 140

Asp Ile Asn Leu His Thr His Gly Leu Gln Val Ser Pro Glu Asp Pro
145                 150                 155                 160

Ala Asp Asn Val Phe Leu Gln Ile Gly Pro Leu Asn Asp His Gln Tyr
                165                 170                 175

Ser Tyr Asp Ile Pro Lys Asp Gln Pro Ala Gly Leu Tyr Trp Tyr His
            180                 185                 190

Pro His Phe His Thr Ala Thr Ala His Gln Gly Trp Asn Gly Leu Ser
        195                 200                 205

Gly Ala Ile Ile Val Glu Gly Asp Ile Asp Ala Val Pro Glu Ile Ala
    210                 215                 220

Ala Met Arg Glu Arg Thr Ile Val Ile Asn Glu Leu Trp Ile Ala Asp
225                 230                 235                 240

Asp Ser Gly Glu Val Pro Phe Thr Val Val Ala Pro Ile Ala Gly Asp
                245                 250                 255

Val Pro Phe Ala Ser Phe Pro Ser Val Pro Ser Ser Met Tyr Tyr Thr
            260                 265                 270

Val Asn Gly Gln Leu Ile Pro Asp Ile Thr Met Gln Pro Gly Glu Ala
        275                 280                 285

Gln Arg Phe Arg Val Leu Asn Ala Cys Pro His Arg Ser Ile Trp Leu
    290                 295                 300

His Val Glu Gly His Ser Leu Glu Gln Ile Gly Thr Asp Gly Thr Pro
305                 310                 315                 320

Tyr Ala Ala Pro Arg Thr Arg Gln His Ile Phe Leu Ala Ser Ala Asn
                325                 330                 335

Arg Ala Glu Phe Ile Ile Lys Ala Gly Glu Pro Gly Arg Tyr Arg Ile
            340                 345                 350

Tyr Ala Glu Ala Tyr Asp Gln Gly His Pro Gly Gly Pro Arg Pro Tyr
```

-continued

```
        355                 360                 365

Leu Pro Leu Ala Thr Leu Val Val Arg Gly Lys Pro Thr Asp Thr Pro
    370                 375                 380

Met Pro Lys Thr Leu Val Glu Pro Pro Arg Met Pro Asn Leu Pro Val
385                 390                 395                 400

Ser Arg Arg Arg Val Leu Val Phe Ser Gly Asp Ile Ser Gly Arg Thr
                405                 410                 415

Gly Met Gly Ile Gln Phe Leu Ile Asp Gly Lys Glu Met Asn Met Asp
            420                 425                 430

Arg Ile Asp Gln Glu Val Glu Gly Gly Thr Val Glu Glu Trp Thr Ile
        435                 440                 445

Val Asn Glu Asp Val Phe Gln His Pro Leu His Ile His Ile Asn Pro
    450                 455                 460

Phe Gln Val Val Asp Val Gln Gly Ile Pro Ala Gly Asp Thr Ser Trp
465                 470                 475                 480

Ala Ala Ala Tyr Glu Pro Asp Ile Trp Trp Asp Thr Phe Arg Leu Pro
                485                 490                 495

Pro Tyr Gly Arg Tyr Thr Leu Arg Thr Tyr Phe Arg Pro Asp Val Thr
            500                 505                 510

Gly Lys Thr Val Tyr His Cys His Ile Leu Pro His Glu Asp Arg Gly
        515                 520                 525

Met Met Gly Ile Leu Leu Val Asp Pro Pro Gly Gln Tyr Pro Lys Gly
    530                 535                 540

Ala Pro
545


<210> SEQ ID NO 3
<211> LENGTH: 204
<212> TYPE: DNA
<213> ORGANISM: Mycobacterium marinum

<400> SEQUENCE: 3

atgtccgatg agcacaccca ccacgggccg catgcgcacg aacaccggca cggcgaggtg      60

acccacagcc acgcccacac cacccatcag cacgaacacg tcgagcacgc acacccgcac     120

tcacacgatg acgggaccga gcacacccat cagcacgtgc atgaatcggg cctggaaagc     180

gtgcacagcc acgcgcacag ctga                                            204


<210> SEQ ID NO 4
<211> LENGTH: 67
<212> TYPE: PRT
<213> ORGANISM: Mycobacterium marinum

<400> SEQUENCE: 4

Met Ser Asp Glu His Thr His His Gly Pro His Ala His Glu His Arg
1               5                   10                  15

His Gly Glu Val Thr His Ser His Ala His Thr Thr His Gln His Glu
            20                  25                  30

His Val Glu His Ala His Pro His Ser His Asp Asp Gly Thr Glu His
        35                  40                  45

Thr His Gln His Val His Glu Ser Gly Leu Glu Ser Val His Ser His
    50                  55                  60

Ala His Ser
65


<210> SEQ ID NO 5
```

<211> LENGTH: 669
<212> TYPE: DNA
<213> ORGANISM: Mycobacterium marinum

<400> SEQUENCE: 5

```
atgacagcac ccggcggctc cttcgacgag ggtgcccacg acggcgctgc ctcacccccca     60

cccggtgagc agccttccga acaacccttt tccccaccgc ccgacgcccc ctgggctgcc    120

ccggaagcgg catcaccagc cgacgactac ccagcgccgt cctatccgcc gcccgcctac    180

ccgccggagc cggtcggacc gggcggatac ccacccgact acgcgaccgg gtacccaccc    240

ccgcccggct acccaccgcc cgggtacccg ccctacggcg cagccgcggg cgagtacggg    300

ggcaccccgt accctccgcc cccgccgccc cccgcgccca tggcggcacc ttacggcgcg    360

ccgccaccca actacccgcc gccgtcctac cccggcgggt actacccgcc accggatccg    420

atggcgggtt atggaccggc gctgcccggc atgaacacca tggcgatcgt cgcgctggtg    480

tcctcgttgg tcggtgtgtt ctgctgcatc ggctcggtcg tggcgatcgt ggtcggcacc    540

atcgcaatca accagatcaa gcaaacccgc gaagatggct acggcctggc ggtggccggc    600

atcgtgatcg cggtcgcgac gctgttgatc tacctggtag tcggaatctt cagcattccc    660

tctcactag                                                            669
```

<210> SEQ ID NO 6
<211> LENGTH: 222
<212> TYPE: PRT
<213> ORGANISM: Mycobacterium marinum

<400> SEQUENCE: 6

```
Met Thr Ala Pro Gly Gly Ser Phe Asp Glu Gly Ala His Asp Gly Ala
1               5                   10                  15

Ala Ser Pro Pro Pro Gly Glu Gln Pro Ser Glu Gln Pro Phe Ser Pro
            20                  25                  30

Pro Pro Asp Ala Pro Trp Ala Ala Pro Glu Ala Ala Ser Pro Ala Asp
        35                  40                  45

Asp Tyr Pro Ala Pro Ser Tyr Pro Pro Pro Ala Tyr Pro Pro Glu Pro
    50                  55                  60

Val Gly Pro Gly Gly Tyr Pro Pro Asp Tyr Ala Thr Gly Tyr Pro Pro
65                  70                  75                  80

Pro Pro Gly Tyr Pro Pro Pro Gly Tyr Pro Pro Tyr Gly Ala Ala Ala
                85                  90                  95

Gly Glu Tyr Gly Gly Thr Pro Tyr Pro Pro Pro Pro Pro Pro Pro Ala
            100                 105                 110

Pro Met Ala Ala Pro Tyr Gly Ala Pro Pro Pro Asn Tyr Pro Pro Pro
        115                 120                 125

Ser Tyr Pro Gly Gly Tyr Tyr Pro Pro Pro Asp Pro Met Ala Gly Tyr
    130                 135                 140

Gly Pro Ala Leu Pro Gly Met Asn Thr Met Ala Ile Val Ala Leu Val
145                 150                 155                 160

Ser Ser Leu Val Gly Val Phe Cys Cys Ile Gly Ser Val Val Ala Ile
                165                 170                 175

Val Val Gly Thr Ile Ala Ile Asn Gln Ile Lys Gln Thr Arg Glu Asp
            180                 185                 190

Gly Tyr Gly Leu Ala Val Ala Gly Ile Val Ile Ala Val Ala Thr Leu
        195                 200                 205

Leu Ile Tyr Leu Val Val Gly Ile Phe Ser Ile Pro Ser His
    210                 215                 220
```

<210> SEQ ID NO 7
<211> LENGTH: 1164
<212> TYPE: DNA
<213> ORGANISM: Mycobacterium marinum

<400> SEQUENCE: 7
atgcgggtgg cgatgttgac tcgggagtac ccaccggagg tctatggcgg agctggggta 60
catgtcaccg agctggtggc tcgattacag cgcctgtgca ccgtcgacgt gcattgcatg 120
ggcgcacccc gccccgacgc gtcggcccat cagcccgatc cgcggctggc gaacgccaac 180
ccggcactgg ccacattgtc cgcggatctg gtgatagcca atgccgccga cgcagccagc 240
gtggtgcact cacatacctg gtacaccggc ctggcggggc atctggccgc cctgctctac 300
ggcattccgc acgtcttgac cgcccactcg ctcgaaccga tgcggccctg gaaaaccgag 360
cagctcggcg gcggctatca gatctcgtcc tgggtggaga agaccgccgt cctggccgcc 420
gacgcggtaa tcgcggtcag ctccggaatg cgtgatgacg tcctgcgcct gtaccccggg 480
ctggatccag ggatggtgca tgtcgtccgc aacggcatcg acaccgaagt gtggtttccg 540
gccggaccgg ttggtaccgc ttcggtgctc gccgaactcg ggtcgaccc gaaccgcccc 600 attgtggcgt tcgtcggcg gatcacccgg caaaagggcg taccgcactt gctggcagcg 660
gcacaccagt tcagcccgga cgtccagttg gtgctgtgcg cgggtgctcc cgacaccccg 720
gaaatcgcca atgaagtgca gtccgcggtg gctcaactgg ccagcactcg tagcggggtg 780
ttctggatcc gcgacatcct gcccgtgcag aagcttcgcg aaatactttc ggccgcaaca 840
gtttttgttt gcgcatcgat atacgagcca ttgggcatcg tgaacctcga agcaatggcc 900
tgcgcgaccg cggtggtggc ctccgatgtc ggcggcatcc ccgaggtggt cgccgacgga 960
atcaccggca cgctggtgca ttacgcggcc gacgaccccg ccggttatca atccaggctg 1020
gcacaggcgg taaatgcact ggtcgcggac ccagccaaag ccgaacgcta cggccaagcc 1080
ggacggcagc gttgtatcga ggaattctcc tggacacaga ttgccgagca gacgctggat 1140
atctatcgaa aagtgtgccg atag 1164

<210> SEQ ID NO 8
<211> LENGTH: 387
<212> TYPE: PRT
<213> ORGANISM: Mycobacterium marinum

<400> SEQUENCE: 8

Met Arg Val Ala Met Leu Thr Arg Glu Tyr Pro Pro Glu Val Tyr Gly
1 5 10 15

Gly Ala Gly Val His Val Thr Glu Leu Val Ala Arg Leu Gln Arg Leu
20 25 30

Cys Thr Val Asp Val His Cys Met Gly Ala Pro Arg Pro Asp Ala Ser
35 40 45

Ala His Gln Pro Asp Pro Arg Leu Ala Asn Ala Asn Pro Ala Leu Ala
50 55 60

Thr Leu Ser Ala Asp Leu Val Ile Ala Asn Ala Ala Asp Ala Ala Ser
65 70 75 80

Val Val His Ser His Thr Trp Tyr Thr Gly Leu Ala Gly His Leu Ala
85 90 95

Ala Leu Leu Tyr Gly Ile Pro His Val Leu Thr Ala His Ser Leu Glu
100 105 110

Pro Met Arg Pro Trp Lys Thr Glu Gln Leu Gly Gly Gly Tyr Gln Ile

-continued

```
        115                 120                 125

Ser Ser Trp Val Glu Lys Thr Ala Val Leu Ala Ala Asp Ala Val Ile
    130                 135                 140

Ala Val Ser Ser Gly Met Arg Asp Asp Val Leu Arg Leu Tyr Pro Gly
145                 150                 155                 160

Leu Asp Pro Gly Met Val His Val Val Arg Asn Gly Ile Asp Thr Glu
                165                 170                 175

Val Trp Phe Pro Ala Gly Pro Val Gly Thr Ala Ser Val Leu Ala Glu
            180                 185                 190

Leu Gly Val Asp Pro Asn Arg Pro Ile Val Ala Phe Val Gly Arg Ile
        195                 200                 205

Thr Arg Gln Lys Gly Val Pro His Leu Leu Ala Ala Ala His Gln Phe
    210                 215                 220

Ser Pro Asp Val Gln Leu Val Leu Cys Ala Gly Ala Pro Asp Thr Pro
225                 230                 235                 240

Glu Ile Ala Asn Glu Val Gln Ser Ala Val Ala Gln Leu Ala Ser Thr
                245                 250                 255

Arg Ser Gly Val Phe Trp Ile Arg Asp Ile Leu Pro Val Gln Lys Leu
            260                 265                 270

Arg Glu Ile Leu Ser Ala Ala Thr Val Phe Val Cys Ala Ser Ile Tyr
        275                 280                 285

Glu Pro Leu Gly Ile Val Asn Leu Glu Ala Met Ala Cys Ala Thr Ala
    290                 295                 300

Val Val Ala Ser Asp Val Gly Gly Ile Pro Glu Val Val Ala Asp Gly
305                 310                 315                 320

Ile Thr Gly Thr Leu Val His Tyr Ala Ala Asp Asp Pro Ala Gly Tyr
                325                 330                 335

Gln Ser Arg Leu Ala Gln Ala Val Asn Ala Leu Val Ala Asp Pro Ala
            340                 345                 350

Lys Ala Glu Arg Tyr Gly Gln Ala Gly Arg Gln Arg Cys Ile Glu Glu
        355                 360                 365

Phe Ser Trp Thr Gln Ile Ala Glu Gln Thr Leu Asp Ile Tyr Arg Lys
    370                 375                 380

Val Cys Arg
385


<210> SEQ ID NO 9
<211> LENGTH: 755
<212> TYPE: DNA
<213> ORGANISM: Mycobacterium marinum

<400> SEQUENCE: 9

atgagcggcc attccaagtg ggccaccacc aagcacaaga aggccgtcat cacgcccgcc      60

gcggcaagat gttcgcacgg ctgatcaaga acatcgaggt cgcggctcgc gtcggtggcg     120

gtgacccggc gggaaacccc accctctacg acgccatcca aaaggccaag aaaagctcgg     180

tgcccaacga gaacatcgag cgggcccgca agcgcggtgc cggtgaagag gccggtgggg     240

cggactggca gaccatcatg tacgagggtt acgcgcccaa cggtgtggcc gtactgatcg     300

agtgtctgac cgacaaccgc aaccgcgctg ccagcgaggt gcgggtggcg atgacgcgca     360

atggcggcgc catggctgat ccggggtcgg tgtcctacct gttttcccgc aagggcgtgg     420

tgaccctgga gaagaacggt ctgaccgaag acgacgtgct ggcggccgtg ttggaagccg     480

gcgccgagga cgtcaacgac ctcggggaca gcttcgaggt gatctccgaa ccgggtgaac     540
```

-continued

```
tggtcgcggt acgctccgcg ctgcaggatg ccggcatcga ctacgaatcg gccgaggcgg    600

gctttcagtc gtcggtgacc gtgccggtgg acgtcgacgg ggcccgcaag gttttcaagc    660

tcgtcgacgc gctggaagaa agcgacgacg ttcagaacgt gtggaccaac gtggacgtgt    720

ccgatgaggt gctggcggag ctcgacgagg agtag                               755


<210> SEQ ID NO 10
<211> LENGTH: 251
<212> TYPE: PRT
<213> ORGANISM: Mycobacterium marinum

<400> SEQUENCE: 10

Met Ser Gly His Ser Lys Trp Ala Thr Thr Lys His Lys Lys Ala Val
1               5                   10                  15

Ile Asp Ala Arg Arg Gly Lys Met Phe Ala Arg Leu Ile Lys Asn Ile
            20                  25                  30

Glu Val Ala Ala Arg Val Gly Gly Gly Asp Pro Ala Gly Asn Pro Thr
        35                  40                  45

Leu Tyr Asp Ala Ile Gln Lys Ala Lys Lys Ser Ser Val Pro Asn Glu
    50                  55                  60

Asn Ile Glu Arg Ala Arg Lys Arg Gly Ala Gly Glu Glu Ala Gly Gly
65                  70                  75                  80

Ala Asp Trp Gln Thr Ile Met Tyr Glu Gly Tyr Ala Pro Asn Gly Val
                85                  90                  95

Ala Val Leu Ile Glu Cys Leu Thr Asp Asn Arg Asn Arg Ala Ala Ser
            100                 105                 110

Glu Val Arg Val Ala Met Thr Arg Asn Gly Gly Ala Met Ala Asp Pro
        115                 120                 125

Gly Ser Val Ser Tyr Leu Phe Ser Arg Lys Gly Val Val Thr Leu Glu
    130                 135                 140

Lys Asn Gly Leu Thr Glu Asp Asp Val Leu Ala Ala Val Leu Glu Ala
145                 150                 155                 160

Gly Ala Glu Asp Val Asn Asp Leu Gly Asp Ser Phe Glu Val Ile Ser
                165                 170                 175

Glu Pro Gly Glu Leu Val Ala Val Arg Ser Ala Leu Gln Asp Ala Gly
            180                 185                 190

Ile Asp Tyr Glu Ser Ala Glu Ala Gly Phe Gln Ser Ser Val Thr Val
        195                 200                 205

Pro Val Asp Val Asp Gly Ala Arg Lys Val Phe Lys Leu Val Asp Ala
    210                 215                 220

Leu Glu Glu Ser Asp Asp Val Gln Asn Val Trp Thr Asn Val Asp Val
225                 230                 235                 240

Ser Asp Glu Val Leu Ala Glu Leu Asp Glu Glu
                245                 250


<210> SEQ ID NO 11
<211> LENGTH: 402
<212> TYPE: DNA
<213> ORGANISM: Mycobacterium marinum

<400> SEQUENCE: 11

atgctgatca ttgccctcgt tttagccctc attgggctcg ttgcgctggt gttcgcggtg     60

gtcaccagca atcagctggt ggcgtgggtg tgcatcggcg ccagtgcact gggtgtggtc    120

ttgctgatcg ttgacgccct cagggagcgt cagcaacgtg aggcggccag caaagaccag    180

gatgaggccg aacaaccagc cgatgccgac ggcgaggccg actacgtcga ataccctgac    240
```

```
gatgacgccg aggcggaacc ggccgccgaa gatgtcgagg acgccgaaga gggctccgag    300

gacaccgagg gcccagagga caccgagggc caagaggacg ccgatactgc ggaagaatcg    360

acggtgtccg ccgacgctaa gcgtgacgac agcgccgaat ag                       402


<210> SEQ ID NO 12
<211> LENGTH: 133
<212> TYPE: PRT
<213> ORGANISM: Mycobacterium marinum

<400> SEQUENCE: 12

Met Leu Ile Ile Ala Leu Val Leu Ala Leu Ile Gly Leu Val Ala Leu
1               5                   10                  15

Val Phe Ala Val Val Thr Ser Asn Gln Leu Val Ala Trp Val Cys Ile
            20                  25                  30

Gly Ala Ser Ala Leu Gly Val Val Leu Leu Ile Val Asp Ala Leu Arg
        35                  40                  45

Glu Arg Gln Gln Arg Glu Ala Ala Ser Lys Asp Gln Asp Glu Ala Glu
    50                  55                  60

Gln Pro Ala Asp Ala Asp Gly Glu Ala Asp Tyr Val Glu Tyr Pro Asp
65                  70                  75                  80

Asp Asp Ala Glu Ala Glu Pro Ala Ala Glu Asp Val Glu Asp Ala Glu
                85                  90                  95

Glu Gly Ser Glu Asp Thr Glu Gly Pro Glu Asp Thr Glu Gly Gln Glu
            100                 105                 110

Asp Ala Asp Thr Ala Glu Glu Ser Thr Val Ser Ala Asp Ala Lys Arg
        115                 120                 125

Asp Asp Ser Ala Glu
    130


<210> SEQ ID NO 13
<211> LENGTH: 669
<212> TYPE: DNA
<213> ORGANISM: Mycobacterium marinum

<400> SEQUENCE: 13

atgacagcac ccggcggctc cttcgacgag ggtgcccacg acggcgctgc ctcaccccca     60

cccggtgagc agccttccga acaacccttt tccccaccgc ccgacgcccc ctgggctgcc    120

ccggaagcgg catcaccagc cgacgactac ccagcgccgt cctatccgcc gcccgcctac    180

ccgccggagc cggtcggacc gggcggatac ccacccgact acgcgaccgg gtacccaccc    240

ccgcccggct acccaccgcc cgggtacccg ccctacggcg cagccgcggg cgagtacggg    300

ggcaccccgt accctccgcc cccgccgccc cccgcgccca tggcggcacc ttacggcgcg    360

ccgccaccca actacccgcc gccgtcctac cccggcgggt actacccgcc accggatccg    420

atggcgggtt atggaccggc gctgcccggc atgaacacca tggcgatcgt cgcgctggtg    480

tcctcgttgg tcggtgtgtt ctgctgcatc ggctcggtcg tggcgatcgt ggtcggcacc    540

atcgcaatca accagatcaa gcaaacccgc gaagatggct acggcctggc ggtggccggc    600

atcgtgatcg cggtcgcgac gctgttgatc tacctggtag tcggaatctt cagcattccc    660

tctcactag                                                            669


<210> SEQ ID NO 14
<211> LENGTH: 222
<212> TYPE: PRT
<213> ORGANISM: Mycobacterium marinum
```

<400> SEQUENCE: 14

Met Thr Ala Pro Gly Gly Ser Phe Asp Glu Gly Ala His Asp Gly Ala
1 5 10 15

Ala Ser Pro Pro Pro Gly Glu Gln Pro Ser Glu Gln Pro Phe Ser Pro
20 25 30

Pro Pro Asp Ala Pro Trp Ala Ala Pro Glu Ala Ala Ser Pro Ala Asp
35 40 45

Asp Tyr Pro Ala Pro Ser Tyr Pro Pro Pro Ala Tyr Pro Pro Glu Pro
50 55 60

Val Gly Pro Gly Gly Tyr Pro Pro Asp Tyr Ala Thr Gly Tyr Pro Pro
65 70 75 80

Pro Pro Gly Tyr Pro Pro Pro Gly Tyr Pro Pro Tyr Gly Ala Ala Ala
85 90 95

Gly Glu Tyr Gly Gly Thr Pro Tyr Pro Pro Pro Pro Pro Pro Pro Ala
100 105 110

Pro Met Ala Ala Pro Tyr Gly Ala Pro Pro Pro Asn Tyr Pro Pro Pro
115 120 125

Ser Tyr Pro Gly Gly Tyr Tyr Pro Pro Pro Asp Pro Met Ala Gly Tyr
130 135 140

Gly Pro Ala Leu Pro Gly Met Asn Thr Met Ala Ile Val Ala Leu Val
145 150 155 160

Ser Ser Leu Val Gly Val Phe Cys Cys Ile Gly Ser Val Val Ala Ile
165 170 175

Val Val Gly Thr Ile Ala Ile Asn Gln Ile Lys Gln Thr Arg Glu Asp
180 185 190

Gly Tyr Gly Leu Ala Val Ala Gly Ile Val Ile Ala Val Ala Thr Leu
195 200 205

Leu Ile Tyr Leu Val Val Gly Ile Phe Ser Ile Pro Ser His
210 215 220

<210> SEQ ID NO 15
<211> LENGTH: 606
<212> TYPE: DNA
<213> ORGANISM: Mycobacterium tuberculosis

<400> SEQUENCE: 15
ttgatcacca tgacggctcc cagcggctcc tctggcgaga gtgcgcacga cgccgcgggt 60
ggaccgcctc cggtcggtga gcggcccccc gaacagccca ttgctgacgc tccttgggcg 120
ccgccggcat cttcgccgat ggccaaccac ccgcccccgg cgtatccgcc gtccggttac 180
ccgcctgctt accagcccgg gtatccgacc ggctatccac cgccgatgcc acccgggggc 240
tatgcgccgc ccggatatcc accccccggc acttcttcag caggctacgg cgacatacca 300
tacccgccca tgcctccgcc atacggtgga tctccgggcg gctactaccc ggagccgggc 360
tacctagacg gctacggccc atcgcagccc ggcatgaaca ccatggcgct cgtctcactg 420
atctcggcgc tcgtcggtgt gctttgctgc atcggctcga tcgtgggcat cgtgttcggc 480
gcgatcgcca tcaaccagat caagcagaca cgcgaagaag gctacggcct ggcggtggcc 540
ggcattgtga ttggcatcgc gaccctgctg gtctacatga tcgcggggat cttcgctatc 600
ccttag 606

<210> SEQ ID NO 16
<211> LENGTH: 201
<212> TYPE: PRT

<213> ORGANISM: Mycobacterium tuberculosis

<400> SEQUENCE: 16

```
Leu Ile Thr Met Thr Ala Pro Ser Gly Ser Ser Gly Glu Ser Ala His
1               5                   10                  15

Asp Ala Ala Gly Gly Pro Pro Pro Val Gly Glu Arg Pro Pro Glu Gln
            20                  25                  30

Pro Ile Ala Asp Ala Pro Trp Ala Pro Pro Ala Ser Ser Pro Met Ala
        35                  40                  45

Asn His Pro Pro Pro Ala Tyr Pro Pro Ser Gly Tyr Pro Pro Ala Tyr
    50                  55                  60

Gln Pro Gly Tyr Pro Thr Gly Tyr Pro Pro Pro Met Pro Pro Gly Gly
65                  70                  75                  80

Tyr Ala Pro Pro Gly Tyr Pro Pro Pro Gly Thr Ser Ser Ala Gly Tyr
                85                  90                  95

Gly Asp Ile Pro Tyr Pro Pro Met Pro Pro Pro Tyr Gly Gly Ser Pro
            100                 105                 110

Gly Gly Tyr Tyr Pro Glu Pro Gly Tyr Leu Asp Gly Tyr Gly Pro Ser
        115                 120                 125

Gln Pro Gly Met Asn Thr Met Ala Leu Val Ser Leu Ile Ser Ala Leu
    130                 135                 140

Val Gly Val Leu Cys Cys Ile Gly Ser Ile Val Gly Ile Val Phe Gly
145                 150                 155                 160

Ala Ile Ala Ile Asn Gln Ile Lys Gln Thr Arg Glu Glu Gly Tyr Gly
                165                 170                 175

Leu Ala Val Ala Gly Ile Val Ile Gly Ile Ala Thr Leu Leu Val Tyr
            180                 185                 190

Met Ile Ala Gly Ile Phe Ala Ile Pro
        195                 200
```

<210> SEQ ID NO 17
<211> LENGTH: 597
<212> TYPE: DNA
<213> ORGANISM: Mycobacterium tuberculosis

<400> SEQUENCE: 17

```
atgacggctc ccagcggctc ctctggcgag agtgcgcacg acgccgcggg tggaccgcct      60

ccggtcggtg agcggccccc cgaacagccc attgctgacg ctccttgggc gccgccggca     120

tcttcgccga tggccaacca cccgcccccg gcgtatccgc cgtccggtta cccgcctgct     180

taccagcccg ggtatccgac cggctatcca ccgccgatgc cacccggggg ctatgcgccg     240

cccggatatc cacccccgg cacttcttca gcaggctacg gcgacatacc atacccgccc     300

atgcctccgc catacggtgg atctccgggc ggctactacc cggagccggg ctacctagac     360

ggctacggcc catcgcagcc cggcatgaac accatggcgc tcgtctcact gatctcggcg     420

ctcgtcggtg tgctttgctg catcggctcg atcgtgggca tcgtgttcgg cgcgatcgcc     480

atcaaccaga tcaagcagac acgcgaagaa ggctacggcc tggcggtggc cggcattgtg     540

attggcatcg cgaccctgct ggtctacatg atcgcgggga tcttcgctat cccttag       597
```

<210> SEQ ID NO 18
<211> LENGTH: 198
<212> TYPE: PRT
<213> ORGANISM: Mycobacterium tuberculosis

<400> SEQUENCE: 18

-continued

```
Met Thr Ala Pro Ser Gly Ser Ser Gly Glu Ser Ala His Asp Ala Ala
1               5                   10                  15

Gly Gly Pro Pro Pro Val Gly Glu Arg Pro Pro Glu Gln Pro Ile Ala
            20                  25                  30

Asp Ala Pro Trp Ala Pro Pro Ala Ser Ser Pro Met Ala Asn His Pro
        35                  40                  45

Pro Pro Ala Tyr Pro Pro Ser Gly Tyr Pro Pro Ala Tyr Gln Pro Gly
    50                  55                  60

Tyr Pro Thr Gly Tyr Pro Pro Pro Met Pro Pro Gly Gly Tyr Ala Pro
65                  70                  75                  80

Pro Gly Tyr Pro Pro Pro Gly Thr Ser Ser Ala Gly Tyr Gly Asp Ile
                85                  90                  95

Pro Tyr Pro Pro Met Pro Pro Pro Tyr Gly Gly Ser Pro Gly Gly Tyr
            100                 105                 110

Tyr Pro Glu Pro Gly Tyr Leu Asp Gly Tyr Gly Pro Ser Gln Pro Gly
        115                 120                 125

Met Asn Thr Met Ala Leu Val Ser Leu Ile Ser Ala Leu Val Gly Val
    130                 135                 140

Leu Cys Cys Ile Gly Ser Ile Val Gly Ile Val Phe Gly Ala Ile Ala
145                 150                 155                 160

Ile Asn Gln Ile Lys Gln Thr Arg Glu Glu Gly Tyr Gly Leu Ala Val
                165                 170                 175

Ala Gly Ile Val Ile Gly Ile Ala Thr Leu Leu Val Tyr Met Ile Ala
            180                 185                 190

Gly Ile Phe Ala Ile Pro
        195


<210> SEQ ID NO 19
<211> LENGTH: 597
<212> TYPE: DNA
<213> ORGANISM: Mycobacterium bovis

<400> SEQUENCE: 19

atgacggctc ccagcggctc ctctggcgag agtgcgcacg acgccgcggg tggaccgcct      60

ccggtcggtg agcggccccc cgaacagccc attgctgacg ctccttgggc gccgccggca     120

tcttcgccga tggccgacca cccgcccccg gcgtatccgc cgtccggtta cccgcctgct     180

taccagcccg ggtatccgac cgactatcca ccgccgatgc cacccggggg ctatgcgccg     240

cccggatatc cacccccggg cacttcttca gcaggctacg gcgacatacc atacccgccc     300

atgcctccgc catacggtgg atctccgggc ggctactacc cggagccggg ctacctagac     360

ggctacggcc catcgcagcc cggcatgaac accatggcgc tcgtctcact gatctcggcg     420

ctcgtcggtg tgctttgctg catcggctcg atcgtgggca tcgtgttcgg cgcgatcgcc     480

atcaaccaga tcaagcagac acgcgaagaa ggctacggcc tggcggtggc cggcattgtg     540

attggcatcg cgaccctgct ggtctacatg atcgcgggga tcttcgctat cccttag        597


<210> SEQ ID NO 20
<211> LENGTH: 198
<212> TYPE: PRT
<213> ORGANISM: Mycobacterium bovis

<400> SEQUENCE: 20

Met Thr Ala Pro Ser Gly Ser Ser Gly Glu Ser Ala His Asp Ala Ala
1               5                   10                  15

Gly Gly Pro Pro Pro Val Gly Glu Arg Pro Pro Glu Gln Pro Ile Ala
```

```
            20                  25                  30

Asp Ala Pro Trp Ala Pro Pro Ala Ser Ser Pro Met Ala Asp His Pro
        35                  40                  45

Pro Pro Ala Tyr Pro Pro Ser Gly Tyr Pro Pro Ala Tyr Gln Pro Gly
    50                  55                  60

Tyr Pro Thr Asp Tyr Pro Pro Pro Met Pro Pro Gly Gly Tyr Ala Pro
65                  70                  75                  80

Pro Gly Tyr Pro Pro Pro Gly Thr Ser Ser Ala Gly Tyr Gly Asp Ile
                85                  90                  95

Pro Tyr Pro Pro Met Pro Pro Pro Tyr Gly Gly Ser Pro Gly Gly Tyr
            100                 105                 110

Tyr Pro Glu Pro Gly Tyr Leu Asp Gly Tyr Gly Pro Ser Gln Pro Gly
        115                 120                 125

Met Asn Thr Met Ala Leu Val Ser Leu Ile Ser Ala Leu Val Gly Val
    130                 135                 140

Leu Cys Cys Ile Gly Ser Ile Val Gly Ile Val Phe Gly Ala Ile Ala
145                 150                 155                 160

Ile Asn Gln Ile Lys Gln Thr Arg Glu Glu Gly Tyr Gly Leu Ala Val
                165                 170                 175

Ala Gly Ile Val Ile Gly Ile Ala Thr Leu Leu Val Tyr Met Ile Ala
            180                 185                 190

Gly Ile Phe Ala Ile Pro
        195
```

<210> SEQ ID NO 21
<211> LENGTH: 615
<212> TYPE: DNA
<213> ORGANISM: Mycobacterium leprae

<400> SEQUENCE: 21

```
atgacagctc ccggcgacgc cttcggcgag agtgcccacg aagatgaggc gaacccgcca     60

gccgttacga ggcccccaag acagccggtt tggggtggcc cctggcatcc gaccgcacca    120

ccgcacgcag ccgatcacac gcacgcgaca tatccgctac ctgatgttcc tccaggctat    180

ccgtcggacc ttccgaccga ctatccagaa cccatagcgc ccaccccacc gggatacgga    240

caaccgctaa gctatggtgg gccgccctac ccaccgccgc aatttggcac acctgcaact    300

ggccatggtc ctgggtcact ttggcatccg ggtgaatatc caggcaacta tccgggggc     360

tactatccgc cgaattacct ggggggttac ggagcaacac agccaggaat gaacgtgatg    420

gcgatcgcct cgctaatatc ctcgttcgcc gggttggtgt gctgcatagg ctcgatcctg    480

gccatcgtgc tcggcgccat cgccctcgag cagaccaagc ggactcgcca agaaggctac    540

ggcctagccg ttgccggcat agtgatcggg atcgcgaccc tgctggtgag tttgaccgtc    600

gcagtattcg cgctg                                                     615
```

<210> SEQ ID NO 22
<211> LENGTH: 205
<212> TYPE: PRT
<213> ORGANISM: Mycobacterium leprae

<400> SEQUENCE: 22

```
Met Thr Ala Pro Gly Asp Ala Phe Gly Glu Ser Ala His Glu Asp Glu
1               5                   10                  15

Ala Asn Pro Pro Ala Val Thr Arg Pro Pro Arg Gln Pro Val Trp Gly
            20                  25                  30
```

```
Gly Pro Trp His Pro Thr Ala Pro Pro His Ala Ala Asp His Thr His
        35                  40                  45

Ala Thr Tyr Pro Leu Pro Asp Val Pro Pro Gly Tyr Pro Ser Asp Leu
    50                  55                  60

Pro Thr Asp Tyr Pro Glu Pro Ile Ala Pro Thr Pro Pro Gly Tyr Gly
65                  70                  75                  80

Gln Pro Leu Ser Tyr Gly Gly Pro Pro Tyr Pro Pro Pro Gln Phe Gly
                85                  90                  95

Thr Pro Ala Thr Gly His Gly Pro Gly Ser Leu Trp His Pro Gly Glu
            100                 105                 110

Tyr Pro Gly Asn Tyr Pro Gly Gly Tyr Tyr Pro Pro Asn Tyr Leu Gly
        115                 120                 125

Gly Tyr Gly Ala Thr Gln Pro Gly Met Asn Val Met Ala Ile Ala Ser
    130                 135                 140

Leu Ile Ser Ser Phe Ala Gly Leu Val Cys Cys Ile Gly Ser Ile Leu
145                 150                 155                 160

Ala Ile Val Leu Gly Ala Ile Ala Leu Glu Gln Thr Lys Arg Thr Arg
                165                 170                 175

Gln Glu Gly Tyr Gly Leu Ala Val Ala Gly Ile Val Ile Gly Ile Ala
            180                 185                 190

Thr Leu Leu Val Ser Leu Thr Val Ala Val Phe Ala Leu
        195                 200                 205


<210> SEQ ID NO 23
<211> LENGTH: 753
<212> TYPE: DNA
<213> ORGANISM: Mycobacterium avium

<400> SEQUENCE: 23

atgagcggcc attccaagtg ggccaccacc aagcacaaga aggccgtcat cgacgcccgc      60

cgcggcaaga tgttcgcccg gctgatcaag aacatcgagg tcgcggcccg cgtcggtggc     120

ggtgatccgg cgggcaaccc gacgctctac gacgcgatcc agaaggcgaa gaagagctcg     180

gtgcccaacg agaacatcga gcgggcgcgc aagcgcggcg ccggcgagga ggccggcggc     240

gccgactggc agaccatcac ctacgagggg tatgcgccca acggcgtggc ggtgctgatc     300

gagtgcctga ccgacaaccg caaccgcgcc gccagcgagg tgcgggtggc gatgactcgc     360

aacggcggca ccatggccga tccgggttcg gtgtcctacc tgttctcccg caagagcgtc     420

gtcacctgtg agaagaacgg cctgaccgag gacgacatcc tggcggccgt gctggatgcc     480

ggcgccgaag aggtcgagga cctcggcgac agcttcgaaa tcatctgcga gccaaccgat     540

ctcgtcgcgg tgcggacggc gctgcaggac gcgggcatcg actacgactc cgccgaggcg     600

ggattccagc cgtcggtgac ggtgccgctg aacgccgacg gcgcgcagaa ggtgatgcgg     660

ctggtcgacg cgctcgagga cagcgacgac gtccaggacg tgtggaccaa cgccgacatt     720

cccgacgaga tcctggccca gatcgaggag tga                                  753


<210> SEQ ID NO 24
<211> LENGTH: 250
<212> TYPE: PRT
<213> ORGANISM: Mycobacterium avium

<400> SEQUENCE: 24

Met Ser Gly His Ser Lys Trp Ala Thr Thr Lys His Lys Lys Ala Val
1               5                   10                  15

Ile Asp Ala Arg Arg Gly Lys Met Phe Ala Arg Leu Ile Lys Asn Ile
```

-continued

```
            20                  25                  30

Glu Val Ala Ala Arg Val Gly Gly Gly Asp Pro Ala Gly Asn Pro Thr
        35                  40                  45

Leu Tyr Asp Ala Ile Gln Lys Ala Lys Lys Ser Ser Val Pro Asn Glu
    50                  55                  60

Asn Ile Glu Arg Ala Arg Lys Arg Gly Ala Gly Glu Glu Ala Gly Gly
65                  70                  75                  80

Ala Asp Trp Gln Thr Ile Thr Tyr Glu Gly Tyr Ala Pro Asn Gly Val
                85                  90                  95

Ala Val Leu Ile Glu Cys Leu Thr Asp Asn Arg Asn Arg Ala Ala Ser
            100                 105                 110

Glu Val Arg Val Ala Met Thr Arg Asn Gly Gly Thr Met Ala Asp Pro
        115                 120                 125

Gly Ser Val Ser Tyr Leu Phe Ser Arg Lys Ser Val Val Thr Cys Glu
    130                 135                 140

Lys Asn Gly Leu Thr Glu Asp Asp Ile Leu Ala Ala Val Leu Asp Ala
145                 150                 155                 160

Gly Ala Glu Glu Val Glu Asp Leu Gly Asp Ser Phe Glu Ile Ile Cys
                165                 170                 175

Glu Pro Thr Asp Leu Val Ala Val Arg Thr Ala Leu Gln Asp Ala Gly
            180                 185                 190

Ile Asp Tyr Asp Ser Ala Glu Ala Gly Phe Gln Pro Ser Val Thr Val
        195                 200                 205

Pro Leu Asn Ala Asp Gly Ala Gln Lys Val Met Arg Leu Val Asp Ala
    210                 215                 220

Leu Glu Asp Ser Asp Asp Val Gln Asp Val Trp Thr Asn Ala Asp Ile
225                 230                 235                 240

Pro Asp Glu Ile Leu Ala Gln Ile Glu Glu
                245                 250
```

<210> SEQ ID NO 25
<211> LENGTH: 753
<212> TYPE: DNA
<213> ORGANISM: Mycobacterium avium

<400> SEQUENCE: 25

```
tcactcctcg atctgggcca ggatctcgtc gggaatgtcg gcgttggtcc acacgtcctg      60

gacgtcgtcg ctgtcctcga gcgcgtcgac cagccgcatc accttctgcg cgccgtcggc     120

gtccagcggc accgtcaccg acggctggaa tcccgcctcg gcggagtcgt agtcgatgcc     180

ggcgtcctgc agcgccgtcc gcaccgcgac gagatcggtt ggctcgcaga tgatttcgaa     240

gctgtcgccg aggtcctcga cctcttcggc gccggcgtcc agcacggccg ccaggatgtc     300

gtcctcggtc aggccgttct tctcacaggt gacgacgccc ttgcgggaga acaggtagga     360

caccgaaccc gggtcggcca tggtgccgcc gttgcgggtc atcgccaccc gcacctcgct     420

ggcggcgcgg ttgcggttgt cggtcaggca ctcgatcagc accgccacgc cgttgggcgc     480

ataccccctcg taggtgatgg tctgccagtc ggcgccgccg gcctcctcgc cggcgccgcg     540

tttgcgggcc cgctcgatgt tctcgttggg caccgagctc ttcttcgcct tctggatcgc     600

gtcgtagagc gtcgggttgc ccgccggatc accgccaccg acgcgggccg cgacctcgat     660

gttcttgatc agccgggcga acatcttgcc gcggcgggcg tcgatgacgg ccttcttgtg     720

cttggtggtg gcccacttgg aatggccgct cat                                  753
```

<210> SEQ ID NO 26
<211> LENGTH: 250
<212> TYPE: PRT
<213> ORGANISM: Mycobacterium avium

<400> SEQUENCE: 26

```
Met Ser Gly His Ser Lys Trp Ala Thr Thr Lys His Lys Lys Ala Val
1               5                   10                  15

Ile Asp Ala Arg Arg Gly Lys Met Phe Ala Arg Leu Ile Lys Asn Ile
            20                  25                  30

Glu Val Ala Ala Arg Val Gly Gly Gly Asp Pro Ala Gly Asn Pro Thr
        35                  40                  45

Leu Tyr Asp Ala Ile Gln Lys Ala Lys Lys Ser Ser Val Pro Asn Glu
    50                  55                  60

Asn Ile Glu Arg Ala Arg Lys Arg Gly Ala Gly Glu Glu Ala Gly Gly
65                  70                  75                  80

Ala Asp Trp Gln Thr Ile Thr Tyr Glu Gly Tyr Ala Pro Asn Gly Val
                85                  90                  95

Ala Val Leu Ile Glu Cys Leu Thr Asp Asn Arg Asn Arg Ala Ala Ser
            100                 105                 110

Glu Val Arg Val Ala Met Thr Arg Asn Gly Gly Thr Met Ala Asp Pro
        115                 120                 125

Gly Ser Val Ser Tyr Leu Phe Ser Arg Lys Gly Val Val Thr Cys Glu
    130                 135                 140

Lys Asn Gly Leu Thr Glu Asp Asp Ile Leu Ala Ala Val Leu Asp Ala
145                 150                 155                 160

Gly Ala Glu Glu Val Glu Asp Leu Gly Asp Ser Phe Glu Ile Ile Cys
                165                 170                 175

Glu Pro Thr Asp Leu Val Ala Val Arg Thr Ala Leu Gln Asp Ala Gly
            180                 185                 190

Ile Asp Tyr Asp Ser Ala Glu Ala Gly Phe Gln Pro Ser Val Thr Val
        195                 200                 205

Pro Leu Asp Ala Asp Gly Ala Gln Lys Val Met Arg Leu Val Asp Ala
    210                 215                 220

Leu Glu Asp Ser Asp Asp Val Gln Asp Val Trp Thr Asn Ala Asp Ile
225                 230                 235                 240

Pro Asp Glu Ile Leu Ala Gln Ile Glu Glu
                245                 250
```

<210> SEQ ID NO 27
<211> LENGTH: 228
<212> TYPE: DNA
<213> ORGANISM: Artificial Sequence
<220> FEATURE:
<223> OTHER INFORMATION: synthetic

<400> SEQUENCE: 27

```
gagcagggtg attgctaaca gcaatccgag gtgactcgcg ggaaagtgcc acacagaaaa      60

cagaccgcca ctctcgcggt ggtaagggtg aacggtgcgg taagagcgca ccagcacccc     120

gggtgaccgg ggtggctagg caaaccccac ccgaagcaag gtcaagaagg ccgtaccgta     180

ggtgcggccg cgcaggcgtt tgagggctgc tcgcccgagt ctgcgggt                  228
```

<210> SEQ ID NO 28
<211> LENGTH: 226
<212> TYPE: DNA
<213> ORGANISM: Artificial Sequence
<220> FEATURE:

-continued

<223> OTHER INFORMATION: synthetic

<400> SEQUENCE: 28
gagcgggtga ttgctaacag caatccgagg tgactcgcgg gaaagtgcca cacagaaaac 60
agaccgccac ctcgcggtgg taagggtgaa cggtgcggta agagcgcacc agcaccccgg 120
gtgaccgggg tggctaggca aaccccaccc gaagcaaggt caagaaggcc gtaccgtagg 180
tgcggccgcg caggcgtttg agggctgctc gcccgagtct gcgggt 226

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
atcgaggaaa gtccggactt caca 24

<210> SEQ ID NO 30
<211> LENGTH: 22
<212> TYPE: DNA
<213> ORGANISM: Artificial Sequence
<220> FEATURE:
<223> OTHER INFORMATION: synthetic

<400> SEQUENCE: 30
acccgcagac tcgggcgagc ag 22

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
gctgacaggc ttagcttccg 20

<210> SEQ ID NO 32
<211> LENGTH: 21
<212> TYPE: DNA
<213> ORGANISM: Artificial Sequence
<220> FEATURE:
<223> OTHER INFORMATION: synthetic

<400> SEQUENCE: 32
agtcgttctt ggcgccggtt g 21

<210> SEQ ID NO 33
<211> LENGTH: 19
<212> TYPE: DNA
<213> ORGANISM: Artificial Sequence
<220> FEATURE:
<223> OTHER INFORMATION: synthetic

<400> SEQUENCE: 33
ggaaccttga ccgaccaac 19

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
agttggtgca cgcctcgctg 20

<210> SEQ ID NO 35
<211> LENGTH: 19
<212> TYPE: DNA
<213> ORGANISM: Artificial Sequence
<220> FEATURE:
<223> OTHER INFORMATION: synthetic

<400> SEQUENCE: 35
gtgtgtatgc gtcagagtc 19

<210> SEQ ID NO 36
<211> LENGTH: 20
<212> TYPE: DNA
<213> ORGANISM: Artificial Sequence
<220> FEATURE:
<223> OTHER INFORMATION: synthetic

<400> SEQUENCE: 36
acgagtgctg gccagttgag 20

<210> SEQ ID NO 37
<211> LENGTH: 19
<212> TYPE: DNA
<213> ORGANISM: Artificial Sequence
<220> FEATURE:
<223> OTHER INFORMATION: synthetic

<400> SEQUENCE: 37
cagtacggcc acaccgttg 19

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
gcaaatgagc tcatgaaaac 20

<210> SEQ ID NO 39
<211> LENGTH: 21
<212> TYPE: DNA
<213> ORGANISM: Artificial Sequence
<220> FEATURE:
<223> OTHER INFORMATION: synthetic

<400> SEQUENCE: 39
agcgttgcgc aagcgattct c 21

<210> SEQ ID NO 40
<211> LENGTH: 20
<212> TYPE: DNA
<213> ORGANISM: Artificial Sequence
<220> FEATURE:
<223> OTHER INFORMATION: synthetic

<400> SEQUENCE: 40
gttgacgaag ctggactttc 20

<210> SEQ ID NO 41

-continued

```
<211> LENGTH: 19
<212> TYPE: DNA
<213> ORGANISM: Artificial Sequence
<220> FEATURE:
<223> OTHER INFORMATION: synthetic

<400> SEQUENCE: 41

aggcttgcct tcctggatg                                         19
```

VACCINE FOR THE TREATMENT OF *MYCOBACTERIUM* RELATED DISORDERS

CROSS-REFERENCE TO RELATED APPLICATIONS

This application is a 371 National Stage of International application no. PCT/SE2008/051486, filed Dec. 17, 2008, which claims priority from Swedish application no. 0702802-0, filed Dec. 17, 2007.

TECHNICAL FIELD

The invention relates to genes involved in the sporulation of Mycobacteria in the technical fields of immunology and medicine.

BACKGROUND

The genus *Mycobacterium* includes highly successful pathogens e.g. *Mycobacterium tuberculosis* and *Mycobacterium leprae*, the etiological agents of tuberculosis and leprosy, respectively. The *M. tuberculosis* (Mtb) is one of the most successful human pathogens and estimations suggest that one third of the human population carry this bacteria. Other *Mycobacterium* species worth mentioning are *Mycobacterium marinum* (Mm), *Mycobacterium avium* and *Mycobacterium ulcerans.*

Today approximately eight million people per year develop active disease and two million die. Pathogenic mycobacteria have the ability to persist for a long time in the host without causing any symptoms. This latency poses an additional hidden threat to human health but is not clearly understood. Mycobacteria can colonize their hosts without the hosts showing any adverse signs. For example, billions of people around the world are infected with *M. tuberculosis* but will never know it because they will not develop symptoms.

Mycobacterial infections are notoriously difficult to treat. The organisms are hardy due to their cell wall, which is neither truly Gram negative nor positive, and unique to the family, they are naturally resistant to a number of antibiotics that work by destroying cell walls, such as penicillin. Most mycobacteria are susceptible to antibiotics e.g. clarithromycin, isoniazid and rifamycin, but antibiotic-resistant strains are known to exist, and the emergence of multi resistant strains is an increasing problem.

An attenuated strain of *Mycobacterium bovis* is currently the most widely used and safest attenuated human vaccine, but controversy concerning its efficacy has emerged.

Consequently, there is a need for improved methods and medicaments to prevent and treat diseases which are caused by Mycobacteria.

SUMMARY OF THE INVENTION

It has now, for the first time, been shown that Mycobacteria have the ability to form spores. This is contrary to text book descriptions of mycobacteria as non-sporulating, gram-positive species. This introduces a new perspective into the life style of pathogenic mycobacteria and its potential for spreading, as well as persistence, of mycobacterial infections. Consequently, the present invention is directed to methods and compounds which are useful to treat and/or prevent diseases which are caused by Mycobacteria, such as tuberculosis. In particular, the invention relates to the treatment and/or prevention of such diseases wherein the Mycobacteria are, or will be, sporulating. Such methods and compounds may be based on active or passive immunization, wherein active immunization is performed by administering a vaccine, and passive immunization is performed by administering an antibody.

In one aspect, the invention provides methods of preventing or treating a disease which is caused by Mycobacteria. Such diseases are e.g. tuberculosis, leprosy and diseases caused by non-tuberculous Mycobacteria (NTM). Also included is Crohns disease and the livestock disease Johne's disease. It is well known that individuals with an impaired immune system, such as AIDS patients, and patients who receive immunosuppressing treatments are sensitive to Mycobacterial infections. Such patients may benefit from treatment according to this invention.

The invention also provides compounds which may be useful for treating the above mentioned diseases, either in the form of vaccines, or in the form of antibodies. Also contemplated are binding molecules other than antibodies.

Methods for treating such diseases entail inducing an immune response against a peptide component from one of the gene products involved in sporulation, in the patient. Such induction can be active by administration of an immunogen (such as a vaccine), or passive by administration of an antibody or an active fragment or derivative of the antibody. In some methods, the patient is asymptomatic. In some methods, treatment is prophylactic.

For treatment of patients suffering from a disease caused by Mycobacteria, one treatment regime entails administering a dose of a peptide derived from a protein component in the spore coating to the patient to induce the immune response. In some methods, the spore coating peptide is administered with an adjuvant that enhances the immune response to the spore coating peptide. Examples of adjuvants are alum and MPL. The dose of spore coating peptide administered to the patient is typically at least 1 or 10 μg, if administered with adjuvant, and at least 50 μg if administered without adjuvant. In some methods, the dose is at least 100 μg.

In some methods, the spore coating peptide is a fragment of the gene products shown in tables 1-4.

In some methods, the therapeutic agent is an effective dose of a nucleic acid encoding a spore coating peptide or an active fragment or derivative thereof. The nucleic acid encoding spore coating or a fragment thereof is expressed in the patient to produce a spore coating peptide or the active fragment thereof, which induces the immune response. In some such methods, the nucleic acid is administered through the skin, optionally via a patch. In some methods, a therapeutic agent is identified by screening a library of compounds to identify a compound reactive with antibodies to the spore coating peptide, and administering the compound to the patient to induce the immune response.

In some methods, the immune response comprises T-cells that bind to spore coating peptide complexed with MHC1 or MHCII on CD8 or CD4 cells. In other methods, the immune response is induced by administering an antibody to the spore coating peptide to the patient. In some methods, the immune response is induced by removing T-cells from the patient, contacting the T-cells with spore coating peptide under conditions in which the T-cells are primed, and replacing the T-cells in the patient.

The invention also encompasses molecules other than antibodies which are capable of binding to the spore coating peptides. Collectively, the molecules, e.g. antibodies and other molecules capable of binding to the spore coating peptides are termed "binding molecules". Binding molecules of the invention are preferably antibodies, as defined herein. The term "antibody" refers to an intact antibody, or a binding fragment thereof. An antibody may comprise a complete antibody molecule (including polyclonal, monoclonal, chimeric, humanized, or human versions having full length heavy and/or light chains), or comprise an antigen binding fragment thereof. Antibody fragments include $F(ab')_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (See e.g., Hollinger and Hudson, 2005, Nature Biotechnology, 23, 9, 1126-1136). Antibody polypeptides are also disclosed in U.S. Pat. No. 6,703,199, including fibronectin polypeptide monobodies. Other antibody polypeptides are disclosed in U.S. Patent Publication 2005/0238646, which are single-chain polypeptides.

Antigen binding fragments derived from an antibody can be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al, in Methods in Enzymology 1:422 (Academic Press 1967); and by Andrews, S. M. and Titus, J. A. in Current Protocols in Immunology (Coligan J. E., et al., eds), John Wiley & Sons, New York (2003). pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

An antibody fragment may also be any synthetic or genetically engineered protein. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker (scFv proteins).

Another form of an antibody fragment is a peptide comprising one or more complementarity determining regions (CDRs) of an antibody. CDRs (also termed "minimal recognition units", or "hypervariable region") can be obtained by constructing polynucleotides that encode the CDR of interest. Such polynucleotides may be prepared, for example, by using the polymerase chain reaction to synthesize the variable region using mRNA of antibody-producing cells as a template (see, for example, Larrick et al, Methods: A Companion to Methods in Enzymology 2:106, 1991; Courtenay-Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al, "Genetic Manipulation and Expression of Antibodies," in Monoclonal Antibodies: Principles and Applications, Birch et al, (eds.), page 137 (Wiley-Liss, Inc. 1995)).

Thus, in one embodiment, the binding molecule comprises at least one CDR as described herein. The binding molecule may comprise at least two, three, four, five or six CDR's as described herein. The binding molecule further may comprise at least one variable region domain of an antibody described herein. The variable region domain may be of any size or amino acid composition and will generally comprise at least one CDR sequence responsible for binding to a spore forming peptide, for example CDR-H1, CDR-H2, CDR-H3 and/or the light chain CDRs specifically described herein and which is adjacent to or in frame with one or more framework sequences. In general terms, the variable (V) region domain may be any suitable arrangement of immunoglobulin heavy ($V_H$) and/or light ($V_L$) chain variable domains. Thus, for example, the V region domain may be monomeric and be a $V_H$ or $V_L$ domain, which is capable of independently binding spore forming peptide with an affinity at least equal to $1\times10^{-7}$ M or less as described below. Alternatively, the V region domain may be dimeric and contain $V_H$-$V_H$, $V_H$-$V_L$, or $V_L$-$V_L$, dimers. The V region dimer comprises at least one $V_H$ and at least one $V_L$ chain that may be non-covalently associated (hereinafter referred to as $F_V$). If desired, the chains may be covalently coupled either directly, for example via a disulfide bond between the two variable domains, or through a linker, for example a peptide linker, to form a single chain Fv ($scF_V$).

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

Other binding molecules which may be used include e.g. those described in WO03/080653, camelids, affibodies, and diabodies.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

As described herein, binding molecules comprise at least one of these CDRs. For example, one or more CDR may be incorporated into known antibody framework regions (IgG1, IgG2, etc.), or conjugated to a suitable vehicle to enhance the half-life thereof. Suitable vehicles include, but are not limited to Fc, polyethylene glycol (PEG), albumin, transferrin, and the like. These and other suitable vehicles are known in the art. Such conjugated CDR peptides may be in monomeric, dimeric, tetrameric, or other form. In one embodiment, one or more water-soluble polymer may be linked to one or more specific positions, for example at the amino terminus, of a binding molecule.

In certain preferred embodiments, a binding molecule comprises one or more water soluble polymer attachments, including, but not limited to, polyethylene glycol, polyoxyethylene glycol, or polypropylene glycol. See, e.g., U.S. Pat.

Nos. 4,640,835, 4,496,689, 4,301,144, 4,670,417, 4,791,192 and 4,179,337. In certain embodiments, a derivative binding molecule comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding molecule, such as an antibody. Certain such methods are discussed, for example, in U.S. Pat. No. 6,133,426, which is hereby incorporated by reference for any purpose.

It will be appreciated that a binding molecule of the present invention may have at least one amino acid substitution, providing that the binding molecule retains binding specificity. Therefore, modifications to the binding molecule structures are encompassed within the scope of the invention. These may include amino acid substitutions, which may be conservative or non-conservative, that do not destroy the spore coating peptides capability of binding to a binding molecule. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position.

The binding molecules according to this invention may also be used as a diagnostic tool to detect the presence, or absence, of Mycobacteria in the form of spores in an animal, such as humans or livestock. Detection is preferably performed on a sample from said animal or human subject that is suspected of containing spores derived from Mycobacteria, such as body fluids, e.g. blood, serum, bronchoalveolar lavage fluid, saliva, urine, feaces, tears and the like. Also contemplated is the non-diagnostic detection of spores derived from Mycobacteria in food products, such as milk, cheese, butter, vegetables, and meat, or in products intended as animal feed. The binding agents according to the invention may also be used to detect Mycobacteria in environmental samples from environments suspected of being contaminated with spores derived from Mycobacteria, e.g. fish and bird farms. Methods for such detection are well known and include e.g. ELISA assays and other immunological assays.

The therapeutic agent, or binding molecule, can typically be administered orally, intranasally, intradermally, subcutaneously, intramuscularly, topically or intravenously. In some methods, the patient is monitored followed administration to assess the immune response. If the monitoring indicates a reduction of the immune response over time, the patient can be given one or more further doses of the agent.

In another aspect, the invention provides pharmaceutical compositions comprising a spore coating peptide and an excipient suitable for oral and other routes of administration. The invention also provides pharmaceutical compositions comprising an agent effective to induce an immunogenic response against spore coating peptide in an animal, and a pharmaceutically acceptable adjuvant. In some such compositions, the agent is spore coating peptide or an active fragment thereof. In some compositions, the adjuvant comprises alum.

In some compositions, the adjuvant comprises an oil-in-water emulsion. In some compositions, the spore coating peptide or active fragment thereof is a component of a polylactide polyglycolide copolymer (PLPG) or other particle. The invention further provides compositions comprising spore coating peptide or an active fragment linked to a conjugate molecule that promotes delivery of spore coating peptide to the bloodstream of a patient and/or promotes an immune response against spore coating peptide. For example, the conjugate can serve to promote an immune response against spore coating peptide. In some compositions, the conjugate is cholera toxin. In some compositions, the conjugate is an immunoglobulin. In some compositions, the conjugate is attenuated diphtheria toxin CRM 197 (Gupta, Vaccine 15, 1341-3 (1997).

The invention also provides pharmaceutical compositions comprising an agent effect to induce an immunogenic response against spore coating peptide in a patient with the proviso that the composition is free of Complete Freund's adjuvant. The invention also provides compositions comprising a viral vector encoding spore coating peptide or a an active fragment thereof effective to induce an immune response against spore coating peptide. Suitable viral vectors include herpes, adenovirus, adenoassociated virus, a retrovirus, sindbis, semiliki forest virus, vaccinia or avian pox.

The invention further provides methods of preventing or treating a disease which is caused by Mycobacteria. In such methods, an effective dose of spore coating peptide can be administered to a patient. The invention further provides for the use of spore coating peptide, or an antibody thereto, in the manufacture of a medicament for prevention or treatment of a disease caused by Mycobacteria.

In another aspect, the invention provides methods of assessing efficacy of a treatment method, described above, in a patient. In these methods, a baseline amount of antibody specific for a spore coating peptide is determined in a tissue sample from the patient before treatment with an agent. An amount of antibody specific for spore coating peptide in the tissue sample from the patient after treatment with the agent is compared to the baseline amount of spore coating peptide-specific antibody. An amount of spore coating peptide-specific antibody measured after the treatment that is significantly greater than the baseline amount of spore coating peptide-specific antibody indicates a positive treatment outcome.

In other methods of assessing efficacy of a treatment method in a patient, a baseline amount of antibody specific for a spore coating peptide in a tissue sample from a patient before treatment with an agent is determined. An amount of antibody specific for spore coating peptide in the tissue sample from the subject after treatment with the agent is compared to the baseline amount of spore coating peptide-specific antibody. A reduction or lack of significant difference between the amount of spore coating peptide-specific antibody measured after the treatment compared to the baseline amount of spore coating peptide-specific antibody indicates a negative treatment outcome.

In other methods of assessing efficacy of a treatment method in a patient a control amount of antibody specific for spore coating peptide is determined in tissue samples from a control population. An amount of antibody specific for spore coating peptide in a tissue sample from the patient after administering an agent is compared to the control amount of spore coating peptide-specific antibody. An amount of spore coating peptide-specific antibody measured after the treatment that is significantly greater than the control amount of spore coating peptide-specific antibody indicates a positive treatment outcome.

In other methods of assessing efficacy of a treatment method in a patient, a control amount of antibody specific for spore coating peptide in tissues samples from a control population is determined. An amount of antibody specific for spore coating peptide in a tissue sample from the patient after administering an agent is compared to the control amount of spore coating peptide-specific antibody. A lack of significant difference between the amount of spore coating peptide-specific antibody measured after beginning said treatment compared to the control amount of spore coating peptide-specific antibody indicates a negative treatment outcome.

Other methods of monitoring disease or susceptibility thereto in a patient, comprise detecting an immune response against spore coating peptide in a sample from the patient. In some such methods, the patient is being administered an agent effective to treat or prevent diseases caused by Mycobacteria, and the level of the response determines the future treatment regime of the patient.

In other methods of assessing efficacy of a treatment method in a patient a value for an amount of antibody specific for spore coating peptide in tissue sample from a patient who has been treated with an agent is determined. The value is compared with a control value determined from a population of patient experiencing amelioration of, or freedom from, symptoms of Mycobacterial disease due to treatment with the agent. A value in the patient at least equal to the control value indicates a positive response to treatment.

The invention further provides diagnostic kits for performing the above methods. Such kits typically include a reagent that specifically binds to antibodies to spore coating peptide or which stimulates proliferation of T-cells reactive with spore coating peptide.

DEFINITIONS

Proteins which are important for spore formation include those which are encoded by: a) genes for formation of spore coat, cortex and outer layer; b) genes involved in chromosome partitioning and translocation of DNA from mother cell to spore; and c) transcription factors regulating putative sporulation genes. Such proteins are termed "spore related proteins" or "spore related peptides" in the present application.

The term "spore related peptides" includes the peptides which are coded for by one of the genes listed in Tables 1-4, or a fragment thereof. Preferred such peptides are e.g. CotA (MM1618), CotD (MM4853), CotT (MM4208), SpoVK, CotSA (MM4226), YrbC (MM2098), SpoVE, Soj, and SpoIIIE. A spore forming peptide or fragment thereof should preferably be an immunogenic agent. Most preferred are CotA (MM1618), CotD (MM4853), CotT (MM4208), CotSA (MM4226), and YrbC (MM2098).

The term "spore forming peptide" indicates a spore related peptide that forms part of the spore. Similarly, "spore coating peptide" indicates a spore related peptide that forms part of the spore coat. The group "spore coating peptides" is thus a subgroup of the group "spore forming peptides" which in turn is a subgroup of "spore related peptides". When use is made of a spore related peptide in the present invention, the use of spore forming peptides and especially spore coating peptides are preferred embodiments, if not specifically indicated otherwise.

The term "patient" is meant to include animals such as humans and livestock such as cows, sheep, pigs, dogs, chicken, goat, kangaroo, ostrich, and buffalo and domestic animals such as cats, dogs, fish and birds. Also included are wild animals such as deer, reindeer, moose, wild boar.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

The terms "binding molecule" and "therapeutic agent" can be used interchangeably.

For sequence comparison, typically one sequence acts as a reference sequence, to which test sequences are compared.

When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence (s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). One example of algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (www.ncbi.nlm.nih.gov/). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89, 10915 (1989)) For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe.

Conservative substitutions involve substitutions between amino acids in the same class. Non-conservative substitutions constitute exchanging a member of one of these classes for a member of another.

Therapeutic agents of the invention are typically substantially pure. This means that an agent is typically at least about 50% w/w (weight/weight) purity, as well as being substantially free from interfering proteins and contaminants.

The agents may be at least about 80% w/w and, more preferably at least 90% w/w or about 95% w/w purity. However, using conventional protein purification techniques, homogeneous peptides of at least 99% w/w can be obtained.

Affinity between two entities means an affinity of at least $10^6$, $10^7$, $10^8$ $10^9$ $M^{-1}$, or $10^{10}$ $M^{-1}$. Affinities greater than $10^8$ $M^{-1}$ are preferred.

The term"antibody" is used to include intact antibodies and binding fragments thereof. Typically, fragments compete with the intact antibody from which they were derived for specific binding to an antigen. Optionally, antibodies or binding fragments thereof, can be chemically conjugated to, or expressed as, fusion proteins with other proteins.

The term"epitope" or "antigenic determinant" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996).

Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

The term "immunological" or "immune" response is the development of a beneficial humoral (antibody mediated) and/or a cellular (mediated by antigen-specific T cells or their secretion products) response directed against a spore coating peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4+ T helper cells and/or CD8+ cytotoxic T cells. The response may also involve activation of monocytes, macrophages, NK cells, basophils, dendritic cells, astrocytes, microglia cells, eosinophils or other components of innate immunity.

The presence of a cell-mediated immunological response can be determined by proliferation assays (CD4+ T cells) or CTL (cytotoxic T lymphocyte) assays (see Burke, supra; Tigges, supra). The relative contributions of humoral and cellular responses to the protective or therapeutic effect of an immunogen can be distinguished by separately isolating IgG and T-cells from an immunized syngeneic animal and measuring protective or therapeutic effect in a second subject.

The term "specific for" indicates that the variable regions of the antibodies, or binding molecules, recognize and bind spore coat peptides according to the invention exclusively (i.e., able to distinguish spore coating peptides from other similar polypeptides despite sequence identity, homology, or similarity found in the family of polypeptides), but may also interact with other proteins (for example, *S. aureus* protein A or other antibodies in ELISA techniques) through interactions with sequences outside the variable region of the antibodies, and in particular, in the constant region of the molecule. Screening assays in which one can determine binding specificity of an anti-spore coat peptide antibody are well known and routinely practiced in the art. (Chapter 6, Antibodies A Laboratory Manual, Eds. Harlow, et I al., Cold Spring Harbor Laboratory; Cold Spring Harbor, N.Y. (1988), herein incorporated by i reference in its entirety).

An "immunogenic agent" or "immunogen" is capable of inducing an immunological response against itself on administration to a patient, optionally in conjunction with an adjuvant.

The term "naked polynucleotide" refers to a polynucleotide not complexed with colloidal materials. Naked polynucleotides are sometimes cloned in a plasmid vector.

The term "adjuvant" refers to a compound that when administered in conjunction with an antigen augments the immune response to the antigen, but when administered alone does not generate an immune response to the antigen.

Adjuvants can augment an immune response by several mechanisms including lymphocyte recruitment, stimulation of B and/or T cells, and stimulation of macrophages.

The term "patient" includes human and other mammalian subjects that receive either prophylactic or therapeutic treatment.

Compositions or methods "comprising" one or more recited elements may include other elements not specifically recited.

For example, a composition that comprises a spore coating peptide encompasses both an isolated spore coating peptide and spore coating peptide as a component of a larger polypeptide sequence.

Flow cytometric profiles covering the complete life cycle of *M. marinum*. An old *M. marinum* stock was used to inoculate fresh medium and the progress of the culture to stationary phase through exponential growth was followed by flow cytometry. A 2-month old stock was spread on 7H10 agar plates with necessary supplements; cells were harvested at different times over a period of 2 months. The harvested cells were fixed in 70% ethanol, washed and resuspended in 0.1 volume TM (10 mM Tris-HCl pH 7.8; 10 mM $MgCl_2$), stained with mithramycin A and ethidium bromide and run in the flow cytometer (see Methods). The profiles are histograms of cell numbers plotted against their DNA content (column A: fluorescence calibrated in chromosome number equivalents) or size (column B: light scattering measured in arbitrary scale units kept constant for all histograms, not shown). The ages of the cultures, in h(ours) after inoculation into fresh medium, are shown on the left side of each row. The profiles on the top row, showing a stationary phase culture of the laboratory strain of the gram-negative bacterium *Escherichia coli* K12 (1-3 μm×1 μm cylinders containing 4.6 Mbp DNA per chromosome), were used as a calibration standard for estimating DNA-content and cell size in the *M. marinum* profiles.

FIG. 2

Figure 1:
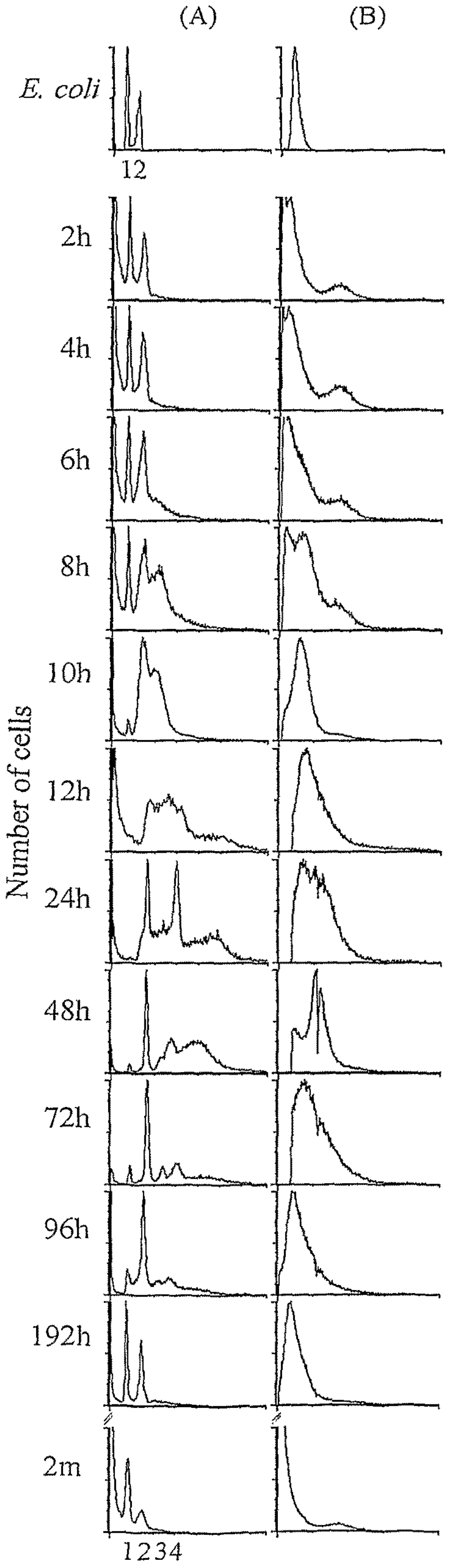
FIG. 1

Fluorescence microscopy of *M. marinum* at different stages of growth from fresh inoculum to stationary phase. 2-month old stock was spread onto plates and aliquots fixed in ethanol as described in FIG. 1 legend. The fixed cells were washed in PBS, layered onto thin films of agarose (1% in 0.9% NaCl) containing 0.5 μg/ml DAPI on a microscope slide and examined under a Zeiss (Axioplan 2) microscope with a CCD camera (see Methods). Panels a-g show cells harvested at 0 h, 6 h, 12 h, 72 h (3 d), 120 h (5 d), 168 h (1 w) and 336 h (2 w) after inoculation into fresh medium. Sizebars: 5 μm.

FIG. 3

Surface morphologies and internal structures of *M. marinum* cells at different stages of sporulation by scanning electron microscopy (SEM) and thin section transmission electron microscopy (TEM), respectively. Cells at different times after inoculation into fresh medium were prepared for SEM and TEM as described in Methods.

(A) SEM images: (a) isolated spores; (b) cells at germination; (c) putative endospores (5 days after inoculation) and (d) spore with a vegetative cell (7-day old culture). Sizebar: 1 μm.

(B) TEM images: (a) isolated spores; (b, c) mature spores; (d-f) different stages of germinating spores (6 h after inoculation); (g) a forespore at left and a mature endospore at right (5 day old culture). Magnifications: (a) 6000×; (b,c) 60000×; (d-f) 40000×; (g) 30000×.

FIG. 4

Surface Biochemistry and Heat Tolerance of Putative Spores from *M. marinum*

(a) Spore-specific differential staining of *M. marinum* cells from exponential and stationary phase cultures. Cells grown and harvested at different stages of growth were heat-fixed, stained and counterstained with malachite green and safranin, respectively (see Methods) and examined under the 100× objective of an Olympus CH30RF200 microscope.

(b) Colony forming ability after heat treatment. Plates containing exponential (12 h after inoculation) and stationary (after 14 days of growth) phase cells with and without exposure to wet-heat treatment (15 min, 65° C.).

(c) Rate of killing by wet-heat for *M. marinum* cells from exponential and stationary phases. Cells in exponential phase (12 h, diamonds) and stationary phase (14 d, squares) were exposed to wet-heat for different times, surviving colonies were expressed as percent against identical, unexposed cell population and plotted as a function of exposure times. Each point on the survival plot represents an average of at least three measurements (Table 5) with experimental variations indicated by error bars.

FIG. 5

Relative expression levels of putative sporulation genes from *M. marinum* genome at different stages of the life cycle. The mRNA levels of 9 genes from *M. marinum* genome, homologues of known sporulation genes from *Bacillus subtilis* and *Streptomyces coelicolor*, were compared using dot-blot hybridization as the culture progressed from exponential to stationary phase. Specific oligonucleotide probes (Table 6 for sequences) were used for each mRNA candidate. The relative intensities of the dots were normalized using corresponding 5S rRNA signals as internal standards and plotted in arbitrary units (Y-axis) as *M. marinum*-mRNA signals (identified as their homologues, X-axis) from cultures of different ages (bars of different patterns). All samples were analyzed at least three times and estimated experimental variations are indicated by error bars. The numerical values (Table 7) were obtained from Phosphor-Imager (Image Quant, Molecular Dynamics 400) analysis of the dot signals.

FIG. 6

Presence of Spore Particles in a Culture of *Mycobacterium bovis* (BCG).

(a) Phase fluorescence image of *M. bovis* cells from a six-month old culture. Sizebar: 5 μm.

(b) Differentially stained purified spore particles from BCG culture.

(c) SEM image of purified BCG spores. Sizebar: 1 μm.

(d) TEM image of thin sectioned purified BCG spores. Magnification: 60000×.

FIG. 7.

Morphologic comparison of *M. marinum* colonies from cultures germinated from single purified (see Methods) independent spore particles (a-d) with that from an exponentially growing culture inoculated from an old stock (e). Size bar: 1 cm.

FIG. 8.

RNase P RNA Gene Sequences from Independent Clones Originating from Isolated Single Spore Particles. Alignment of residues 89-315 of the RNase P RNA gene from the chromosomes of clonally isolated colonies. (1-4; SEQ ID NO: 27): Sequences from genomic DNA isolated from single colonies grown out of isolated single spore particle. (5; SEQ ID NO:27) Sequence from RNaseP RNA gene of *M. marinum* cloned in plasmid pIGn. (6; SEQ ID NO:28) *M. marinum* RNaseP RNA gene sequence obtained by blast search in the Singer database 24 using the *M. tuberculosis* H37Rv RNase P RNA gene sequence www.sanger.ac.uk./Projects/*M_tuberculosis*) reference. Sequences 1-5 are identical to those reported in the database except for two positions, 93 and 158. This could be due to the difference between the lab strain (ATCC 927) and the strain used to build the database (ATCC BAA-535), or an error in the database. Oligos used to PCR-amplify region 89-315 were:

```
Forward: 5'-ATCGAGGAAAGTCCGGACTTCACA-3'
(SEQ ID NO:29; comprising region 65-88)

Reverse: 5'-ACCCGCAGACTCGGGCGAGCAG-3'
(SEQ ID NO:30; complementary to region 294-315)
```

The forward oligo was used to obtain the sequences 1-5.

FIG. 9.

Life Cycle of *M. marinum* from Purified Spores by Microscopy.

a, pure spore population, 0 h. b, germinating spores, 6 h. c, germinated cells, 8 h. d, germinated cells, 24 h (1 d). e, same as d, 2 d. f, same as e, 3 d. g and h, appearance of endospores, 5 d. i, appearance of mature spore, 7 d. j, mature spores with cell debris, 14 d. Size bars: 5 μm.

FIG. 10.

Life cycle of *M. marinum* from purified spores by flow cytometry. A *M. marinum* culture was started from a purified spore suspension and followed through germination, exponential growth to sporulation in late stationary phase by flow cytometry. Columns (A) and (B) show DNA content (fluorescence calibrated in chromosome numbers) and cell size (light scattering in arbitrary units) distributions, respectively. The top panels refer to stationary phase LB cultures of *E. coli* used as calibration standards for DNA content and cell size. The nine lower panels correspond to *M. marinum* samples taken at: 0, 6, 8, 24, 48, 72, 120, 168 and 336 hours after suspension of the purified spores into the growth medium. Fixation and staining procedures were as described in Methods and in FIG. 1 legend.

The narrow size distribution and the shift of the peak as a whole with little widening implied synchronous transition of spores into vegetative cells. At late stationary stage (after 120 hours of growth), the cell size distribution implies emergence of endospores from the narrowing of the peak and its shift towards smaller size (Column B: 168 h and 336 h). The fluorescence profiles show the onset of DNA synthesis by 6 h after addition of growth medium; replication continues for 72 h after which non-replicative cell division is followed by sporulation.

DETAILED DESCRIPTION

The invention provides pharmaceutical compositions and methods for prophylactic and therapeutic treatment of diseases caused by a *Mycobacterium* infection. Furthermore, the invention provides such compositions and methods for treating such diseases wherein the *Mycobacterium* have formed spores.

The genus *Mycobacterium* includes non-pathogenic environmental bacteria as well as highly successful pathogens e.g. *Mycobacterium tuberculosis* (Mtb) and *Mycobacterium leprae* the etiological agents of tuberculosis and leprosy, respectively. While Mtb is human-specific, the closely related *Mycobacterium bovis* can infect both humans and animals and lead to tuberculosis regardless of host. Moreover, the mycobacteria *Mycobacterium avium* supsp. paratuberculosis (MAP), the causative agent of chronic diarrhea among ruminants (John's disease), can be present in food derived from cattle and it has been discussed that MAP is a causative agent of Crohn's disease in humans.

Another closely related *Mycobacterium, Mycobacterium marinum* causes a systemic tuberculosis-like infection and disease in ectothermic hosts e.g. fish and frogs. In comparison to Mtb, *M. marinum* grows with a relatively short doubling time and growth is limited at higher temperatures (see below), which makes *M. marinum* easier to handle than e.g. Mtb. *M. marinum* has recently emerged as model system to identify and study factors important for mycobacterial infections, disease development and its persistence. Pathogenic mycobacteria are invasive slow growing bacteria that can grow and multiply within macrophages. Moreover, most of them can establish long-term infections that can cause an acute or chronic stage of the disease or a stage that is clinically asymptomatic. In the latter situation the bacteria has the potential to resume growth after several decades of dormancy resulting in active disease.

The innate immune system is essential in defense against bacterial infections. Macrophages are important actors in this process and they play a significant role in the front line defense. Pathogenic mycobacteria e.g. Mtb are ingested by phagocytosis by alveolar macrophages at the site of entry and inside the macrophage the bacteria reside within a membrane-bound cytoplasmic vacuole referred to as the *Mycobacterium* phagosome. Pathogenic mycobacteria avoid phagolysosomal degradation by: 1) blocking acidification of the phagosome, 2) altering the protein content of the vacuole and 3) preventing interactions with other endosomal compartments. This ensures survival of the bacteria within the macrophage and subsequent spread of the pathogen to other cells e.g. dendrite cells and neutrophiles.

Complete Life Cycle of *M. marinum*: Cell Size and DNA Content Distribution

Changes in cell size and DNA content distributions of *M. marinum* cultures on plates through the full life cycle was followed by flow cytometry, Maisnier-Patin, S., Dasgupta, S., Krabbe, M., Nordstrom, K. Conversion to bidirectional replication after unidirectional initiation from R1 plasmid origin integrated at oriC in *Escherichia coli. Mol. Microbiol.* 30, 1067-1079 (1998). FIG. 1 shows the flow cytometric profiles for DNA content and cell size distributions of a culture from 2 h after inoculation to 2 months. Measurements were taken every 2 h for 12 h, at 24 h, every 24 h till 96 h, 196 h and at 2 months. The overnight stationary culture of *Escherichia coli* K12, used as a calibration standard, showed a uniform population with a narrow size distribution (single sharp symmetrical peak with normal distribution; top row, column B) containing either one or two full-sized chromosomes (two sharp peaks indicated by numbers 1 and 2 in the fluorescence histogram pre-calibrated in terms of genome size using *E. coli* chromosome as standard; see top row, column A). The flow cytometric profiles of *M. marinum* cells from the 2 months old stock remain unchanged from Oh (not shown) up to 4 h after inoculation into fresh medium. They showed two distinct classes of cell population: the majority consisted of very small size cells with fluorescence corresponding to one *M. marinum* genome (6.6 Mbp, www.sanger.ac.uk/Projects/*M__marinum*/) or less, and a subpopulation with fluorescence corresponding to 2-genome equivalent DNA (indicated by the size bars labeled 1 and 2 in the 2 month-DNA content profile). At 6 h, the light scattering-peak representing cell size started to broaden suggesting increased in cell size accompanied with higher than 2-genome equivalent DNA content in some cells (start of DNA synthesis). With progression of time, the cell size and DNA content distributions underwent drastic changes—separate peaks representing very small and big cells were replaced by a single, broader peak corresponding to a continuous size distribution of exponentially growing population of cells (10 h after inoculation). The fluorescence peak corresponding to 2 chromosome equivalent of DNA broadened into a continuity of 2 to 4 or more chromosomes indicating ongoing DNA synthesis. In keeping with this, the 1-chromosome peak disappeared gradually as more cells entered the replicative phase from the "non-replicating, small-size" spore-like state after 10 h of growth in fresh medium. The very small cells with one genome equivalent of DNA persisted until about 6 h after inoculation into fresh media and then both disappeared to be replaced by cells of bigger size containing 2-4 chromosome equivalents of DNA (see 10 h panels). The very small size cells are believed to represent the non-replicating spore-like particles. With further incubation, the cell size distribution reached its highest average value with broadest distribution (24 h) and then divided into smaller, more uniform size distributions; the DNA content indicated that ongoing DNA synthesis was gradually ending, and cells with 2 and 4 chromosome equivalents of DNA started to appear (24 h). Replication in a subpopulation continued while non-replicative division was evident from the increasing proportion of 2-chromosome cells after 96 h of growth (see 48 h, 72 h and 96 h). After about a week, almost all cells were in a single, smaller size distribution with either 1 or 2 full size chromosome equivalents of DNA: at two months, the majority of the cells had been converted to the very small size 1-chromosome form with a small subpopulation of bigger cells containing 2 chromosome equivalents of DNA, similar to the initial 2 month old stock culture at 2 h (compare the flow cytometric profiles for 2 h and 2 month in FIG. 1).

Figure 2:
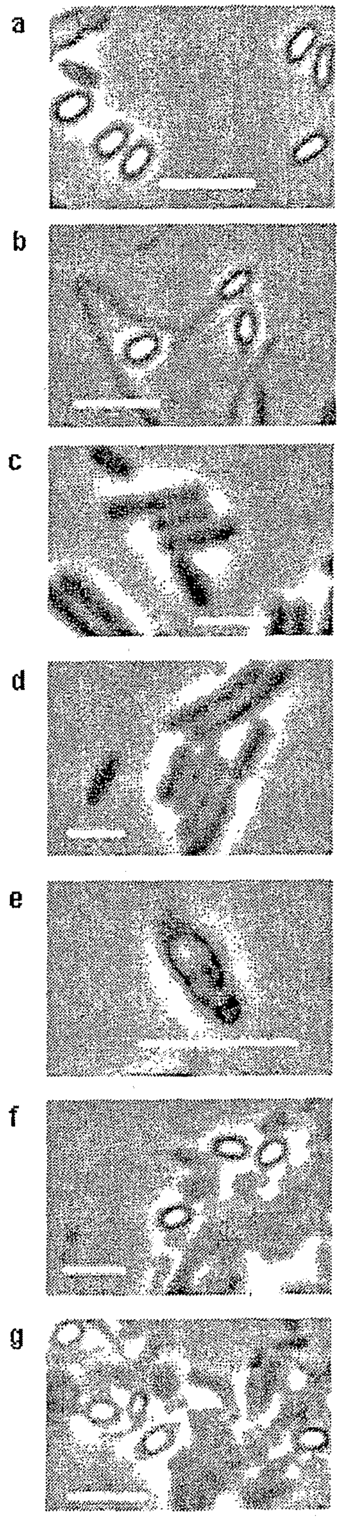

To clarify the nature of the very small, non-replicating cells at the early and late stages of growth (2 h-8 h and after 192 h), the cell population was examined at different stages of growth from old stock to stationary through the exponential phase under phase-fluorescence microscope. The ethanol-fixed cells were stained with 4,6-diamidino-2-phenylindole (DAPI) to visualize DNA. FIG. 2 shows the phase-fluorescence micrographs of cells from: 2 month old stock (at 0 h of growth), 6 h, 12 h, 3 days, 5 days, 7 days and 14 days of growth (a-g, respectively) following inoculation into fresh media. The old stock (FIG. 2*a*) showed tiny ellipsoidal particles with bright reflectance in phase images characteristic of spores, Hitchins, A. D., Kahn, A. J., Slepecky, R. A. Interference contrast and phase contrast microscopy of sporulation and germination of *Bacillus megaterium. J. Bacteriol.* 96, 1811-1817 (1968), possibly corresponding to the non-replicating small cells in flow cytometric profiles (see 2 h, FIG. 1). These cells, though containing one genome equivalent of DNA, showed lower DAPI fluorescence compared to the vegetative cells (e.g. 12 h, FIG. 2) suggesting poor uptake of the dye; this also explains the low fluorescence of the population of small cells in flow cytometric profiles (see FIG. 1: 2 h-6 h and 2 months). After plating onto fresh medium cylindrical vegetative cells were seen emerging from the spores in mid-germination after 6 h of incubation (FIG. 2*b*), i.e. after about one generation time. Fluorescence from DAPI-stained DNA was visible in the elongated part. By 12 h, almost all cells were in the state of vegetative growth and looked like cylindrical bacteria with clearly visible DAPI-stained nucleoids (FIG. 2*c*) and this continued up to 3 days (FIG. 2*d*). At day 5, endospore-like species (FIG. 2*e*), with a shining spot within the cell near one pole with a constriction separating the bright spot from the rest of the cell was observed. After a week of growth, spores started appearing as seen from bright phase images and damping of fluorescence (FIG. 2*f*). The spore formation continued with the progression of the culture-age (FIG. 2*g*, after 2 weeks of growth). From the combined flow cytometric and fluorescence microscopic data it seems that *M. marinum* starts to sporulate some time after stationary phase has been established, though the exact time of onset and commitment to sporulation is yet to be determined (see FIGS. 1 and 2). However, according to the present data sporulation began late in the life cycle of the *M. marinum* culture, most likely after several hours from the onset of stationary phase. On the other hand germination or emergence from sporulation seemed to begin as soon as the spores are exposed to fresh medium.

Single Spore Develops into a Single *M. marinum* Colony

Figure 7:
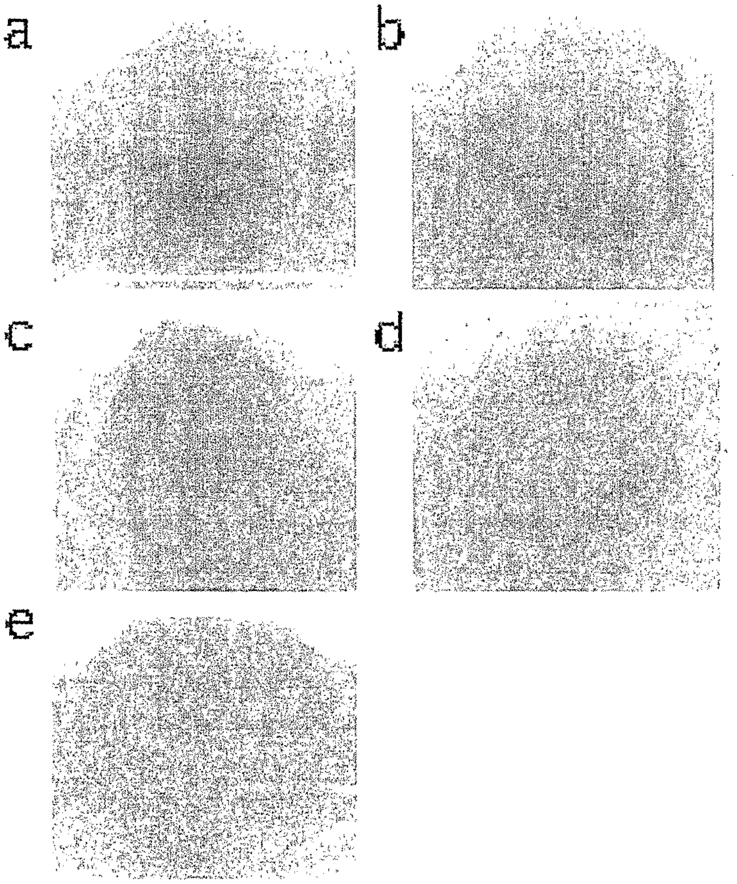
Figure 8:
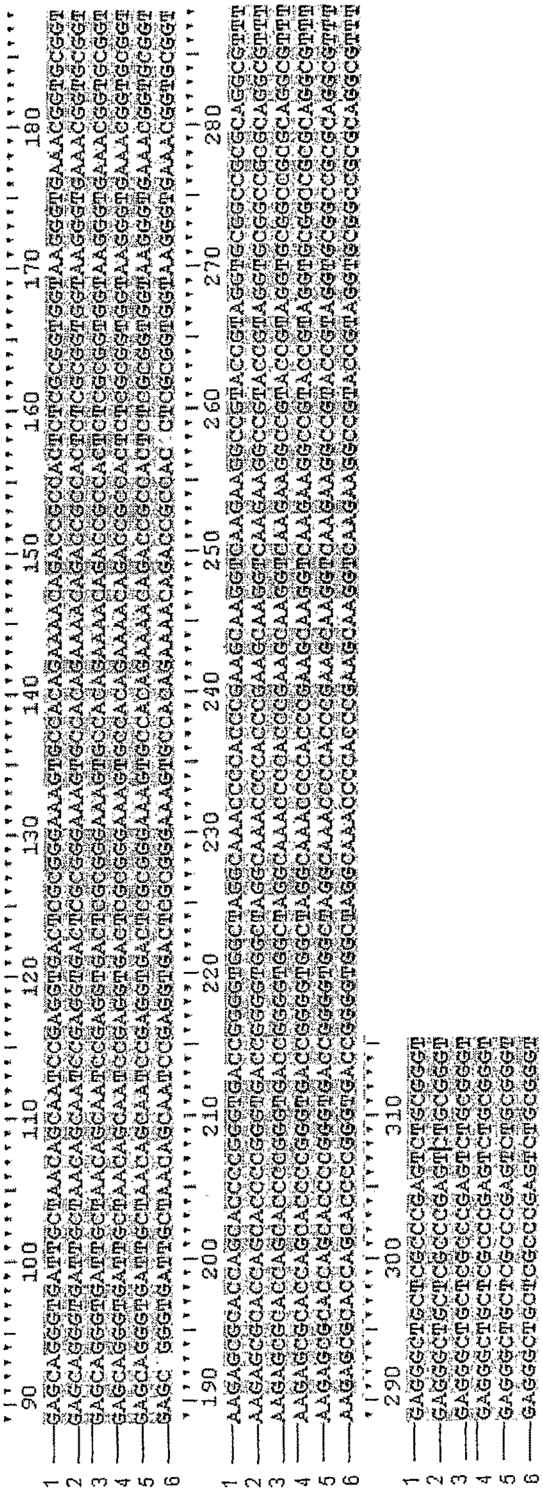
Figure 9:
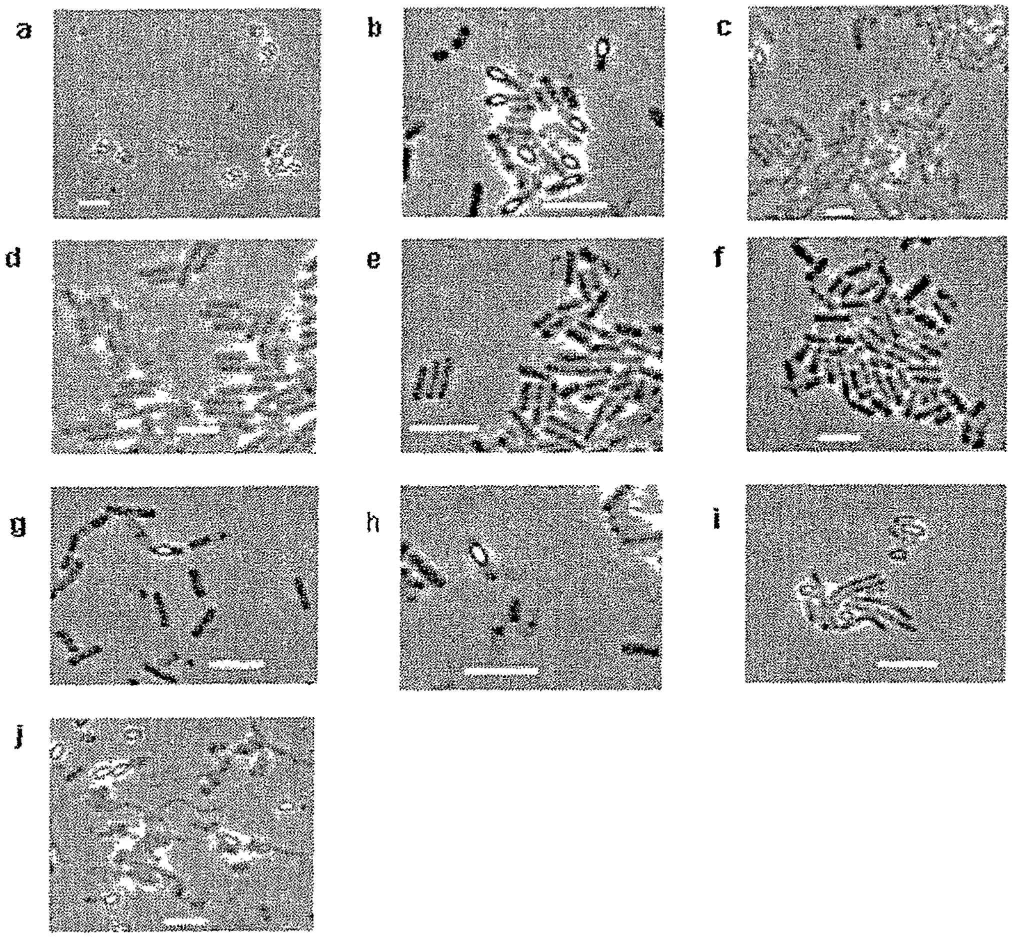
Figure 10:
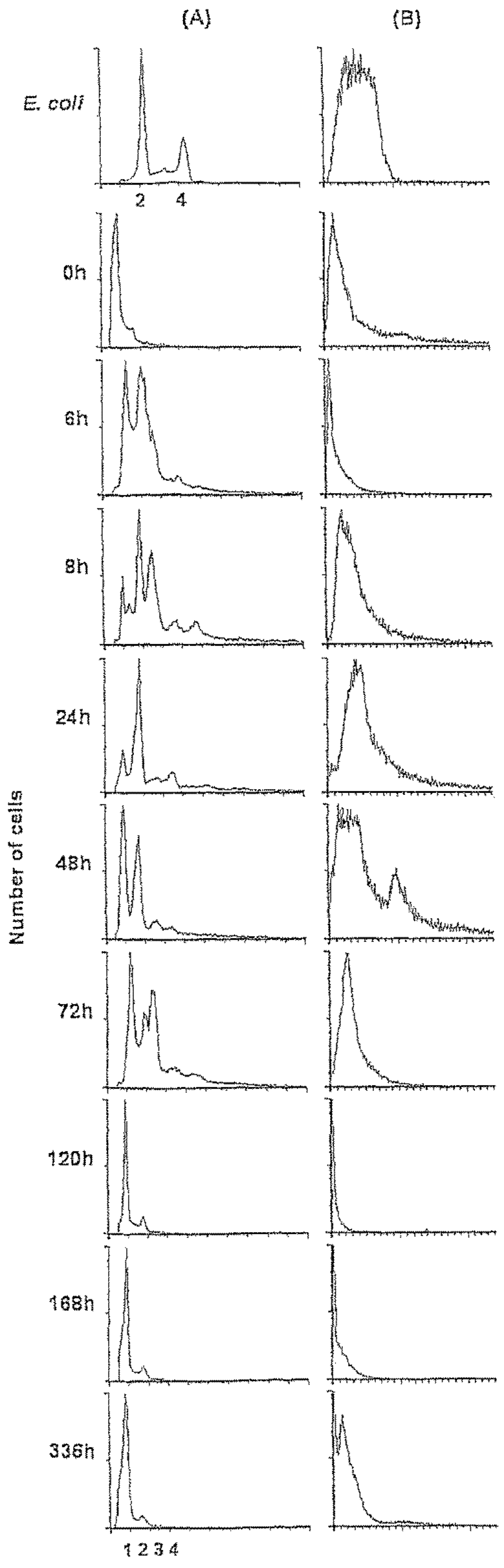

To eliminate the possibility that these spore-like particles were a contamination from another spore former, pure spores free of vegetative cells were isolated (Methods, FIG. 9*a*). A batch of pure spores was diluted serially such that there would be one or less viable spore in each diluted fraction (see Methods). Samples from 10 replicates of dilutions were plated. After a week of incubation, four of the ten plates showed a single colony that had germinated and grown. Each of these colonies, originating from four independent single spores, was morphologically identical to a colony of *M. marinum* (FIG. 7). To verify that these colonies were indeed *M. marinum*, part of the RNase P RNA gene was PCR-amplified using total DNA extracted from each one of them. DNA sequencing (FIG. 8) confirmed that the colonies were *M. marinum*. The isolated *M. marinum* spores were also freshly plated, and their life cycles were followed with phase-fluorescence microscopy and flow cytometry (FIGS. 9 and 10). They were observed to germinate to vegetative cells, which again sporulated in the late stationary phase. Thus, the purified spore particles germinated into *M. marinum* cells and were therefore not contaminants.

Figure 3:
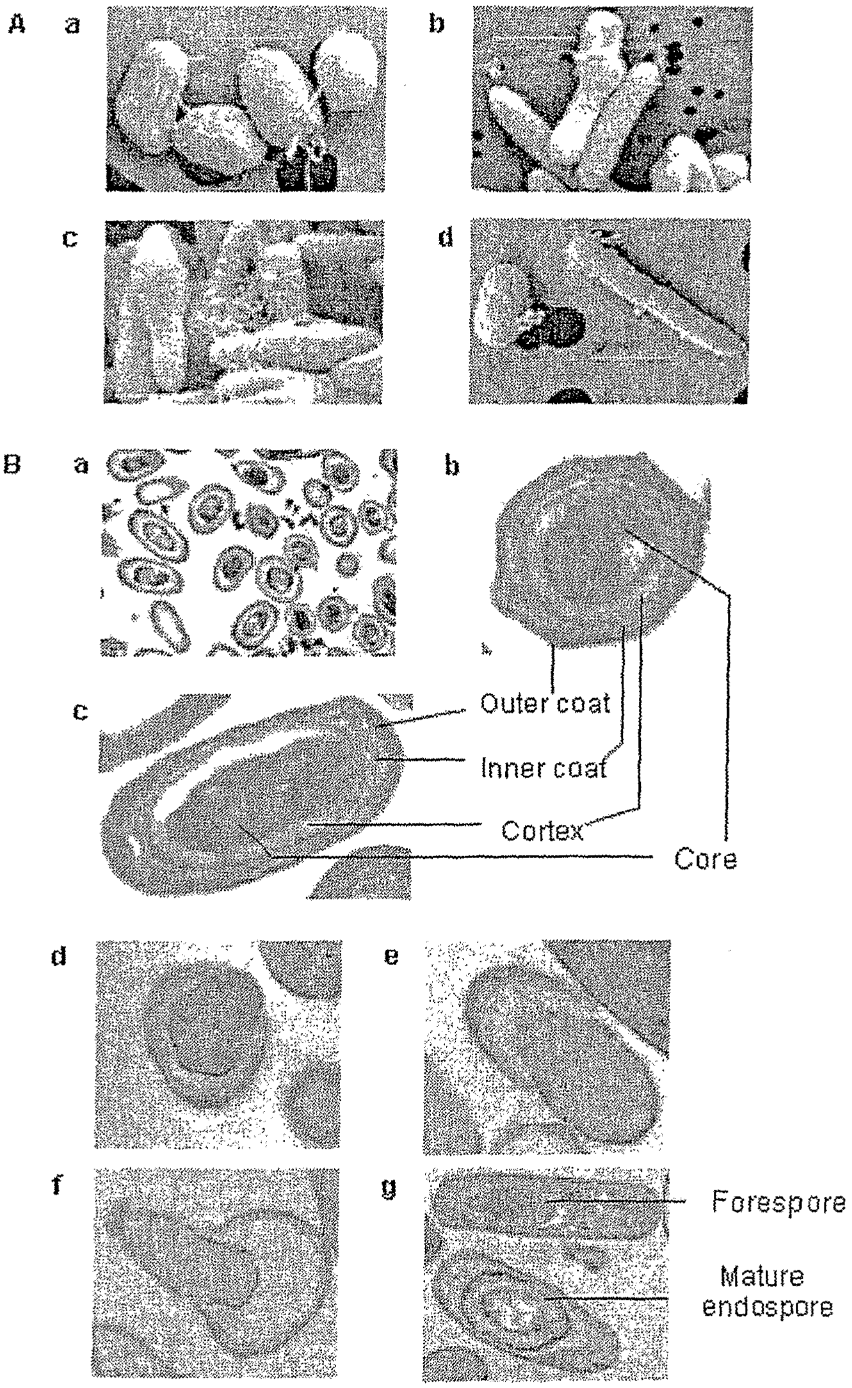

Electron Microscopic Visualization of the Spore Particles, Sporulation and Germination The very distinct sizes and morphologies of cells in sporulating and germinating states were examined by scanning electron micrograph (SEM), Lackner P. et al. Scanning electron microscopy of the neuropathology of murine cerebral malaria. *Malar J.* 5, 116 (2006). FIG. 3 (panel A; a-d) shows SEM images of *M. marinum* at various stages of sporulation. Different types of cells seen are: a) isolated spores; b) a vegetative cell germinating out from a spore (6 h); c) cells with probable endospores showing bulges near one pole (day 5); and d) a spore with a vegetative cell (day 7). The internal structures of the spores were examined by transmission electron microscopy (TEM) of thin section of fixed, isolated spores (FIG. 3 panel B; a-c) and *M. marinum* cells from cultures at different stages (FIG. 3 panel B; d-g). By comparing with the TEM images of well-characterized *Bacillus* spores, Wang, L., Perpich, J., Driks, A., and Kroos, L. Maintaining the transcription factor SpoIIID level late during sporulation causes spore defects in *Bacillus subtilis. J. Bacteriol.* 189, 7302-7309 (2007) with that of isolated *M. marinum* spores, the outer coat, inner coat, cortex and core of the mature spore were clearly identified (FIG. 3 panel B; b and c). The TEM image cells 6 hours after inoculation of spores into fresh media, showed vegetative cells gradually germinating out of empty spores with disrupted surface (FIG. 3 panel B; d-f). In the TEM images of the day 5 cells that showed endospore-like species in the phase-fluorescence microscopy (FIG. 2*e*), structures that looked like endospores in their different stages of maturation were seen (FIG. 3 panel B; g, forespore and mature endospore, side by side). These are morphologically very similar to published images of *Bacillus* spp. endospores, Erlendsson, L. S., Möller, M., and Hederstedt, L. *Bacillus subtilis* StoA is a thiol-disulfide oxidoreductase important for spore cortex synthesis. *J. Bacteriol.* 186, 6230-6308 (2004). No such structure was observed in the TEM images of a batch of vegetatively growing cells in exponential phase (not shown). These data suggest that *M. marinum* indeed forms spores and that the sporulation pathway proceeds via endospore formation.

Physical and Biochemical Properties of *M. marinum* Spore Particles and Presence of Genomic Informations Necessary for Sporulation in Mycobacteria If the 'spore-like' particles visualized microscopically in the stationary *M. marinum* culture are true spores they should exhibit: (i) special surface-biochemistry that allows staining by spore-specific stains; (ii) high resistance towards physical and chemical stresses; and (iii) presence of the genetic apparatus necessary for entry into and exit from the spore state. Differential spore staining and a heat tolerance test, respectively, were performed to check the first two requirements, and bioinformatics for the third.

The classical differential spore staining was done using malachite green as the primary stain, water as the decolorizing agent and safranin as the counterstain Cappuccino, J. G., Sherman, N. in Microbiology, a Laboratory Manual (Benjamin Cummings, San Francisco, sixth edition, 2001). As shown in FIG. 4*a*, the vegetative cells appeared to have lost the primary stain and taken the counterstain and appeared red. In contrast, the spores retained the primary stain and appeared green, indicating that the surface of the spore-like particles in *M. marinum* cultures have similar biochemical properties as the well-known *B. subtilis* spores.

Figure 4:
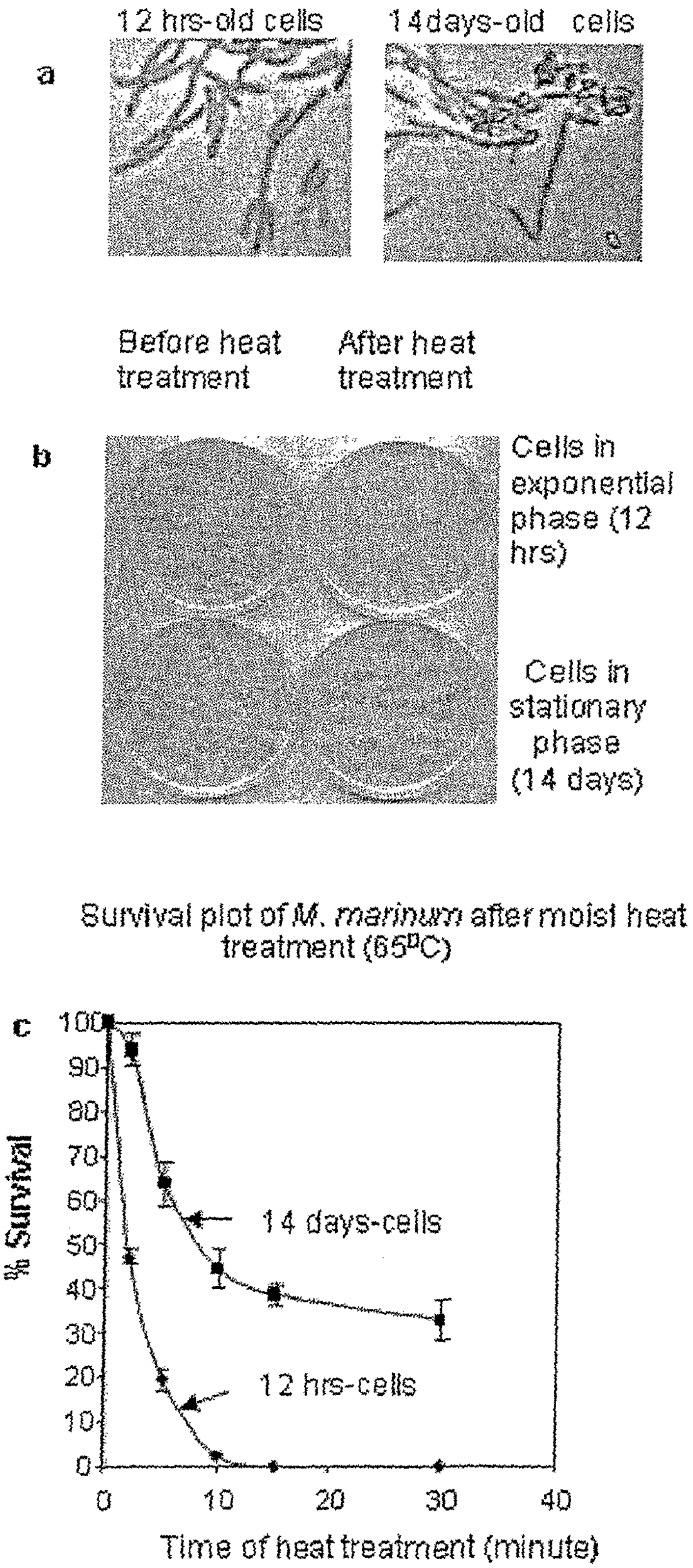

Next, the effect of wet heat treatment (65° C., 15 minutes) on exponentially growing (12 h) and stationary phase (14 days) cells was compared, Chakrabarty, K. et al., *Infection and Immunity.* 74, 4430-4438 (2006). While the exponentially growing cells were almost completely killed after 10 min of heat treatment, nearly 40% of the cells in stationary phase survived even after 30 min of treatment (FIGS. 4, *b* and *c*). This is qualitatively proportional to the spore population seen in stationary cultures. The spores were also demonstrated to be more resistant to glutaraldehyde treatment compared to cells grown in exponential phase (not shown).

Figure 5:
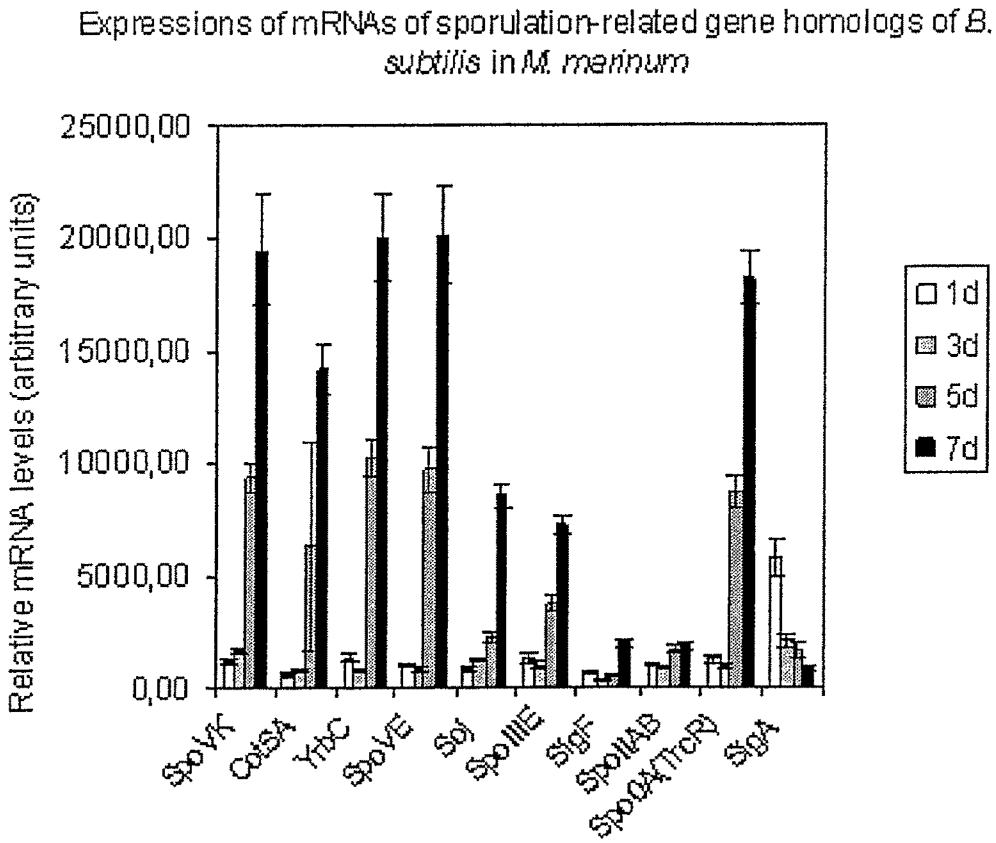

Finally, the mycobacterial genome was scanned to look for genes relevant to spore formation. Genes essential for sporulation have been identified in the gram-positive bacteria e.g. *B. subtilis*, genolist.pasteur.fr/SubtiList/, and *Streptomyces coelicolor*, streptomyces.org.uk/sco/index.html. A reciprocal best hit (RBH) approach was used, Rivera, M. C., Jain, R., Moore, J. E. & Lake, J. A. Genomic evidence for two functionally distinct gene classes. *Proc. Natl. Acad. Sci. USA* 95, 6239-6244 (1998), to identify putative orthologues of well-known sporulation genes in the *M. marinum*, ftp.sanger.ac.uk/pub/pathogens/mm/, and *M. tuberculosis*, cmr.tigr.org/tigr-scripts/CMR/CmrHomePage.cgi, genomes (Tables 1-4).). Based on the functional annotation of the *B. subtilis* genes, these were divided into three classes and include: a) genes for formation of spore coat, cortex, and outer layer; b) genes involved in chromosome partitioning and translocation of DNA from mother cell to spore; and c) transcription factors regulating putative sporulation genes. Some of these genes, from all three classes, were selected to check their relative levels of mRNA expression by dot blot analysis,'Sambrook, J., Fritsch, E. F., Maniatis, T. Molecular Cloning, a Laboratory Manual. (Cold Spring Harbor Laboratory Press, New York, third edition, 2001). As shown in FIG. 5 the selected genes were transcribed in *M. marinum*. Significantly, the expression of the sporulation gene-homologues depended on the age of the culture. The mRNA levels of the homologues, genolist.pasteur.fr/SubtiList/, of SpoVK (disruption of this gene leads to immature spore formation, stage V), CotSA (Spore coat protein), YrbC (similar to spore coat protein), and SpoVE (required for spore cortex peptidoglycan synthesis, stage V) showed a sharp increase from day 5, continuing to day 7. Homologues of Soj (centromere-like function, involved in forespore chromosome partitioning/negative regulation of sporulation initiation) and SpoIIIE (DNA translocase required for chromosome partitioning through the septum into the forespore) showed a similar pattern but more modest increase compared to the former four genes. Some weaker hits were obtained in the bioinformatic search for some major transcription factors, and some of them were probed for, e.g. Spo0A (master regulator for commitment to sporulation) sharp increase from day 5, which continues to day 7. The top scoring Spo0A hit in Mtb strain CDC1551 is the trcR gene that encodes a DNA binding response regulator, Haydel, S. E., Clark-Curtiss, J. E. The *Mycobacterium tuberculosis* TrcR response regulator represses transcription of the intracellularly expressed Rv1057 gene. *J. Bacteriol.* 188, 150-159 (2006), (TrcR in FIG. 5). The other factors, SigF (late sporulation specific RNA polymerase sigma factor) showed a modest increase at day 7 while the homologue to the anti-SigF, SpoIIAB, showed a modest increase at days 5 and 7. The "housekeeping" sigma factor, SigA (: $\sigma^{70}$) mRNA, Gruber, T. M., Gross, C. A. Multiple sigma subunits and the partitioning of bacterial transcription space. *Annu. Rev. Microbiol.* 57, 441-466 (2003), of *M. marinum* does not play any direct role in sporulation, Piggot, P. J., Hilbert, D. W. Sporulation of *Bacillus subtilis. Current Opinion in Microbiology.* 7, 579 (2004), and its mRNA level decreased as the culture entered and progressed through stationary phase. These data support the presence of a molecular pathway for sporulation in *M. marinum* and conceivably also in Mtb. The expressions of these genes at protein level, and their further characterizations, such as phosphorylation/dephosphorylation patterns, are yet to be examined. The fact that no strong hits were found for the major transcription factor specific for sporulation might indicate that either: a) the corresponding genes have diverged in their sequences while retaining their functions, or b) these factors are unique to mycobacteria and have to be identified using other methods. Note that the RNA samples prepared from the day 7 cells represented genes expressed in a mixed population of vegetative cells and spores (FIGS. 2*f* and 3 panel A; d).

Spore Particles in Old Cultures of the *M. bovis* BCG Strain

We also observed spore-like species in late stationary cultures of the *Myocbacterium bovis* BCG strain. In phase fluorescence microscopy, BCG cells from a six-month-old plate showed bright, refractive particles (FIG. 6*a*) similar to the *M. marinum* spores. These particles were purified (see Methods) and subjected to spore-specific staining (FIG. 6*b*) and electron microscopy (both SEM and TEM, FIGS. 6*c* and *d*, respectively). On the basis of these data, it appears that these particles are similar to *M. marinum* spores. Hence, these data provide experimental evidences in favor of the possibility that sporulation is a more general feature of mycobacteria, and not limited to *M. marinum*. Consequently, sporulation might be considered as a general strategy for survival under stress.

Therapeutic agents for use in the present invention induce an immune response against a spore coating peptide, or other proteins or peptides which are involved in spore formation. These agents include the spore coating peptide itself and variants thereof, analogs and mimetics of the spore coating peptide that induce and/or crossreact with antibodies to spore coating peptides, and antibodies or T-cells reactive with spore coating peptides. Induction of an immune response can be active as when an immunogen is administered to induce antibodies or T-cells reactive with a spore coating peptide in a patient, or passive, as when an antibody is administered that itself binds to a spore coating peptide in patient.

The therapeutic agent used in the claimed methods can be any of the naturally occurring forms of a protein involved in spore formation, such as those proteins derived from the genes in Tables 1-4. Such a gene include in particular: a) genes for formation of spore coat, cortex and outer layer; b) genes involved in chromosome partitioning and translocation of DNA from mother cell to spore; and c) transcription factors regulating putative sporulation genes. A number of these genes were chosen from all three classes (a, b, or c) to check their relative levels of mRNA expression by dot blot analysis. The selected genes may be transcribed in *M. marinum*. The expression of the sporulation gene-homologues depends on the age of the culture. The mRNA levels of the homologues of SpoVK (disruption of this gene leads to immature spore formation, stage V), CotSA (Spore coat protein), YrbC (similar to spore coat protein), and SpoVE (required for spore cortex peptidoglycan synthesis, stage V) showed a sharp increase from day 5, which continued to day 7. Homologues of Soj (centromere-like function, involved in forespore chromosome partitioning/negative regulation of sporulation initiation) and SpoIIIE (DNA translocase required for chromosome partitioning through the septum into the forespore)

The therapeutic agent may be an immunogenic peptide, fragment or analog of a protein encoded by a gene shown in Tables 1-4.

Table 1: Putative sporulation gene orthologues of *B. subtilis* in *Mycobacterium* spp. and *S. Coelicolor*

| *B. subtilis* 168 | | | Putative ortholog[b] | | | | | | | |
|---|---|---|---|---|---|---|---|---|---|---|
| | | | *M. marinum* | | *M. tuberculosis* CDC15S1 | | *M. tuberculosis* H37Rv | | *S. coelicolor* A3(2) | |
| Gene id[a] | Gene name | Annotation | RBH | RSD | RBH | RSD | RBH | RSD | RBH | RSD |
| BG10054 | SpoOJ | chromosome positioning near the pole and | MM5481 | | MT_4036 | | Rv3917c | | SCO3887 | |

-continued

Table 1: Putative sporulation gene orthologues of *B. subtilis* in *Mycobacterium* spp. and *S. Coelicolor*

| | | | | | | | | |
|---|---|---|---|---|---|---|---|---|
| | | transport through the polar septum/antagonist of Soj-dependent inhibition of speculation initiation | | | | | | |
| BG10055 | Soj | centromere-like function involved in forespore chromosome partitioning/negative regulation of sporulation initiation | MM5482 | | MT_4037 | Rv3918c | SCO3886 | |
| BG10061 | Jag | SpoIIIJ-associated protein | MM5484 | | MT_4039 | Rv3920c | SCO3884 | |
| BG10062 | SpoIIIJ | essential for sigma-G activity at stage III | MM5485 | | MT_4040 | Rv3921c | SCO3883 | |
| BG10087 | BofA | inhibition of the pro-sigma-K processing machinery | | MM0678 | | | | |
| BG10116 | SpoVC | probable peptidyl-tRNA hydrolase | MM4473 | | MT_1042 | Rv1014c | SCO3125 | |
| BG10119 | SpoVT | transcriptional positive and negative regulator of sigma-G-dependent genes | | | | Rv2595 | | |
| BG10127 | SpoIIE | serine phosphatase (sigma-F activation)/ asymmetric septum formation | | | | | | SCO0717 |
| BG10203 | SplB | spore photoproduct lyase | | | | | SCO7402 | |
| BG10226 | SpoVE | required forspore cortex peptidoglycan synthesis | MM3194 | | MT_2213 | Rv2154c | SCO2607 | |
| BG10296 | SpoIIAA | anti-anti-sigma factor | MM5181 | MM0737 | MT_3789 | Rv3687c | SCO3067 | |
| BG10297* | SpoIIAB | anti-sigma factor/ serine kinase | MM5186 | | | | SCO7322 | |
| BG10298* | SigF | RNA polymerase sporulation forespore-specific (early) sigma factor | MM1248 | | MT_3385 | Rv3286c | SCO5243 | SCO0600 |
| BG10332 | SpoIVTB | membrane metalloprotease required for the processing of pro-sigma-K to active sigma-K | | MM2075 | | | SCO1652 | |
| BG10337 | Obg | GTP-binding protein involved in initiation of sporulation (SpoOA activation) | MM3765 | | MT_2516 | Rv2440c | SCO2595 | |
| BG10346 | SpoVID | required for assembly of the spore coat | | MM4057 | | | | |
| BG10458 | SpoIVCA | site-specific DNA recombinase required for creating the sigK gene (excision of the skin element) | MM2129 | pMM23-15 | MT_3573 | Rv1586c | SCO6405 | |
| BG10490 | CotA | spore coat protein (outer) | MM1618 | | | | SCO3440 | |
| BG10493 | CotD | spore coat protein (inner) | MM4853 | | | | | |
| BG10495 | CotT | spore coat protein (inner) | MM4208 | | MT_1271 | Rv1233c | SCO4822 | |
| BG10611 | SpsC | spore coat polysaccharide synthesis | MM2320 | | | Rv1504c | SCO5746 | |
| BG10613 | SpsE | spore coat polysaccharide synthesis | | | | | SCO4881 | |
| BG10617 | SpsI | spore coat polysaccharide synthesis | MM0606 | | MT_0348 | Rv0334 | SCO1388 | |

-continued

Table 1: Putative sporulation gene orthologues of *B. subtilis* in *Mycobacterium* spp. and *S. Coelicolor*

| | | | | | | |
|---|---|---|---|---|---|---|
| BG10618 | SpsJ | spore coat polysaccharide synthesis | MM1082 | MT_3570 | Rv3464 | SCO0749 |
| BG10619 | SpsK | spore coat polysaccharide synthesis | MM1275 | MT_3366 | Rv3266c | SCO7194 |
| BG10763 | SpoIIIE | DNA translocase required for chromosome partitioning through the septum into the forespore | MM1967 | MT_2819 | Rv2748c | SCO5750 |
| BG10765* | SpoOA | two-component response regulator central for the initiation of sporulation | MM4455 | MT_1062 | Rv1033c | SCO2013 |
| BG11039 | SpoVK | disruption leads to the production of immature spores | MM0541 | MT_0295 | Rv0282 | SCO1024 |
| BG11197 | CgeE | maturation of the outermost layer of the spore | | MT_2818 | Rv2747 | |
| BG11231 | KipI | inhibitor of KinA | MM0524 | MT_0277 | Rv0264c | SCO0442 |
| BG11381 | CotSA | spore coat protein | MM4226 MM0812 | MT_0504 | Rv0486 | SCO2132 SCO4204 |
| BG11687 | YqgT | unknown; similar to gamma-D-glutamyl-L-diamino acid endopeptidase I | | | | SCO1948 |
| BG11806 | Tlp | small acid-soluble spore protein (thioredoxin-like protein) | MM3184 | | | |
| BG12181 | YdhD | unknown; similar to unknown proteins from *B. subtilis* | | | | SCO1429 |
| BG12229 | Spo0M | sporulation-control gene | | | | SCO0247 |
| BG12358 | KapD | inhibitor of the KinA pathway to sporulation | | | | SCO7397 |
| BG13288 | YkuD | unknown; similar to unknown proteins | | MT_0125 | Rv0116c | |
| BG13781 | SafA | morphogenetic protein associated with SpoVID | MM0022 | MT_1271 | Rv1233c | |
| BG13783 | YrbC | unknown; similar to spore coat protein | MM2098 | MT_2678 | Rv2603c | SCO1521 |
| BG13907 | YtpT | unknown; similar to DNA translocase stage III sporulation protein (SpoIIIE) | MM1967 | MT_2819 | Rv2748c | |
| BG14193 | KipA | antagonist of KipI | MM0523 | MT_0276 | Rv0263c | SCO0443 |
| BG14195 | SpsL | spore coat polysaccharide synthesis | MM1081 | MT_3571 | Rv3465 | SCO0400 |

| | | | Distance measure | | | | | | | |
|---|---|---|---|---|---|---|---|---|---|---|
| *B. subtilis* 168 | | | *M. marinum* | | *M. tuberculosis* CDC1551 | | *M. tuberculosis* H37Rv | | *S. coelicolor* A3(2) | |
| Gene id[a] | Gene name | Annotation | Expect[c] | Distance[d] | Expect[c] | Distance[d] | Expect[c] | Distance[d] | Expect[c] | Distance[d] |
| BG10054 | SpoOJ | chromosome positioning near the pole and transport through the polar septum/antagonist of Soj-dependent inhibition of speculation initiation | 3.7E−51 | 1.4 | 1.3E−48 | 1.4 | 1.2E−48 | 1.4 | 4.5E−52 | 1.5 |
| BG10055 | Soj | centromere-like function involved in forespore chromosome partitioning/negative | 4.1E−68 | 1.0 | 1.6E−66 | 1.0 | 1.5E−66 | 1.0 | 2.3E−71 | 0.9 |

-continued

Table 1: Putative sporulation gene orthologues of *B. subtilis* in *Mycobacterium* spp. and *S. Coelicolor*

| | | | | | | | | | | |
|---|---|---|---|---|---|---|---|---|---|---|
| | | regulation of sporulation initiation | | | | | | | | |
| BG10061 | Jag | SpoIIIJ-associaled protein | 1.5E−13 | 2.9 | 3.2E−13 | 3.1 | 2.9E−13 | 3.1 | 3.4E−15 | 2.6 |
| BG10062 | SpoIIIJ | essential for sigma-G activity at stage III | 1.5E−24 | 2.4 | 1.4E−23 | 2.3 | 1.3E−23 | 2.3 | 1.0E−29 | 2.2 |
| BG10087 | BofA | inhibition of the pro-sigma-K processing machinery | | 2.8 | | | | | | |
| BG10116 | SpoVC | probable peptidyl-tRNA hydrolase | 3.3E−36 | 1.6 | 3.2E−36 | 1.6 | 3.0E−36 | 1.6 | 4.8E−32 | 1.7 |
| BG10119 | SpoVT | transcriptional positive and negative regulator of sigma-G-dependent genes | | | | | 4.2E−05 | 2.3 | | |
| BG10127 | SpoIIE | serine phosphatase (sigma-F activation)/ asymmetric septum formation | | | | | | | | 3.6 |
| BG10203 | SplB | spore photoproduct lyase | | | | | | | 1.8E−25 | 3.0 |
| BG10226 | SpoVE | required forspore cortex peptidoglycan synthesis | 7.9E−58 | 2.2 | 6.1E−58 | 2.1 | 5.6E−58 | 2.1 | 5.0E−60 | 1.9 |
| BG10296 | SpoIIAA | anti-anti-sigma factor | 3.2E−06 | 3.3 | 8.6E−04 | 3.7 | 8.0E−04 | 3.7 | 6.5E−12 | 2.5 |
| BG10297* | SpoIIAB | anti-sigma factor/ serine kinase | 4.3E−07 | | | | | | 3.3E−10 | |
| BG10298* | SigF | RNA polymerase sporulation forespore-specific (early) sigma factor | 2.4E−33 | | 2.4E−31 | | 2.2E−31 | | 1.2E−37 | 1.9 |
| BG10332 | SpoIVTB | membrane metalloprotease required for the processing of pro-sigma-K to active sigma-K | | 3.8 | | | | | 7.0E−09 | 4.0 |
| BG10337 | Obg | GTP-binding protein involved in initiation of sporulation (SpoOA activation) | 1.8E−92 | 1.3 | 2.4E−88 | 1.4 | 2.2E−88 | 1.4 | 1.7E−91 | 1.3 |
| BG10346 | SpoVID | required for assembly of the spore coat | | 4.8 | | | | | | |
| BG10458 | SpoIVCA | site-specific DNA recombinase required for creating the sigK gene (excision of the skin element) | 8.6E−14 | 3.7 | 2.0E−12 | 4.1 | 2.0E−12 | 4.1 | 5.5E−14 | 3.9 |
| BG10490 | CotA | spore coat protein (outer) | 1.0E−23 | 3.6 | | | | | 6.2E−15 | 2.7 |
| BG10493 | CotD | spore coat protein (inner) | 2.9E−05 | 3.9 | | | | | | |
| BG10495 | CotT | spore coat protein (inner) | 1.2E−06 | | | 3.6 | | 4.1 | | 5.4 |
| BG10611 | SpsC | spore coat polysaccharide synthesis | 3.3E−50 | 2.3 | | | 4.1E−39 | 1.6 | 1.5E−20 | 2.8 |
| BG10613 | SpsE | spore coat polysaccharide synthesis | | | | | | | 2.2E−34 | 2.4 |
| BG10617 | SpsI | spore coat polysaccharide synthesis | 1.2E−38 | 1.8 | 4.3E−41 | 1.7 | 4.0E−41 | 1.7 | 3.4E−25 | |
| BG10618 | SpsJ | spore coat polysaccharide synthesis | 3.4E−73 | 1.2 | 1.0E−71 | 1.2 | 9.4E−72 | 1.2 | 1.3E−75 | 1.1 |
| BG10619 | SpsK | spore coat polysaccharide synthesis | 1.8E−42 | 2.0 | 2.2E−46 | 1.8 | 2.0E−46 | 1.8 | 1.1E−18 | 3.2 |
| BG10763 | SpoIIIE | DNA translocase required for chromosome partitioning through | 5.4E−120 | | 3.1E−118 | | 2.9E−118 | | 4.5E−122 | 1.9 |

-continued

Table 1: Putative sporulation gene orthologues of *B. subtilis* in *Mycobacterium* spp. and *S. Coelicolor*

| | | | | | | | | | | |
|---|---|---|---|---|---|---|---|---|---|---|
| | | the septum into the forespore | | | | | | | | |
| BG10765* | SpoOA | two-component response regulator central for the initiation of sporulation | 2.4E−17 | | 1.6E−15 | | 3.6E−15 | | 1.6E−17 | |
| BG11039 | SpoVK | disruption leads to the production of immature spores | 7.2E−48 | 1.9 | 2.3E−49 | 1.9 | 2.2E−49 | 1.9 | 2.1E−53 | 1.6 |
| BG11197 | CgeE | maturation of the outermost layer of the spore | | | 7.4E−04 | 4.7 | 8.3E−04 | 4.5 | | |
| BG11231 | KipI | inhibitor of KinA | 7.3E−23 | 3.3 | 4.4E−16 | 3.4 | 4.1E−16 | 2.8 | 1.2E−26 | 2.3 |
| BG11381 | CotSA | spore coat protein | 3.1E−22 | 3.0 | | 3.2 | | 3.2 | 3.4E−24 | 3.0 |
| BG11687 | YqgT | unknown; similar to gamma-D-glutamyl-L-diamino acid endopeptidase I | | | | | | | 1.2E−04 | 4.0 |
| BG11806 | Tlp | small acid-soluble spore protein (thioredoxin-like protein) | 3.5E−04 | 14.2 | | | | | | |
| BG12181 | YdhD | unknown; similar to unknown proteins from *B. subtilis* | | | | | | | 2.8E−05 | |
| BG12229 | SpoOM | sporulation-control gene | | | | | | | 2.9E−32 | 2.1 |
| BG12358 | KapD | inhibitor of the KinA pathway to sporulation | | | | | | | 1.2E−10 | 3.7 |
| BG13288 | YkuD | unknown; similar to unknown proteins | | | 3.6E−04 | 3.4 | 4.9E−04 | 3.5 | | 3.5 |
| BG13781 | SafA | morphogenetic protein associated with SpoVID | 1.2E−05 | 4.6 | 5.5E−07 | | 4.7E−07 | | | |
| BG13783 | YrbC | unknown; similar to spore coat protein | 2.5E−52 | 1.3 | 4.0E−54 | 1.3 | 3.7E−54 | 1.3 | 7.8E−55 | 1.2 |
| BG13907 | YtpT | unknown; similar to DNA translocase stage III sporulation protein (SpoIIIE) | | 1.9 | | 2.0 | | 2.0 | | |
| BG14193 | KipA | antagonist of KipI | 8.9E−22 | 2.7 | 1.7E−19 | 2.9 | 8.4E−20 | 2.9 | 2.0E−25 | 2.5 |
| BG14195 | SpsL | spore coat polysaccharide synthesis | 1.8E−09 | 2.9 | 3.0E−10 | 3.0 | 2.7E−10 | 3.0 | 1.1E−09 | 2.8 |

[a]Ids marked with asterisk indicates a weak putative ortholog (see Methods)
[b]Putative ortholog gene identifier. Gene identifiers justified to the left or right are identified using the RBH or RSD approaches, respectively. A centered gene identifier was identified by both approaches.
[c]Expect value of putative RBH ortholog from forward BLAST search using *B. subtilis* sporulation gene as query.
[d]Distance estimated by RSD approach

TABLE 2

Table 2: Putative sporulation gene orthologues of *S. coelicolor* in *Mycobacterium* spp. and *B. Subtilis*

| *S. coelicolor* A3(2) | | | Putative ortholog[a] | | | | | | | |
|---|---|---|---|---|---|---|---|---|---|---|
| | | | *M. marinum* | | *M. tuberculosis* CDC1551 | | *M. tuberculosis* H37Rv | | *B. subtilis* 168 | |
| Gene id | Gene name | Annotation | RBH | RSD | RBH | RSD | RBH | RSD | RBH | RSD |
| SCO0506 | nadE2 | NH(3)-dependent NAD(+)synthetase (nadE1) | | | | | | | BG10694 | |
| SCO1024 | SCG20A.04 | conserved hypothetical protein | | MM0541 | | | | | BG11039 | |
| SCO1177 | SCG11A.08 | putative gntR-famly transcriptional regulator | | | | MT_0514 | | Rv0494 | | |
| SCO1434 | SC6D7.05c | putative CbxX/CfqX family protein | MM5443 | | MT_3981 | | Rv3868 | | | |

TABLE 2-continued

Table 2: Putative sporulation gene orthologues of *S. coelicolor* in *Mycobacterium* spp. and *B. Subtilis*

| | | | | | | |
|---|---|---|---|---|---|---|
| SCO1772 | SCI51.12c | putative partitioning or sporulation protein | MM2523 | MT_1749 | Rv1708 | |
| SCO1950 | SCC54.10c | hypothetical protein | MM2230 | MT_1466 | Rv1423 | BG12402 |
| SCO2083 | ftsQ | sporulation protein | MM3191 | MT_2210 | Rv2151c | |
| SCO2085 | ftsW | putative cell division protein | MM3194 | MT_2213 | Rv2154c | |
| SCO2607 | sfr | Sfr protein | | | | BG10226 |
| SCO2805 | 2SCC13.13 | conserved hypothetical protein | | MT_1099 | Rv1069c | |
| SCO3034 | whiB | sporulation regulatory protein | MM1282 | MT_3358 | Rv3260c | |
| SCO3579 | SCH17.13c | putative regulatory protein | MM5170 | MT_3783 | Rv3681c | |
| SCO3846 | SCH69.16 | putative FtsW/RodA/SpoVE family cell cycle protein | MM0019 | MT_0020 | Rv0017c | |
| SCO3883 | StH24.05 | putative membrane protein | MM5485 | MT_4040 | Rv3921c | BG10062 |
| SCO3886 | StH24.08 | putative partitioning or sporulation protein | MM5482 | MT_4037 | Rv3918c | BG10055 |
| SCO3887 | StH24.09 | putative partitioning or sporulation protein | MM5481 | MT_4036 | Rv3917c | BG10054 |
| SCO3934 | SCQ11.17 | ftsK/spoIIIE family protein 4328870: 4330171 forward MW: 45953 | MM3126 | | | |
| SCO4767 | SC6G4.45c | putative regulatory protein | MM1132 | MT_3525 | Rv3416 | |
| SCO5302 | SC5G9.31 | putative integral membrane cell-cycle protein | MM0019 | MT_0020 | Rv0017c | |
| SCO5320 | SC6G9.13 | whiE protein I | | | | BG12784 |
| SCO5321 | SC6G9.12c | polyketide hydroxylase | MM3384 | | | |
| SCO5621 | whiG | RNA polymerase sigma factor WhiG | | | | BG10751 |
| SCO5633 | traSA | integrase fusion protein | | MT_2962 | Rv2894c | BG12099 |
| SCO5750 | SC7C7.05 | ftsK homolog | MM1967 | MT_2819 | Rv2748c | BG10763 |
| SCO6435 | SC9B5.02 | hypothetical protein | MM4895 | | | |

| | | | Distance measure | | | | | | | |
|---|---|---|---|---|---|---|---|---|---|---|
| *S. coelicolor* A3(2) | | | *M. marinum* | | *M. tuberculosis* CDC1551 | | *M. tuberculosis* H37Rv | | *B. subtilis* 168 | |
| Gene id | Gene name | Annotation | Expect[b] | Distance[c] | Expect[b] | Distance[c] | Expect[b] | Distance[c] | Expect[b] | Distance[c] |
| SCO0506 | nadE2 | NH(3)-dependent NAD(+)synthetase (nadE1) | | | | | | | 2.7E−69 | 1.0 |
| SCO1024 | SCG20A.04 | conserved hypothetical protein | | 2.9 | | | | | 1.1E−53 | 1.6 |
| SCO1177 | SCG11A.08 | putative gntR-famly transcriptional regulator | | | | 2.6 | | 2.6 | | |
| SCO1434 | SC6D7.05c | putative CbxX/CfqX family protein | 1.7E−64 | 2.6 | 3.8E−65 | 2.5 | 3.5E−65 | 2.5 | | |
| SCO1772 | SCI51.12c | putative partitioning or sporulation protein | 2.6E−98 | 0.7 | 2.3E−90 | 0.5 | 4.8E−100 | 0.6 | | |
| SCO1950 | SCC54.10c | hypothetical protein | 3.5E−119 | 0.4 | 2.7E−119 | 0.4 | 2.5E−119 | 0.4 | 1.1E−26 | 2.9 |
| SCO2083 | ftsQ | sporulation protein | 2.3E−19 | 3.1 | 4.1E−14 | 3.1 | 3.8E−14 | 3.1 | | |
| SCO2085 | ftsW | putative cell division protein | 1.8E−76 | 1.6 | 5.1E−77 | 1.6 | 4.7E−77 | 1.6 | | |
| SCO2607 | sfr | Sfr protein | | | | | | | 2.8E−60 | 1.9 |
| SCO2805 | 2SCC13.13 | conserved hypothetical protein | | | 3.8E−04 | | 4.3E−04 | 5.2 | | |
| SCO3034 | whiB | sporulation regulatory protein | 4.4E−32 | 0.4 | 5.6E−32 | 0.3 | 5.2E−32 | 0.5 | | |
| SCO3579 | SCH17.13c | putative regulatory protein | 2.6E−27 | 0.7 | 2.2E−28 | 0.7 | 2.1E−28 | 0.7 | | |
| SCO3846 | SCH69.16 | putative FtsW/RodA/SpoVE family cell cycle protein | 2.3E−106 | | 2.5E−107 | | 2.3E−107 | | | |
| SCO3883 | StH24.05 | putative membrane protein | 2.4E−34 | 2.2 | 3.5E−35 | 2.0 | 3.2E−35 | 2.0 | 5.5E−30 | 2.2 |

TABLE 2-continued

Table 2: Putative sporulation gene orthologues of *S. coelicolor* in *Mycobacterium* spp. and *B. Subtilis*

| | | | | | | | | | | |
|---|---|---|---|---|---|---|---|---|---|---|
| SCO3886 | StH24.08 | putative partitioning or sporulation protein | 1.0E−87 | 0.6 | 1.9E−86 | 0.6 | 1.8E−86 | 0.6 | 1.3E−71 | 0.9 |
| SCO3887 | StH24.09 | putative partitioning or sporulation protein | 5.3E−75 | 0.9 | 5.9E−76 | 0.9 | 5.4E−76 | 0.9 | 2.4E−52 | 1.5 |
| SCO3934 | SCQ11.17 | ftsK/spoIIIE family protein 4328870: 4330171 forward MW: 45953 | 2.7E−21 | | | | | | | |
| SCO4767 | SC6G4.45c | putative regulatory protein | 2.1E−32 | 0.8 | 1.9E−31 | 0.8 | 1.7E−31 | 0.8 | | |
| SCO5302 | SC5G9.31 | putative integral membrane cell-cycle protein | | 1.1 | | 1.2 | | 1.2 | | |
| SCO5320 | SC6G9.13 | whiE protein I | | | | | | | 1.3E−06 | 2.6 |
| SCO5321 | SC6G9.12c | polyketide hydroxylase | 8.5E−40 | 3.1 | | | | | | |
| SCO5621 | whiG | RNA polymerase sigma factor WhiG | | | | | | | 6.9E−48 | 1.6 |
| SCO5633 | traSA | integrase fusion protein | | | | 3.0 | | 2.8 | | 3.6 |
| SCO5750 | SC7C7.05 | ftsK homolog | 1.1E−219 | 1.0 | 1.35−218 | 1.4 | 1.2E−218 | 0.9 | 2.5E−122 | 1.9 |
| SCO6435 | SC9B5.02 | hypothetical protein | 1.5E−04 | | | | | | | |

[a]Putative ortholog gene identifier. Gene identifiers justified to the left or right are identified using the RBH or RSD approaches, respectively. A centered gene identifier was identified by both approaches.
[b]Expect value of putative RBH ortholog from forward BLAST search using *S. coelicolor* sporulation gene as query
[c]Distance estimated by RSD approach

TABLE 3

Table 3: Functional annotations for putative sporulation gene orthologues of *B. subtilis* in *Mycobacterium* spp. and *S. Coelicolor*

| *B. subtilis* 168 | | | *M. marinum* | | *M. tuberculosis* CDC1551 | |
|---|---|---|---|---|---|---|
| Gene id[a] | Gene name | Annotation | Putative ortholog | Annotation | Putative ortholog | Annotation |
| BG10054 | SpoOJ | chromosome positioning near the pole and transport through the polar septum/ antagonist of Soj-dependent inhibition of sporulation initiation | MM5481 | undefined product | MT_4036 | ParB family protein |
| BG10055 | Soj | centromere-like function involved in forespore chromosome partitioning/ negative regulation of sporulation initiation | MM5482 | undefined product | MT_4037 | Soj family protein |
| BG10061 | Jag | SpoIIIJ-associated protein | MM5484 | undefined product | MT_4039 | R3H domain-containing protein |
| BG10062 | SpoIIIJ | essential for sigma-G activity at stage III | MM5485 | undefined product | MT_4040 | conserved hypothetical protein |
| BG10087 | BofA | inhibition of the pro-sigma-K processing machinery | MM0678 | undefined product | | |
| BG10116 | SpoVC | probable peptidyl-tRNA hydrolase | MM4473 | undefined product | MT_1042 | peptidyl-tRNA hydrolase (pth) [3.1.1.29] |
| BG10119 | SpoVT | transcriptional positive and negative regulator of sigma-G-dependent genes | | | | |
| BG10203 | SplB | spore photoproduct lyase | | | | |
| BG10226 | SpoVE | required for spore cortex peptidoglycan synthesis | MM3194 | undefined product | MT_2213 | cell division protein FtsW (ftsW-2) |
| BG10296 | SpoIIAA | anti-anti-sigma factor | MM5181<br>MM0737 | undefined product<br>undefined product | MT_3789 | anti-anti-sigma factor |
| BG10297* | SpoIIAB | anti-sigma factor/serine kinase | MM5186 | undefined product | | |
| BG10298* | SigF | RNA polymerase sporulation forespore-specific (early) sigma factor | MM1248 | undefined product | MT_3385 | stress response/stationary phase sigma factor SigF (sigF) |
| BG10332 | SpoIVFB | membrane metalloprotease required for the processing of pro-sigma-K to active sigma-K | MM2075 | undefined product | | |
| BG10337 | Obg | GTP-binding protein involved in initiation of sporulation (SpoOA activation) | MM3765 | undefined product | MT_2516 | GTP-binding protein (obg) |

TABLE 3-continued

Table 3: Functional annotations for putative sporulation gene orthologues of *B. subtilis* in *Mycobacterium* spp. and *S. Coelicolor*

| | | | | | | |
|---|---|---|---|---|---|---|
| BG10346 | SpoVID | required for assembly of the spore coat | MM4057 | undefined product | MT__3573 | integrase, putative |
| BG10458 | SpoIVCA | site-specific DNA recombinase required for creating the sigK gene (excision of the skin element) | MM2129 | undefined product | | |
| | | | pMM23-15 | undefined product | | |
| BG10490 | CotA | spore coat protein (outer) | MM1618 | undefined product | | |
| BG10493 | CotD | spore coat protein (inner) | MM4853 | undefined product | | |
| BG10495 | CotT | spore coat protein (inner) | MM4208 | undefined product | MT__1271 | hypothetical protein |
| BG10611 | SpsC | spore coat polysaccharide synthesis | MM2320 | undefined product | | |
| BG10613 | SpsE | spore coat polysaccharide synthesis | | | | |
| BG10617 | SpsI | spore cost polysaccharide synthesis | MM0606 | undefined product | MT__0348 | glucose-1-phosphate thymidylyltransferase (rfbA) [2.7.7.24] |
| BG10618 | SpsJ | spore coat polysaccharide synthesis | MM1082 | undefined product | MT__3570 | dTDP-glucose-4,6-dehydratase (rfbB) [4.2.1.46] |
| BG10619 | SpsK | spore coat polysaccharide synthesis | MM1275 | undefined product | MT__3366 | dTDP-4-dehydrorhamnose reductase (strL) |
| BG10763 | SpoIIIE | DNA translocase required for chromosome partitioning through the septum into the forespore | MM1967 | undefined product | MT__2819 | cell division protein FtsK (ftsK) |
| BG10765* | SpoOA | two-component response regulator central for the initiation of sporulation | MM4455 | undefined product | MT__1062 | DNA-binding response regulator TrcR (trcR) |
| BG11039 | SpoVK | disruption leads to the production of immature spores | MM0541 | undefined product | MT__0295 | ATPase, AAA family |
| BG11197 | CgeE | maturation of the outermost layer of the spore | | | MT__2818 | acetyltransferase, GNAT family |
| BG11231 | KipI | inhibitor of KinA | MM0524 | undefined product | MT__0277 | conserved hypothetical protein |
| BG11381 | CotSA | spore coat protein | MM4226 | undefined product | MT__0504 | glycosyl transferase |
| | | | MM0812 | undefined product | | |
| BG11687 | YqgT | unknown; similar to gamma-D-glutamyl-L-diamino acid endopeptidase I | | | | |
| BG11806 | Tlp | small acid-soluble spore protein (thioredoxin-like protein) | MM3184 | undefined product | | |
| BG12181 | YdhD | unknown; similar to unknown proteins from *B. subtilis* | | | | |
| BG12229 | SpoQM | sporulation-control gene | | | | |
| BG12358 | KapD | inhibitor of the KinA pathway to sporulation | | | | |
| BG13288 | YkuD | unknown; similar to unknown proteins | | | MT__0125 | conserved hypothetical protein |
| BG13781 | SafA | morphogenetic protein associated with SpoVID | MM0022 | undefined product | MT__1271 | hypothetical protein |
| BG13783 | YrbC | unknown; similar to spore coat protein | MM2098 | undefined product | MT__2678 | conserved hypothetical protein |
| BG13907 | YtpT | unknown; simitar to DNA translocase stage III sporulation protein (SpoIIIE) | MM1967 | undefined product | MT__2819 | cell division protein FtsK (ftsK) |
| BG14193 | KipA | antagonist of KipI | MM0523 | undefined product | MT__0276 | urea amidolyase-related protein |
| 8G14195 | SpsL | spore coat polysaccharide synthesis | MM1081 | undefined product | MT__3571 | dTDP-4-dehydrorhamnose 3,5-epimerase (strM) [5.1.3.13] |

| *B. subtilis* 168 | | | *M. tuberculosis* H37Rv | | *S. coelicolor* A3(2) | |
|---|---|---|---|---|---|---|
| Gene id[a] | Gene name | Annotation | Putative ortholog | Annotation | Putative ortholog | Annotation |
| BG10054 | SpoOJ | chromosome positioning near the pole and transport through the polar septum/ antagonist of Soj-dependent inhibition of sporulation initiation | Rv3917c | (MTV028.08c), len: 344. Unknown, similar to TR: O0519D CHROMOSOME PARTITIONING PROTEIN PARB from *CAULOBACTER CRESCENTUS* (293 aa). fasta scores; opt: 564 z-score: 784.2 E( ): 0, 38.6% identity in 308 aa overlap; and to SPOJ__BACSU P26497 stage 0 sporulation pr (parA) | SCO3887 | putative partitioning or sporulation protein |

TABLE 3-continued

Table 3: Functional annotations for putative sporulation gene orthologues of *B. subtilis* in *Mycobacterium* spp. and *S. Coelicolor*

| | | | | | | |
|---|---|---|---|---|---|---|
| BG10055 | Soj | centromere-like function involved in forespore chromosome partitioning/ negative regulation of sporulation initiation | Rv3918c | (MTV028.09c), len: 347. Unknown, similar to TR:O05189(EMBL: U87804) CHROMOSOME PARTITIONING PROTEIN PARA from *CAULOBACTER CRESCENTUS* (266 aa), fasta scores; opt: 787 z-score: 990.9 E( ): 0, 50.6% identity in 261 aa overlap and to SOJ__BACSU P37522 soj protei (parB) | SCO3886 | putative partitioning or sporulation protein |
| BG10061 | Jag | SpoIIIJ-associated protein | Rv3920c | hypothetical protein | SCO3884 | conserved hypothetical protein |
| BG10062 | SpoIIIJ | essential for sigma-G activity at stage III | Rv3921c | hypothetical protein | SCO3883 | putative membrane protein |
| BG10087 | BofA | inhibition of the pro-sigma-K processing machinery | | | | |
| BG10116 | SpoVC | probable peptidyl-tRNA hydrolase | Rv1014c | (MTCY10G2.35), pth, len: 191. Probable peptidyl-tma hydrolase, similar to eg PTH__ECOLI P23932 peptidyl-tma hydrolase (ec 3.1.1.29) (194 aa), fasta scores, opt: 472, E( ): 2.3e−25, (39.6% identity in 187 aa overlap) (pth) | SCO3125 | peptidyl-tRNA hydrolase |
| BG10119 | SpoVT | transcriptional positive and negative regulator of sigma-G-dependent genes | Rv2595 | hypothetical protein | | |
| BG10203 | SplB | spore photoproduct lyase | | | SCO7402 | putative lyase |
| BG10226 | SpoVE | required for spore cortex peptidoglycan synthesis | Rv2154c | (MTCY270.14), len: 524. ftsW, probable cell division protein FtsW, related to MTCY10H4.17C, 3.2e−17. FASTA best: SP5E__BACSU P07373 stage v sporulation protein e(366 aa) opt: 755 z-score: 727.2 E( ): 1.6e−33; (38.4% identity in 357 aa overlap) (ftsW) | SCO2607 | Sfr protein |
| BG10296 | SpoIIAA | anti-anti-sigma factor | Rv3687c | hypothetical protein | SCO3067 | putative anti anti sigma factor |
| BG10297* | SpoIIAB | anti-sigma factor/serine kinase | | | SCO7322 | putative anti-sigma factor (fragment) |
| BG10298* | SigF | RNA polymerase sporulation forespore-specific (early) sigma factor | Rv3286c | (MTCY71.26), len: 261, sigF, almost identical to *M. tuberculosis* MTU41061__1 Q50547, stress response/ stationary phase sigma factor f (261 aa). Also similar to U00012__11 *Mycobacterium leprae* Q49668 RPSB (118 aa, 71.2% identity in 111 aa overlap) Contains p (sigF) | SCO5243 | RNA polymerase sigma factor |
| BG10332 | SpoIVFB | membrane metalloprotease required for the processing of pro-sigma-K to active sigma-K | | | SCO1652 | conserved hypothetical protein |
| BG10337 | Obg | GTP-binding protein involved in initiation of sporulation (SpoOA activation) | Rv2440c | (MTCY428.06), len: 479. Probable obg, nucleotide-binding protein, equivalent to *Streptomyces griseus* D87916\|D87916__3 (478 aa) fasta scores, opt 1328 z-score: 1443.0 E( ): 0; 58.9% identity in 479 aa overlap; also similar to eg OBG__BACSU P20964 spoOb-ass (obg) | SCO2595 | GTP-binding protein |
| BG10346 | SpoVID | required for assembly of the spore coat | Rv1586c | hypothetical protein | SCO6405 | putative DNA recombinase |
| BG10458 | SpoIVCA | site-specific DNA recombinase required for creating the sigK gene (excision of the skin element) | | | | |

TABLE 3-continued

Table 3: Functional annotations for putative sporulation gene orthologues of *B. subtilis* in *Mycobacterium* spp. and *S. Coelicolor*

| | | | | | | |
|---|---|---|---|---|---|---|
| BG10490 | CotA | spore coat protein (outer) | | | SCO3440 | hypothetical protein |
| BG10493 | CotD | spore coat protein (inner) | | | | |
| BG10495 | CotT | spore coat protein (inner) | Rv1233c | hypothetical protein | | |
| BG10611 | SpsC | spore coat polysaccharide synthesis | Rv1504c | hypothetical protein | SCO5746 | hypothetical protein |
| BG10613 | SpsE | spore coat polysaccharide synthesis | | | SCO4881 | putative polysaccharide biosynthesis related protein |
| BG10617 | SpsI | spore cost polysaccharide synthesis | Rv0334 | (MTCY279.01), len: 288. rfbA, glucose-1-phosphate thymidylyl-transferase highly similar to many eg. RBA1__ECOLI P37744 glucose-1-phosphate thymidylyltransferase (293 aa), fasta scores; opt: 1199 z-score: 1884.1 E( ): 0, 62.0% identity in 284 aa overlap (rmlA) | SCO1388 | putative mannose-1-phosphate guanyltransferase |
| BG10618 | SpsJ | spore coat polysaccharide synthesis | Rv3464 | (MTCY13E12.17), len: 331. rmlB. Function: probable DTDP-GLUCOSE 4,6-DEHYDRATASE nearly identical to *Mycobacterium tuberculosis* rhamnose biosynthesis protein (previously rfbB, now known as rmlB) gene. FASTA results: Q50556 RHAMNOSE BIOSYNTHESIS PROTEIN ((rmlB) | SCO0749 | putative dehydratase |
| BG10619 | SpsK | spore coat polysaccharide synthesis | Rv3266c | (MTCY71.08c), len: 304, rfbD, similar to eg STRL__STRGR P29781 didp-4-dehydrorhamnose reductase (304 aa), fasta scores, opt: 788, E( ): 0, (47.4% identity in 304 aa overlap) (rmlD) | SCO7194 | putative polysaccharide biosynthesis protein |
| BG10763 | SpoIIIE | DNA translocase required for chromosome partitioning through the septum into the forespore | Rv2748c | (MTV002.13c), len: 883 aa. Possible ftsK, member of the spoIIIE/ftsK family; similar in C-terminal half to SP3E__BACSU P21458 stage iii sporuation protein e (787 aa), fasta scores; opt: 1294 z-score: 1488.5 E( ): 0, 50.9% identity in 485 aa overlap, and (ftsK) | SCO5750 | ftsK homolog |
| BG10765* | SpoOA | two-component response regulator central for the initiation of sporulation | Rv1033c | hypothetical protein | SCO2013 | putative two-component system response regulator |
| BG11039 | SpoVK | disruption leads to the production of immature spores | Rv0282 | hypothetical proiein | SCO1024 | conserved hypothetical protein |
| BG11197 | CgeE | maturation of the outermost layer of the spore | RV2747 | hypothetical profein | | |
| BG11231 | KipI | inhibitor of KinA | Rv0254c | hypothetical protein | SCO0442 | conserved hypothetical protein |
| BG11381 | CotSA | spore coat protein | Rv0486 | hypothetical protein | SCO2132<br>SCO4204 | putative glycosyl transferaseputative glycosyltransferase |
| BG11687 | YqgT | unknown; similar to gamma-D-glutamyl-L-diamino acid endopeptidase I | | | SCO1948 | putative zinc-binding carboxypeptidase |
| BG11806 | Tlp | small acid-soluble spore protein (thioredoxin-like protein) | | | | |
| BG12181 | YdhD | unknown; similar to unknown proteins from *B. subtilis* | | | SCO1429 | chitinase (putative secreted protein) (chiD) |
| BG12229 | SpoQM | sporulation-control gene | | | SCO0247 | hypothetical protein |
| BG12358 | KapD | inhibitor of the KinA pathway to sporulation | | | SCO7397 | conserved hypothetical protein |
| BG13288 | YkuD | unknown; similar to unknown proteins | Rv0116c | hypothetical protein | | |
| BG13781 | SafA | morphogenetic protein associated with SpoVID | Rv1233c | hypothetical protein | | |
| BG13783 | YrbC | unknown; similar to spore coat protein | Rv2603c | hypothetical protein | SCO1521 | conserved hypothetical protein |

TABLE 3-continued

| Table 3: Functional annotations for putative sporulation gene orthologues of *B. subtilis* in *Mycobacterium* spp. and *S. Coelicolor* | | | | | | |
|---|---|---|---|---|---|---|
| BG13907 | YtpT | unknown; simitar to DNA translocase stage III sporulation protein (SpoIIIE) | | | | |
| BG14193 | KipA | antagonist of KipI | Rv0263c | hypothetical protein | SCO0443 | conserved hypothetical protein |
| 8G14195 | SpsL | spore coat polysaccharide synthesis | Rv3465 | (MTCY13E12.16), len: 202. rmlC. Probable dtdp-4-dehydrorhamnose 3,5-epimerase. Nearly identical to *M. tuberculosis* sp\|O33170\|O33170 RMLC PROTEIN (203 aa) opt: 1171 z-score; 1465.1 E( ): 0; 89.5% identity in 200 aa overlap. Previously known as rfbC, FASTA (rmlC) | SCO0400 | putative epimerase |

TABLE 4

Table 4: Functional annotations for putative sporulation gene orthologues of *S. coelicolor* in *Mycobacterium* spp. and *B. subtilis*

| *S. coelicolor* A3(2) | | | *M. marinum* | | *M. tuberculosis* CDC1551 | |
|---|---|---|---|---|---|---|
| Gene id | Gene name | Annotation | Putative ortholog | Annotation | Putative ortholog | Annotation |
| SCO0506 | nadE2 | NH(3)-dependent NAD(+)syntnetase (nadE1) | | | | |
| SCO1024 | SCG20A.04 | conserved hypothetical protein | MM0541 | undefined product | | |
| SCO1177 | SCG11A.08 | putative gntR-famly transcriptional regulator | | | MT_0514 | transcriptional regulator, GntR family |
| SCO1434 | SC6D7.05c | putative CbxX/CfqX family protein | MM5443 | undefined product | MT_3981 | ATPase, AAA family |
| SCO1772 | SCIS1.12c | putative partitioning or sporulation protein | MM2523 | undefined product | MT_1749 | Soj family protein |
| SCO1950 | SCC54.10c | hypothetical protein | MM2230 | undefined product | MT_1466 | conserved hypothetical protein |
| SCO2083 | ftsQ | sporulation protein | MM3191 | undefined product | MT_2210 | cell division protein FtsQ (ftsQ) |
| SCO2085 | ftsW | putative cell division protein | MM3194 | undefined product | MT_2213 | cell division protein FtsW (ftsW-2) |
| SCO2607 | sfr | Sfr protein | | | | |
| SCO2805 | 2SCC13.13 | conserved hypothetical protein | | | MT_1099 | hypothetical protein |
| SCO3034 | whiB | sporulation regulatory protein | MM1282 | undefined product | MT_3358 | WhiB-related protein |
| SCO3579 | SCH17.13c | putative regulatory protein | MM5170 | undefined product | MT_3783 | WhiB-related protein |
| SCO3846 | SCH69.16 | putative FtsW/RodA/SpoVE family cell cycle protein | MM0019 | undefined product | MT_0020 | cell division protein FtsW (ftsW-1) |
| SCO3883 | StH24.05 | putative membrane protein | MM5485 | undefined product | MT_4040 | conserved hypothetical protein |
| SCO3886 | S1H24.08 | putative partitioning or sporulation protein | MM5482 | undefined product | MT_4037 | Soj family protein |
| SCO3887 | StH24.09 | putative partitioning or speculation protein | MM5481 | undefined product | MT_4036 | ParB family protein |
| SCO3934 | SCQ11.17 | ftsK/spoIIIE family protein 4328870: 4330171 forward MW: 45953 | MM3126 | undefined product | | |
| SCO4767 | SC6G4.45c | putative regulatory protein | MM1132 | undefined product | MT_3525 | WhiB-related protein |
| SCO5302 | SC6G9.31 | putative integral membrane cell-cycle protein | MM0019 | undefined product | MT_0020 | cell division protein FtsW (ftsW-1) |

TABLE 4-continued

Table 4: Functional annotations for putative sporulation gene orthologues of *S. coelicolor* in *Mycobacterium* spp. and *B. subtilis*

| | | | | | | |
|---|---|---|---|---|---|---|
| SCO5320 | SC6G9.13 | whiE protein I | | | | |
| SCO5321 | SC6G9.12c | polyketide hydroxylase | MM3384 | undefined product | | |
| SCO5621 | whiG | RNA polymerase sigma factor WhiG | | | | |
| SCO5633 | traSA | integrase fusion protein | | | MT__2962 | tyrosine recombinase XerC (xerC) |
| SCO5750 | SC7C7.05 | ftsK homolog | MM1967 | undefined product | MT__2819 | cell division protein FtsK (ftsK) |
| SCO6435 | SC9B5.02 | hypothetical protein | MM4895 | undefined product | | |

| *S. coelicolor* A3(2) | | | *M. tuberculosis* H37Rv | | *B. subtilis* 168 | |
|---|---|---|---|---|---|---|
| Gene id | Gene name | Annotation | Putative ortholog | Annotation | Putative ortholog | Annotation |
| SCO0506 | nadE2 | NH(3)-dependent NAD(+)syntnetase (nadE1) | | | BG10694 | NadE: NH3-dependent NAD* synthetase |
| SCO1024 | SCG20A.04 | conserved hypothetical protein | | | BG11039 | SpoVK: disruption leads to the production of immature spores |
| SCO1177 | SCG11A.08 | putative gntR-famly transcriptional regulator | Rv0494 | hypothetical protein | | |
| SCO1434 | SC6D7.05c | putative CbxX/CfqX family protein | RV3868 | hypothetical protein | | |
| SCO1772 | SCI51.12c | putative partitioning or sporulation protein | Rv1708 | hypothetical protein | | |
| SCO1950 | SCC54.10c | hypothetical protein | Rv1423 | hypothetical protein | BG12402 | YvcL: unknown; similar to unknown proteins |
| SCO2083 | ftsQ | sporulation protein | Rv2151c | (MTCY270.17), len: 314. Function ftsQ: possible cell division protein, some homology to FTSQ__STRGR P45503 cell division protein ftsq homolog (208 aa), fasta scores; opt: 204 z-score: 217.5 E( ): 4e−05; (30.6% identity in 193 aa overlap) (ftsQ) | | |
| SCO2085 | ftsW | putative cell division protein | Rv2154c | (MTCY270.14), len: 524. ftsW, probable cell division protein FtsW, related to MTCY10H4.17c, 3.2e−17. FASTA best SP5E__BACSU P07373 stage v sporulation protein e(366 aa) opt: 755 z-score: 727.2 E( ): 1.6e−33; (38.4% identity in 357 aa overlap) (ftsW) | | |
| SCO2607 | sfr | Sfr protein | | | BG10226 | SpoVE: required for spore cortex peptidoglycan synthesis |
| SCO2805 | 2SCC13.13 | conserved hypothetical protein | Rv1069c | hypothetical protein | | |
| SCO3034 | whiB | sporulation regulatory protein | Rv3260c | (MTV015.05c), len: 89. whiB, Probable regulatory protein very similar to *S. griseocarneum* WhiB SGWHIB__1 (87 aa) and | | |

TABLE 4-continued

Table 4: Functional annotations for putative sporulation gene orthologues of *S. coelicolor* in *Mycobacterium* spp. and *B. subtilis*

| | | | | | | |
|---|---|---|---|---|---|---|
| | | | | other *Streptomyces* and mycobacterial WhiB homologues. Start chosen by homology but orf continues to ATG upstream at 3754. FASTA scores: gp (whiB2) | | |
| SCO3579 | SCH17.13c | putative regulatory protein | Rv3681c | (MTV025.029c), len: 100. Probable regulatory protein, similar to many e.g. gp\|X62287\|SCWHIB_1 *S. coelicolor* whiBgene (87 aa), FASTA scores: opt: 237 z-score: 332.1 E(): 5.5e−11; 45.2% identity in 73 aa overlap. Also similar to several mycobacterial putativ (whiB4) | | |
| SCO3846 | SCH69.16 | putative FtsW/RodA/SpoVE family cell cycle protein | Rv0017c | (MTCY10H4.17c), len: 469, highly similar to *M. leprae* MLCB1770_12, (465 aa), opt: 2475 z-score: 3029.6E( ): 0; E235744 cell division protein, (81.9% identity in 469 aa overlap). Also similar to MTCY270_14, (524, 32.2% identity in 369 aa overlap) (rodA) | | |
| SCO3883 | StH24.05 | putative membrane protein | Rv3921c | hypothetical protein | BG10062 | SpoIIIJ: essential for sigma-G activity at stage III |
| SCO3886 | S1H24.08 | putative partitioning or sporulation protein | Rv3918c | (MTV028.09c), len: 347. Unknown, similar to TR: 005189(EMBL: U87804) CHROMOSOME PARTITIONING PROTEIN PARA from *CAULOBACTER CRESCENTUS* (266 aa), fasta scores; opt: 787 z-score: 990.9 E( ): 0, 50.6% identity in 261 aa overlap and to SOJ_BACSU P37522 soj protei (parB) | BG10055 | Soj: centromere-like function involved in forespore chromosome partitioning/ negative regulation of sporulation initiation |
| SCO3887 | StH24.09 | putative partitioning or speculation protein | Rv3917c | (MTV028.08c), len: 344, Unknown, similar to TR: 005190 CHROMOSOME PARTITIONING PROTEIN PARB from *CAULOBACTER CRESCENTUS* (293 aa), fasta scores; opt: 564 z-score: 784.2 E( ): 0, 38.6% identity in 308 aa overlap; and to SPOJ_BACSU P26497 stage 0 sporulation pr (parA) | BG10054 | SpoOJ: chromosome positioning near the pole and transport through the polar septum/ antagonist of Soj-dependent inhibition of sporulation initiation |
| SCO3934 | SCQ11.17 | ftsK/spoIIIE family protein 4328870: 4330171 forward MW: 45953 | | | | |

TABLE 4-continued

Table 4: Functional annotations for putative sporulation gene orthologues of *S. coelicolor* in *Mycobacterium* spp. and *B. subtilis*

| | | | | | | |
|---|---|---|---|---|---|---|
| SCO4767 | SC6G4.45c | putative regulatory protein | Rv3416 | (MTCY7B.13c), len: 102. whiB, regulatory protein, highly similar to U00020_2 *Mycobacterium leprae* cosmid B229 and *M. leprae* U00015_26 cosmid B1620(102 aa) opt: 657, z-score: 807.1, E( ): 0, (86.3% identity in 102 aa overlap) (whiB3) | | |
| SCO5302 | SC6G9.31 | putative integral membrane cell-cycle protein | Rv0017c | (MTCY10H4.17c), len: 469, highly similar to *M. leprae* MLCB1770_12, (465 aa), opt: 2475 z-score: 3029.6E( ): 0; E235744 cell division protein, (81.9% identity in 469 aa overlap). Also similar to MTCY270_14, (524, 32.2% identity in 369 aa overlap) (rodA) | | |
| SCO5320 | SC6G9.13 | whiE protein I | | | BG12784 | YczJ: unknown; similar to unknown proteins |
| SCO5321 | SC6G9.12c | polyketide hydroxylase | | | | |
| SCO5621 | whiG | RNA polymerase sigma factor WhiG | | | BG10751 | SigD: RNA polymerase flagella, motility, chemotaxis and autolysis sigma factor |
| SCO5633 | traSA | integrase fusion protein | Rv2894c | (MTCY274,25c), len: 298. xerC, integrase/recombinase, most similar to XERC_HAEIN P44818 integrase/recombinase xerc, (295 aa), opt: 627, z-score: 726.6, E( ): 6.3e−34, (39.9% identity in 296 aa overlap). *M. leprae* equivalent is sp\|O33037\|O33037 XERC PROTE (xerC) | BG12099 | YdcL: unknown; similar to integrase |
| SCO5750 | SC7C7.05 | ftsK homolog | Rv2748c | (MTV002.13c), len: 883 aa. Possible ftsK, member of the spoIIIE/ftsK family; similar in C-terminal half to SP3E_BACSU P21458 stage iii sporulation protein e (787 aa), fasta scores; opt: 1294 z-score: 1488.5 E( ): 0, 50.9% identity in 485 aa overlap, and (ftsK) | BG10763 | SpoIIIE; DNA translocase required for chromosome partitioning through the septum into the forespore |
| SCO6435 | SC9B5.02 | hypothetical protein | | | | |

It is also contemplated that the immunogenic peptides can be derived from homologues of the above mentioned proteins from other Mycobacteria, e.g. *M. tuberculosis, M. leprae, M. bovis, M. avium, M. microti, M. intracellulare, M. paratuberculosis, M. ulcerans*, or *M. africanum.*

Immunogenic fragments typically have a sequence of at least 3, 5, 6, 10 or 20 contiguous amino acids from a natural peptide.

Analogs include allelic, species and induced variants. Analogs typically differ from naturally occurring peptides at one or a few positions, often by virtue of conservative substitutions. Analogs typically exhibit at least 80% or 90% sequence identity with natural peptides. Some analogs also include unnatural amino acids or modifications of N or C terminal amino acids. Examples of unnatural amino acids are a, a-disubstituted amino acids, N-alkyl amino acids, lactic acid, 4-hydroxyproline, -carboxyglutamate, e-N,N,N-trimethyllysine, e-N-acetyllysine, O-phosphoserine, N-acetylserine, N-formylmethionine, 3-methylhistidine, 5-hydroxylysine, -N-methylarginine.

Fragments and analogs can be screened for prophylactic or therapeutic efficacy in disease models as described below.

A protein chosen from one of those encoded by one of the genes in Tables 1-4, their fragments, analogs and spore forming peptides can be synthesized by solid phase peptide synthesis or recombinant expression, or can be obtained from natural sources. Automatic peptide synthesizers are commercially available from numerous suppliers, such as Applied Biosystems, Foster City, Calif. Recombinant expression can be in bacteria, such as *E. coli*, yeast, insect cells or mammalian cells. Procedures for recombinant expression are described by Sambrook et al., Molecular Cloning: A Laboratory Manual (C. S. H. P. Press, NY 2d ed., 1989).

Therapeutic agents also include longer polypeptides that include, for example, an spore forming peptide, active fragment or analog together with other amino acids. Therapeutic agents also include multimers of monomeric immunogenic agents.

In a further variation, an immunogenic peptide can be presented as a viral or bacterial vaccine. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of a bacteria so that the peptide is displayed. Viruses or bacteria used in such methods should be nonpathogenic or attenuated. Suitable viruses include adenovirus, HSV, vaccinia and fowl pox. Fusion of an immunogenic peptide to HBsAg of HBV is particularly suitable.

Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980.

Combinatorial libraries and other compounds are initially screened for suitability by determining their capacity to bind to antibodies or lymphocytes (B or T) known to be specific for spore forming peptides. For example, initial screens can be performed with any polyclonal sera or monoclonal antibody to a spore forming peptide.

Compounds identified by such screens are then further analyzed for capacity to induce antibodies or reactive lymphocytes to a spore forming peptide. For example, multiple dilutions of sera can be tested on microtiter plates that have been precoated with a spore forming peptide and a standard ELISA can be performed to test for reactive antibodies to a spore forming peptide. Compounds can then be tested for prophylactic and therapeutic efficacy in animal models Therapeutic agents of the invention also include antibodies that specifically bind to a spore forming peptide. Such antibodies can be monoclonal or polyclonal. The production of non-human monoclonal antibodies, e.g., murine or rat, can be accomplished by, for example, immunizing the animal with a spore forming peptide. See Harlow & Lane, Antibodies, A Laboratory Manual (CSHP NY, 1988) (incorporated by reference for all purposes). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., Proc. Natl. Acad. Sci. USA 86, 10029-10033 (1989) and WO 90/07861 (incorporated by reference for all purposes).

Human antibodies can be obtained using phage-display methods. See, e.g., Dower et al., WO 91/17271; McCafferty et al., WO 92/01047. In these methods, libraries of phage are produced in which members display different antibodies on their outersurfaces. Antibodies are usually displayed as Fv or Fab fragments. Phage displaying antibodies with a desired specificity are selected by affinity enrichment to a spore forming peptide, or fragments thereof. Human antibodies against a spore forming peptide can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991) (each of which is incorporated by reference in its entirety for all purposes). Human antibodies can be selected by competitive binding experiments, or otherwise, to have the same epitope specificity as a particular mouse antibody. Such antibodies are particularly likely to share the useful functional properties of the mouse antibodies.

Human polyclonal antibodies can also be provided in the form of serum from humans immunized with an immunogenic agent.

Optionally, such polyclonal antibodies can be concentrated by affinity purification using a spore forming peptide as an affinity reagent.

Human or humanized antibodies can be designed to have IgG, IgD, IgA and IgE constant region, and any isotype, including IgG1, IgG2, IgG3 and IgG4. Antibodies can be expressed as tetramers containing two light and two heavy chains, as separate heavy chains, light chains, as Fab, Fab'F (ab')2, and Fv, or as single chain antibodies in which heavy and light chain variable domains are linked through a spacer.

Therapeutic agents for use in the present methods also include T-cells that bind to a spore forming peptide. For example, T-cells can be activated against a spore forming peptide by expressing a human MHC class I gene and a human β-2-microglobulin gene from an insect cell line, whereby an empty complex is formed on the surface of the cells and can bind to a spore forming peptide. T-cells contacted with the cell line become specifically activated against the peptide. See Peterson et al., U.S. Pat. No. 5,314,813. Insect cell lines expressing an MHC class II antigen can similarly be used to activate CD4 T cells.

Some agents for inducing an immune response contain the appropriate epitope for inducing an immune response against a spore coating peptide but are too small to be immunogenic. In this situation, a peptide immunogen can be linked to a suitable carrier to help elicit an immune response. Suitable carriers include serum albumins, keyhole limpet hemocyanin, immunoglobulin molecules, thyroglobulin, ovalbumin, tetanus toxoid, or a toxoid from other pathogenic bacteria, such as diphtheria, *E. coli*, cholera, or *H. pylori*, or an attenuated toxin derivative. Other carriers for stimulating or enhancing an immune response include cytokines such as IL-1, IL-1a and peptides, IL-2, zINF, IL-10, GM-CSF, and chemokines, such as MIPla and 0 and RANTES. Immunogenic agents can also be linked to peptides that enhance transport across tissues, as described in O'Mahony, WO 97/17613 and WO 97/17614.

Immunogenic agents can be linked to carriers by chemical crosslinking. Techniques for linking an immunogen to a carrier include the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the s-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid.

The carboxyl groups can be activated by combining them with succinimide or 1-hydroxyl-2-nitro-4-sulfonic acid, sodium salt.

Immunogenic peptides can also be expressed as fusion proteins with carriers. The immunogenic peptide can be linked at the amino terminus, the carboxyl terminus, or internally to the carrier. Optionally, multiple repeats of the immunogenic peptide can be present in the fusion protein.

Immune responses against spore forming peptides can also be induced by administration of nucleic acids encoding a spore forming peptide. Such nucleic acids can be DNA or RNA. A nucleic acid segment encoding the immunogen is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector.

A number of viral vector systems are available including retroviral systems (see, e.g., Lawrie and Tumin, Cur. Opin. Genet. Develop. 3, 102-109 (1993)); adenoviral vectors (see, e.g., Bett et al., J. Virol. 67, 5911 (1993)); adeno-associated virus vectors (see, e.g., Zhou et al., J. Exp. Med. 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), and papillomaviruses (Ohe et al., Human Gene Therapy 6, 325-333 (1995); Woo et al., WO 94/12629 and Xiao & Brandsma, Nucleic Acids. Res. 24, 2630-2622 (1996)).

DNA encoding an immunogen, or a vector containing the same, can be packaged into liposomes. Suitable lipids and related analogs are described by U.S. Pat. No. 5,208,036, U.S. Pat. No. 5,264,618, U.S. Pat. No. 5,279,833 and U.S. Pat. No. 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., J. Micro Encap. (1996).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346). DNA can also be administered using a gene gun. See Xiao & Brandsma, supra. The DNA encoding an immunogen is precipitated onto the surface of microscopic metal beads. The microprojectiles are accelerated with a shock wave or expanding helium gas, and penetrate tissues to a depth of several cell layers. For example, The Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see WO 95/05853).

Patients amenable to treatment include individuals at risk of disease but not showing symptoms, as well as patients presently showing symptoms.

Therefore, the present methods can be administered prophylactically to the general population without any assessment of the risk of the subject patient. The present methods are especially useful for individuals who do have a known risk of being inflicted by a *Mycobacterium* infection. Such individuals include those having a weakened immune system.

In prophylactic applications, pharmaceutical compositions or medicants are administered to a patient susceptible to, or otherwise at risk of, a particular disease in an amount sufficient to eliminate or reduce the risk or delay the outset of the disease. In therapeutic applications, compositions or medicants are administered to a patient suspected of, or already suffering from such a disease in an amount sufficient to cure, or at least partially arrest, the symptoms of the disease and its complications. An amount adequate to accomplish this is defined as a therapeutically- or pharmaceutically-effective dose. In both prophylactic and therapeutic regimes, agents are usually administered in several dosages until a sufficient immune response has been achieved. Typically, the immune response is monitored and repeated dosages are given if the immune response starts to fade.

Effective doses of the compositions of the present invention, for the treatment of the above described conditions can vary depending upon many different factors, including means of administration, target site, physiological state of the patient, whether the patient is human or an animal, other medications administered, and whether treatment is prophylactic or therapeutic. Usually, the patient is a human, but the patient can be a nonhuman mammal, such as bovine. Treatment dosages need to be titrated to optimize safety and efficacy. The amount of immunogen depends on whether adjuvant is also administered, with higher dosages being required in the absence of adjuvant. The amount of an immunogen for administration sometimes can vary from 1 μg-500 μg per patient and more usually from 5-500 μg per injection for human administration. Occasionally, a higher dose of 0.5-5 mg per injection can be used. Typically about 10, 20, 50 or 100 μg is used for each human injection. The timing of injections can vary significantly from once a day, to once a year, to once a decade. On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster injections at 6 weekly intervals. Another regimen consists of an immunization followed by booster injections 1, 2 and 12 months later. Another regimen entails an injection every two months for life. Alternatively, booster injections can be on a regular or irregular basis as indicated by monitoring the immune response.

For passive immunization with an antibody, the dosage can range from about 0.0001 to 100 mg/kg, and more usually 0.01 to 5 mg/kg of the host body weight. Doses for nucleic acids encoding immunogens can range from about 10 ng to 1 g, 100 ng to 100 mg, 1 μg to 10 mg, or 30-300 μg DNA per patient. Doses for infectious viral vectors can vary from 10-100 virions or more per dose.

Agents for inducing an immune response can be administered by parenteral, topical, intravenous, oral, subcutaneous, intraperitoneal, intranasal or intramuscular means for prophylactic and/or therapeutic treatment. The most typical route of administration is subcutaneous although others can be equally effective. The next most common is intramuscular injection. This type of injection is most typically performed in the arm or leg muscles. Intravenous injections as well as intraperitoneal injections, intraarterial, intracranial, or intradermal injections are also effective in generating an immune response. In some methods, agents are injected directly into a particular tissue where deposits have accumulated.

Immunogenic agents of the invention, such as peptides, are sometimes administered in combination with an adjuvant. A variety of adjuvants can be used in combination with a spore forming peptide, to elicit an immune response. Preferred adjuvants augment the intrinsic response to an immunogen without causing conformational changes in the immunogen that affect the qualitative form of the response. Preferred adjuvants include alum, 3 de-O-acylated monophosphoryl lipid A (MPL) (see GB 2220211). QS21 is a triterpene glycoside or saponin isolated from the bark of the Quillaja Saponaria Molina tree found in South America (see Kensil et al., in Vaccine Design: The Subunit and Ajuvant Approach (eds. Powell & Newman, Plenum Press, NY, 1995); U.S. Pat. No. 5,057,540). The spore forming peptides according to the invention are themselves hydrophobic and may also be used as adjuvants.

Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Alternatively, spore forming peptide can be coupled to an adjuvant. For example, a lipopeptide version of spore forming peptide can be prepared by coupling palmitic acid or other lipids directly to the N-terminus of spore forming peptide as described for hepatitis B antigen vaccination (Livingston, J. Immunol. 159, 1383-1392 (1997)). However, such coupling should not substantially change the conformation of spore forming peptide so as to affect the nature of the immune response thereto. Adjuvants can be administered as a component of a therapeutic composition with an active agent or can be administered separately, before, concurrently with, or after administration of the therapeutic agent.

A preferred class of adjuvants is aluminum salts (alum), such as aluminum hydroxide, aluminum phosphate, aluminum sulfate. Such adjuvants can be used with or without other specific immunostimulating agents such as MPL or 3-DMP, QS21, polymeric or monomeric amino acids such as polyglutamic acid or polylysine. Another class of adjuvants is oil-in-water emulsion formulations. Such adjuvants can be used with or without other specific immunostimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalane, 0.4% Tween 80, 5% pluronic-blocked polymer L121, and thr-MDP, either microfluidized into a submicron emulsion or vortexed to generate a larger particle size emulsion, and (c) Ribi adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox).

Another class of preferred adjuvants is saponin adjuvants, such as Stimulons (QS21, Aquila, Worcester, Mass.) or particles generated therefrom such as ISCOMs (immunostimulating complexes) and ISCOMATRIX. Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), tumor necrosis factor (TNF).

An adjuvant can be administered with an immunogen as a single composition, or can be administered before, concurrent with or after administration of the immunogen. Immunogen and adjuvant can be packaged and supplied in the same vial or can be packaged in separate vials and mixed before use. Immunogen and adjuvant are typically packaged with a label indicating the intended therapeutic application. If immunogen and adjuvant are packaged separately, the packaging typically includes instructions for mixing before use. The choice of an adjuvant and/or carrier depends on the stability of the vaccine containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. Alum, MPL and QS21 are preferred. Optionally, two or more different adjuvants can be used simultaneously. Preferred combinations include alum with MPL, alum with QS21, MPL with QS21, and alum, QS21 and MPL together. Also, Incomplete Freund's ajuvant can be used (Chang et al., Advanced Drug Delivery Reviews 32, 173-186 (1998)), optionally in combination with any of alum, QS21, and MPL and all combinations thereof.

Agents of the invention can be administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. However, some reagents suitable for administration to animals, such as Complete Freund's adjuvant are not typically included in compositions for human use.

Pharmaceutical compositions can also include large, slowly metabolized macromolecules such as proteins, polysaccharides, polylactic acids, polyglycolic acids and copolymers (such as latex functionalized sepharose, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier which can be a sterile liquid such as water, oils, saline, glycerol, or ethanol.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Typically, compositions can be prepared as injectables, either as liquid solutions or suspensions; solid forms suitable for solution in, or suspension in, liquid vehicles prior to injection can also be prepared. The preparation can also be emulsified or encapsulated in liposomes or micro particles such as polylactide, polyglycolide, or copolymer for enhanced adjuvant effect, as discussed above (see Langer, Science 249, 1527 (1990) and Hanes, Advanced Drug Delivery Reviews 28, 97-119 (1997). The agents of the invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5 k to 10 k, preferably 1%-2%. Oral formulations include excipients, such as pharmaceutical grades of mannitol, lactose, starch, magnesium stearate, sodium saccharine, cellulose, and magnesium carbonate. These compositions can take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391, 851 (1998)). Co-administration can be achieved by using the components as a mixture or as linked molecules obtained by chemical crosslinking or expression as a fusion protein.

Alternatively, transdermal delivery can be achieved using a skin path or using transferosomes (Paul et al., Eur. J. Immunol. 25, 3521-24 (1995); Cevc et al., Biochem. Biophys. Acta 1368, 201-15 (1998)).

The invention provides methods of detecting an immune response against a spore forming peptide in a patient suffering from or susceptible a disease caused by a *Mycobacterium*. The methods are particularly useful for monitoring a course of treatment being administered to a patient. The methods can be used to monitor both therapeutic treatment on symptomatic patients and prophylactic treatment on asymptomatic patients.

Some methods entail determining a baseline value of an immune response in a patient before administering a dosage of agent, and comparing this with a value for the immune response after treatment. A significant increase (i.e., greater than the typical margin of experimental error in repeat measurements of the same sample, expressed as one standard deviation from the mean of such measurements) in value of the immune response signals a positive treatment outcome (i.e., that administration of the agent has achieved or augmented an immune response). If the value for immune response does not change significantly, or decreases, a negative treatment outcome is indicated. In general, patients undergoing an initial course of treatment with an agent are expected to show an increase in immune response with successive dosages, which eventually reaches a plateau. Administration of agent is generally continued while the immune response is increasing.

Attainment of the plateau is an indicator that the administered of treatment can be discontinued or reduced in dosage or frequency.

In other methods, a control value (i.e., a mean and standard deviation) of immune response is determined for a control population. Typically the individuals in the control population have not received prior treatment. Measured values of immune response in a patient after administering a therapeutic agent can then be compared with the control value. A significant increase relative to the control value (e.g., greater than one standard deviation from the mean) signals a positive treatment outcome. A lack of significant increase or a decrease signals a negative treatment outcome.

Administration of agent is generally continued while the immune response is increasing relative to the control value.

As before, attainment of a plateau relative to control values is an indicator that the administration of treatment can be discontinued or reduced in dosage or frequency.

In other methods, a control value of immune response (e.g., a mean and standard deviation) can be determined from a control population of individuals who have undergone treatment with a therapeutic agent and whose immune responses have plateaued in response to treatment. Measured values of immune response in a patient are compared with the control value. If the measured level in a patient is not significantly different (e.g., more than one standard deviation) from the control value, treatment can be discontinued. If the level in a patient is significantly below the control value, continued administration of agent is warranted. If the level in the patient persists below the control value, then a change in treatment regime, for example, use of a different adjuvant may be indicated.

In other methods, a patient who is not presently receiving treatment but has undergone a previous course of treatment is monitored for immune response to determine whether a resumption of treatment is required. The measured value of immune response in the patient can be compared with a value of immune response previously achieved in the patient after a previous course of treatment. A significant decrease relative to the previous measurement (i.e., greater than a typical margin of error in repeat measurements of the same sample) is an indication that treatment can be resumed. Alternatively, the value measured in patient can be compared with a control value (mean plus standard deviation) determined in population of patients after undergoing a course of treatment.

Alternatively, the measured value in a patient can be compared with a control value in populations of prophylactically treated patients who remain free of symptoms of disease, or populations of therapeutically treated patients who show amelioration of disease characteristics. In all of these cases, a significant decrease relative to the control level (i.e., more than a standard deviation) is an indicator that treatment should be resumed in a patient.

The tissue sample for analysis is typically blood, plasma, serum, mucus or cerebral spinal fluid from the patient. The sample is analyzed for indicia of an immune response to any form of a spore forming peptide, typically SpoVK, CotSA, YrbC, SpoVE, Soj, and SpoIIIE. The immune response can be determined from the presence of, e.g., antibodies or T-cells that specifically bind to such a peptide. ELISA methods of detecting antibodies specific to a spore forming peptide are described in the Examples section. Methods of detecting reactive T-cells have been described above (see Definitions).

The invention further provides diagnostic kits for performing the diagnostic methods described above. Such diagnostic methods include detecting the presence of Mycobacteria in patients, food products and in the environment, such as in fish or poultry farms. Typically, kits for such diagnosis or detection contain an agent that specifically binds to antibodies to a spore forming peptide or reacts with T-cells specific for a spore forming peptide. The kit can also include a label. For detection of antibodies to a spore forming peptide, the label is typically in the form of labelled anti-idiotypic antibodies. For detection of antibodies, the agent can be supplied prebound to a solid phase, such as to the wells of a microtiter dish. For detection of reactive T-cells, the label can be supplied as $^{3}$H-thymidine to measure a proliferative response. Kits also typically contain labelling providing directions for use of the kit. The labelling may also include a chart or other correspondence regime correlating levels of measured label with levels of antibodies to a spore forming peptide or T-cells reactive with a spore forming peptide. The term labelling refers to any written or recorded material that is attached to, or otherwise accompanies a kit at any time during its manufacture, transport, sale or use. For example, the term labelling encompasses advertising leaflets and brochures, packaging materials, instructions, audio or video cassettes, computer discs, as well as writing imprinted directly on kits.

The binding molecules described herein may be used as diagnostic tools within the field of human and veterinary medicine.

To summarize, the invention provides:

A binding molecule which is capable of binding to a peptide chosen from the group consisting of SEQ ID NO: 2, 4, 6, 8, 10, 12, 14, 16, 18, 20, 22, 24, and 26, for use as a medicament.

In one embodiment of the invention, the binding molecule is for use in treating, diagnosing or preventing a disease caused by a *Mycobacterium.*

In one embodiment of the invention, the binding molecule is for treating, diagnosing or preventing a disease caused by a *Mycobacterium*, wherein the disease is tuberculosis, leprosy, Johns disease, Crohn's disease, or a disease caused by a non-tuberculous *Mycobacterium.*

Furthermore, the invention provides an agent effective to induce an immunogenic response against a spore forming peptide, or an antibody thereto, for use as a medicament.

In one embodiment of the invention, the agent effective to induce an immunogenic response against a spore forming peptide, or an antibody thereto, is a peptide chosen from the group consisting of SEQ ID NO: 2, 4, 6, 8, 10, 12, 14, 16, 18, 20, 22, 24, and 26, or a binding molecule capable of binding thereto.

In one embodiment of the invention, an agent effective to induce an immunogenic response against a spore forming peptide, or an antibody thereto, is for treating or preventing a disease caused by a *Mycobacterium.*

In one embodiment of the invention, an agent effective to induce an immunogenic response against a spore forming peptide, or an antibody thereto, is for treating or preventing a disease selected from tuberculosis, leprosy, Johnes disease, Crohn's disease, or a disease caused by a non-tuberculous *Mycobacterium.*

In another aspect the invention provides pharmaceutical composition comprising an agent effective to induce an immunogenic response against a spore forming peptide, or an antibody thereto, in a patient, and a pharmaceutically acceptable adjuvant.

Furthermore, the invention provides a pharmaceutical composition according to the above, wherein the agent comprises a spore forming peptide or an active fragment thereof.

Furthermore, the invention provides a pharmaceutical composition as defined herein above, wherein the agent is chosen from the group consisting of SEQ ID NO: 2, 4, 6, 8, 10, 12, 14, 16, 18, 20, 22, 24, and 26, or an antibody thereto.

Furthermore, the invention provides a pharmaceutical composition as defined herein above, wherein the spore forming peptide is chosen from the group comprising CotA, CotD, CotT, CotSA, and YrbC.

Furthermore, the invention provides a pharmaceutical composition according to the above, for use as a medicament.

In another aspect, the invention provides a pharmaceutical composition according to the above, for treating or preventing a disease caused by a *Mycobacterium.*

In yet another aspect, the invention provides a method of preventing or treating a Mycobacterial infection in a patient, comprising: administering an agent effective to induce an immune response against a peptide component of an spore coating of a *Mycobacterium* in a mammal.

Furthermore, the invention provides a method according to the above wherein the patient is a human.

Furthermore, the invention provides a method according to the above, wherein the disease is tuberculosis, leprosy, Johnes disease, Crohns disease, or a disease caused by non-tuberculosous Mycobacteria.

Furthermore, the invention provides a method according to the above, wherein the agent comprises a spore forming peptide or an active fragment thereof.

Furthermore, the invention provides a method according to the above, wherein the spore forming peptide is chosen from the group comprising CotA, CotD, CotT, CotSA, YrbC.

Furthermore, the invention provides a method according to the above, wherein the immune response comprises antibodies that bind to the spore forming peptide.

In another aspect, the invention provides a kit comprising a binding molecule which is capable of binding to a peptide chosen from the group consisting of SEQ ID NO: 2, 4, 6, 8, 10, 12, 14, 16, 18, 20, 22, 24, and 26, and instructions for use.

The kit may be used to detect the presence of Mycobacteria in various samples, such as samples taken from animals, or from the environment around animals, such as from fish or poultry farms.

EXAMPLES

Strains, Media and Growth Conditions

*Mycobacterium marinum* T CCUG 20998 (ATCC 927) was grown at 30° C. on 7H10 agar plates supplemented with 0.5% glycerol, 10% OADC (oleic acid-albumin-dextrose complex), and 0.01% cycloheximide. *Mycobacterium bovis* BCG was grown at 37° C. on 7H10 agar plates supplemented with 0.5% Tween 80, 10% OADC, and 0.01% cycloheximide. The *Escherichia coli* K12 strain MG1655 (Maisnier-Patin, S., Dasgupta, S., Krabbe, M., Nordström, K. Conversion to bidirectional replication after unidirectional initiation from R1 plasmid origin integrated at oriC in *Escherichia coli. Mol. Microbiol.* 30, 1067-1079 (1998)) was grown in M9 media supplemented with 0.2% glucose and 0.2% casamino acids at 37° C.

Flow Cytometry

Cells were harvested at different growth times, fixed, stained, and run in the flow cytometer. The data analyzed as described previously (Maisnier-Patin, S., Dasgupta, S., Krabbe, M., Nordström, K. Conversion to bidirectional replication after unidirectional initiation from R1 plasmid origin integrated at oriC in *Escherichia coli. Mol. Microbiol.* 30, 1067-1079 (1998)). Briefly, the cells were fixed in 70% (final concentration) ice-cold ethanol and stored at 4° C. For flow cytometry, the fixed cells were washed with particle-free (passed through 0.2 micron nitrocellulose filters) 10 mM Tris-HCl (pH 7.9) buffer supplemented with 10 mM $MgCl_2$. The cells were subsequently resuspended into 0.1× vol of the same buffer. Washed cells were stained with ethidium bromide (0.4 μg/ml, final concentration) and mithramycin A (16 μg/ml, final concentration) and kept on ice for 30 min before flow cytometry (Compact A440 analyser Unit, Apogee Flow Systems, in FIG. 10 BioRad Bryte HS was used). At least 20,000 cells were counted for each flow histogram.

Fluorescence and Phase Contrast Microscopy

The cells were collected and fixed as described above, washed with phosphate buffered saline (PBS) and spotted onto a thin layer of 1% agarose in 0.9% saline containing 0.5 μg/ml 4,6-diamidino-2-phenylindole (DAPI) on a microscope slide. A Zeiss (Axioplan 2) microscope with a CCD camera (AxioCam, Zeiss) linked to a computerized image analysis system (Program: Axiovision 4.3) was used for all microscopy. The filter used for DAPI fluorescence was D360/40 (360±20 nm). The phase and fluorescence images were superimposed using the program Axiovision 4.3.

Isolation of Pure Spores

Figure 6:
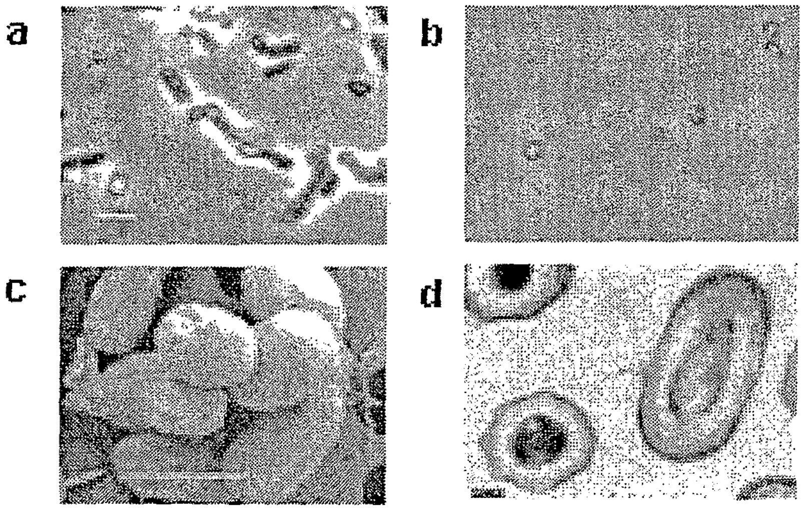

Pure *M. marinum* spores were isolated as described in previous methods, with slight variations (Lewis P. J., & Errington, J. *Mol. Microbiol.*, 25, 945-954 (1997), Long S. K., & Williams, O. B. *J. Bacteriol.* 76, 332 (1958), Powers, E. M., *Appl. Microbiol.* 16, 180-181 (1968)). Cells were collected and harvested as described above from two week (*M. marinum*) and six month old plates (*M. bovis* BCG), washed in 0.9% NaCl, and then resuspended in TE-buffer (10 mM Tris-HCl pH 7.9 and 1 mM EDTA). Silica beads (0.1 mm, Q-Biogene, Lysing matrix B) were added to the cells and shaken vigorously. The two suspensions were kept at 4° C. for 5 minutes to allow the glass beads to sediment. The supernatants were collected and then filtered through a sterile 2 micron filter (Millipore). The filtrate was centrifuged at 10,000 r.p.m., for 10 minutes at 4° C. The pellet was resuspended in TE-buffer and lysozyme was added to 3 mg/ml final and incubated at 37° C. for 1 hour. Then SDS was added to 6.25% (v/v final concentration) and incubated at 37° C. for at least 30 min. The lysate was centrifuged at 10,000 r.p.m., for 10 min at 4° C. The pellet was washed 5 times in sterile water at 4° C., and finally resuspended in sterile water. The presence of spores was verified microscopically (FIGS. 6 and 9).

Serial Dilution of Pure Spores to Isolate Single Spore Particle

The idea of serial dilution to isolate a single spore was based on a previous report (Lister, J., *Transactions of the Pathological Society of London* 29, 425-467 (1878)). A batch of isolated spores was split into two fractions; one was plated freshly and after a week of growth the colonies were counted to estimate the number of viable spore particles in the spore preparation. This number was of the order of $10^3$/ml. The other fraction was serially diluted $10^4$-fold such that there would be no more than one viable spore in each tube. The so obtained spore solutions were plated on 7H10 plates with necessary supplements (see above) and the plates were incubated at 30° C.

Scanning Electron Microscopy (SEM)

Samples for SEM were prepared as described previously (Lackner P. et al., *Malar J.* 5, 116 (2006). Briefly, cells were grown and collected as described above, fixed in 2.5% glutaraldehyde, washed 3× in 0.1 M PBS followed by fixation in 1% osmium tetraoxide. The fixed cells were washed 3× in 0.1 M PBS, dehydrated in ethanol (successively in 50%, 70%, 90%, 95%, and absolute ethanol), injected through Millipore filters (2 micron) and dried. The filters with samples were mounted on 12 mm Cambridge stubs using Carbon tape and sputtered with gold. Examinations of the samples were conducted using a Zeiss Supra 35-VP Field Emission SEM at 4 kV.

Transmission Electron Microscopy (TEM)

Samples for TEM were prepared as described previously (Reynolds, E. S., 1963. *J. Cell Biol.* 17, 208-212). Briefly, cells were grown and collected as described above, fixed in 2.5% glutaraldehyde, washed in 0.1 M sodium caccodylate buffer pH 7.2, and fixed with 1% osmium tetraoxide in sodium caccodylate buffer. The fixed cells were dehydrated in ethanol (successively in 70%, 95%, and absolute ethanol), treated with propylene oxide (transitional solvent), infiltrated in a mixture of propylene oxide and resin (Epon) and then embedded in pure resin mixture. This was followed by curing at 60° C. Thin sections of 50 nm were generated using an LKB 2088 ultrotom V (V=5), applied on copper slot grids and stained separately with 5% uranyl acetate and 3% lead citrate. Images were examined and photographed in a TEM Hitachi H-7100 at 75 KV.

Differential Staining of *M. marinum* Spores and Vegetative Cells

This was done as described previously (Cappuccino, J. G., Sherman, N. Microbiology, a Laboratory Manual (Benjamin Cummings, San Francisco, sixth edition, 2001)). Cells were grown as described above and harvested at different stages of growth. The cells were resuspended in water, heat-fixed on microscopic slides, heat-stained with malachite green (5% w/v in water), washed with water, and then counterstained with safranin (2.5% w/v in ethanol). After counterstaining the samples were washed with water and cells were visualized with an Olympus CH30RF200 microscope. Photographs were taken with a FujiFilm FinePix 2400Z camera.

Wet-Heat Treatment of Cells

This was performed as described previously (Chakrabarty, K. et al., *Infection and Immunity.* 74, 4430-4438 (2006). Cells grown as described above were harvested at different times during growth, resuspended in water and divided in two equal aliquots. One aliquot was exposed to heat, 65° C., for different times and then plated on 7H10 agar plates with necessary supplements (see above) and grown at 30° C. for 5 days; the other was without exposure to heat and plated as a control.

TABLE 5

| Percent survival of *M. marinum* cells after wet heat treatment | | |
|---|---|---|
| time of heat treatment(min) | % survival 1 day cells | % survival 7 day cells |
| Set1 | | |
| 0 | 100 | 100 |
| 2 | 49 | 95 |
| 5 | 17 | 63 |
| 10 | 2 | 44 |
| 15 | 0 | 39 |
| 30 | 0 | 34 |
| Set2 | | |
| 0 | 100 | 100 |
| 2 | 47 | 97 |
| 5 | 19 | 59 |
| 10 | 2 | 49 |
| 15 | 0 | 36 |
| 30 | 0 | 37 |
| Set3 | | |
| 0 | 100 | 100 |
| 2 | 46 | 90 |
| 5 | 22 | 69 |
| 10 | 3 | 40 |
| 15 | 0 | 41 |
| 30 | 0 | 28 |

| time of heat treatment(min) | % survival 1 day cells calculated average | calculated error | % survival 7 day cells calculated average | calculated error |
|---|---|---|---|---|
| 0 | 100 | 0 | 100 | 0 |
| 2 | 47.33 | 1.53 | 94 | 3.61 |
| 5 | 19.33 | 2.52 | 63.67 | 5.03 |
| 10 | 2.33 | 0.58 | 44.33 | 4.51 |
| 15 | 0 | 0 | 38.67 | 2.52 |
| 30 | 0 | 0 | 33 | 4.58 |

Extraction of Total RNA from *M. marinum*

Total RNA were extracted as described previously (Raynaud, C. et al, *Mol. Microbiol.* 45, 203 (2002)). Cells were broken in a 1 ml solution of Trizol (Invitrogen) and 0.3 ml chloroform with 0.1 mm silica beads (Q-Biogene, Lysing matrix B) using a BIO101/Savant FastPrep FP120 machine (6.5 speed, 30 sec pulse, four cycles). RNA was extracted with 300 μl of chloroform. After 10 min of centrifugation at 13000 g, the aqueous phase was re-extracted with 300 μl of chloroform and then transferred to a tube containing 250 μl of isopropanol. Total RNA was precipitated overnight at 4° C. and washed with 1 ml of a 75% ethanol before resuspension in RNase free water. Contaminating DNA was removed by digestion with RQ1 DNase (Ambion) according to the manufacturer's instructions.

RNA Dot Blot

Dot blot and probing of RNA were done as described previously (Sambrook, J., Fritsch, E. F., Maniatis, T. Molecular Cloning, a Laboratory Manual. (Cold Spring Harbor Laboratory Press, New York, third edition, 2001)). DNase-treated RNA samples prepared from day 1, 3, 5 and 7 *M. marinum* cells were denatured at 90° C. for 5 min and then spotted (10 μg in each spot) on Hybond-N+ nylon membranes (Amersham Biosciences) and air-dried. The RNA was immobilized by ultraviolet cross-linking using a Bio-Rad cross-linker, followed by hybridization with specific $^{32}$P-5'-end-labeled oligonucleotides at 42° C. The membranes were washed as described previously (Sambrook, J., Fritsch, E. F., Maniatis, T. Molecular Cloning, a Laboratory Manual (Cold Spring Harbor Laboratory Press, New York, third edition, 2001)). After probing for the mRNAs, the membranes were stripped with hot 0.01% SDS, and then re-hybridized with 5S rRNA probes and washed as above. Hybridization signals were analyzed using a Phosphor Imager (ImageQuant, Molecular Dynamics). *E. coli* K12 stationary phase RNA samples were also spotted on the same membranes and probed with the same oligonucleotides to calculate the background signals of each dot arising from unspecific binding, which were very low in the hybridization conditions. The background values were subtracted from the corresponding values of the mRNA and 5S rRNA signals. Oligonucleotide probes were labeled at their 5'-ends with γ$^{32}$P-ATP using T4 polynucleotide kinase (PNK) according to standard procedures. The nucleotide sequences of the oligonucleotide probes are listed in Table 6. To probe for *M. marinum* 5S rRNA the oligonucleotide 5'-GCTGACAGGCTTAGCTTCCG (SEQ ID NO:31) was used.

TABLE 6

| Homologs Oligo-probes used in dot blot | | |
|---|---|---|
| SpoVK | AGTCGTTCTTGGCGCCGGTTG | (SEQ ID NO:32) |
| SigF | GGAACCTTGACCGACCAAC | (SEQ ID NO:33) |
| SpoIIAB | AGTTGGTGCACGCCTCGCTG | (SEQ ID NO:34) |
| Spo0A | GTGTGTATGCGTCAGAGTC | (SEQ ID NO:35) |
| CotSA | ACGAGTGCTGGCCAGTTGAG | (SEQ ID NO:36) |
| YrbC | CAGTACGGCCACACCGTTG | (SEQ ID NO:37) |
| SpoVE | GCAAATGAGCTCATGAAAAC | (SEQ ID NO:38) |
| Soj | AGCGTTGCGCAAGCGATTCTC | (SEQ ID NO:39) |
| SpoIIIE | GTTGACGAAGCTGGACTTTC | (SEQ ID NO:40) |
| SigA | AGGCTTGCCTTCCTGGATG | (SEQ ID NO:41) |

TABLE 7

| Numerical values of dot blot signals | | | | | | | | | | |
|---|---|---|---|---|---|---|---|---|---|---|
| | SpoVK | CotSA | YrbC | SpoVE | Soj | SpoIIIE | SigF | SpoIIAB | SpoOA(TrcR) | SigA |
| Set 1 | | | | | | | | | | |
| 1 d | 1234 | 714 | 1405 | 1103 | 908 | 1315 | 732 | 1044 | 1302 | 5698 |
| 3 d | 1677 | 813 | 861 | 878 | 1234 | 1008 | 411 | 983 | 974 | 1983 |

TABLE 7-continued

| Numerical values of dot blot signals | | | | | | | | | | |
|---|---|---|---|---|---|---|---|---|---|---|
| | SpoVK | CotSA | YrbC | SpoVE | Soj | SpoIIIE | SigF | SpoIIAB | SpoOA(TrcR) | SigA |
| 5 d | 9432 | 9126 | 10023 | 9553 | 2251 | 3984 | 654 | 1706 | 8905 | 1309 |
| 7 d | 19821 | 14271 | 20017 | 20127 | 8093 | 7139 | 2037 | 1938 | 18337 | 890 |
| Set 2 | | | | | | | | | | |
| 1 d | 1098 | 615 | 1233 | 993 | 789 | 1578 | 689 | 977 | 1173 | 6605 |
| 3 d | 1541 | 798 | 792 | 803 | 1402 | 1239 | 321 | 912 | 862 | 2474 |
| 5 d | 8790 | 8773 | 9510 | 8902 | 2009 | 4037 | 614 | 1611 | 8001 | 1721 |
| 7 d | 16889 | 13043 | 18121 | 17977 | 9124 | 7802 | 1799 | 1745 | 17002 | 756 |
| Set 3 | | | | | | | | | | |
| 1 d | 1363 | 810 | 1601 | 1187 | 974 | 1147 | 823 | 1100 | 1527 | 5004 |
| 3 d | 1805 | 867 | 917 | 1014 | 1307 | 980 | 465 | 1004 | 1108 | 1879 |
| 5 d | 10017 | 1033 | 11053 | 10765 | 2511 | 3315 | 711 | 1892 | 9403 | 2043 |
| 7 d | 21680 | 15302 | 21976 | 22331 | 8672 | 6984 | 2199 | 2076 | 19319 | 1007 |
| Calculated average values: | | | | | | | | | | |
| 1 d | 1231.67 | 713 | 1413 | 1094.33 | 890.33 | 1346.67 | 748 | 1040.33 | 1334 | 5769 |
| 3 d | 1674.33 | 826 | 856.67 | 898.33 | 1314.33 | 1075.67 | 399 | 966.33 | 981.3333333 | 2112 |
| 5 d | 9413 | 6310.67 | 10195.33333 | 9740 | 2257 | 3778.67 | 659.67 | 1736.33 | 8769.666667 | 1691 |
| 7 d | 19463.33333 | 14205.33333 | 20038 | 20145 | 8629.67 | 7308.33 | 2011.666667 | 1919.67 | 18219.33333 | 884.33 |
| Calculated errors: | | | | | | | | | | |
| 1 d | 132.52 | 97.50 | 184.13 | 97.29 | 93.76 | 217.24 | 68.42 | 61.58 | 179.16 | 802.86 |
| 3 d | 132.02 | 36.29 | 62.61 | 106.96 | 84.24 | 142.14 | 72.75 | 48.21 | 123.16 | 317.78 |
| 5 d | 613.72 | 4574.000036 | 785.80 | 945.47 | 251.05 | 402.42 | 48.75 | 142.93 | 710.73 | 367.92 |
| 7 d | 2415.44 | 1130.93 | 1927.59 | 2177.06 | 516.80 | 434.50 | 201.20 | 166.26 | 1162.97 | 125.60 |

Bioinformatics

Sequence Data

Protein sequences from *Bacillus subtilis* were downloaded from the SubtiList web server, genolist.pasteur.fr/SubtiList/ (Moszer, I., Glaser P., & Danchin, A., *Microbiol.* 141, 261-268 (1995), Moszer, I., *FEBS Letters* 430, 28-36 (1998)). Sporulation-specific proteins were obtained according to the SubtiList functional category 1.8. In addition, protein sequences for sporulation related factors SigE, SigF, SigG, Spo0A (TrcR in FIG. 5) and SpoVT were also downloaded. Amino acid sequences of identified open-reading frames from *M. tuberculosis* CDC1551, *M. tuberculosis* H37Rv, and *S. coelicolor* A3 (2) were downloaded from the TIGR Comprehensive Microbial Resource (TIGR-CMR, cmr.tigr.org/tigr-scripts/CMR/CmrHomePage.cgi) Peterson, J. D., Umayam, L. A., Dickinson, T. M., Hickey E. K., & White, O., *Nucleic Acids Res.* 29, 123-125 (2001), Cole S. T. et al., *Nature* 393, 537-544 (1998), Fleischmann, R. D. Whole-Genome Comparison of *Mycobacterium tuberculosis* Clinical and Laboratory Strains. *J. Bacteriol.* 184, 5479-5490 (2002), cmr.tigr.org/tigr-scripts/CMR/CmrHomePage.cig. Amino acid sequences of the initial gene predictions for *M. marinum* were downloaded from the Sanger Institute ftp server, ftp.sanger.ac.uk/pub/pathogens/mm/. Proteins involved in *S. coelicolor* sporulation were obtained by querying the ScoDB database streptomyces.org.uk/sco/index.html) for genes with annotations containing any of the words “sporulation”, “whiA”, “whiB”, “whiD”, “whiE”, “whiG”, “whiH”, “whiI” or “whiJ” as well as genes with gene names matching “whi*” (“*” corresponding to any letter). In addition, the *S. coelicolor* gene for sigF was included.

Ortholog Search

The Washington University BLAST (WU-BLAST) package (version 2.0, release date 10 May 2005, Gish, W. [1996-2004] blast.wustl.edu) was used in a reciprocal best hit approach (RBH) (Rivera, M. C., Jain, R., Moore, J. E. & Lake, J. A. Genomic evidence for two functionally distinct gene classes. *Proc. Natl. Acad. Sci. USA* 95, 6239-6244 (1998)) to identify putative orthologues for sporulation associated *B. subtilis* and *S. coelicolor* proteins in the mycobacteria species listed above. A pair of genes was considered, a and b from genomes A and B, respectively, as putative orthologues if a search with a against B identifies b as the most significant match and a search with b against A results in a as the most significant match. The blastp program was used with default parameters and an expect cutoff at 0.001. Putative orthologues are listed in Tables 1-4. In addition, top scoring hits for the *B. subtilis* transcription factors Spo0A, SpoIIAB and SigF were used. These hits did not return the initial *B. subtilis* query protein as the top scoring hit in the RBH search and are therefore considered as weak hits. As a complement to the RBH approach, putative orthologs were identified with the reciprocal smallest distance algorithm (RSD) implemented in the software package available for download at cbi.med.harvard.edu/RSD.tar.gz (Wall, D. P., Fraser, H. B. & Hirsh, A. E. Detecting putative orthologs. Bioinformatics 19 (13), 1710-1711 (2003)). The program was run with default settings except for an E-value threshold of 0.001 and a divergence threshold of 0.5. The results are listed in Tables 1-4.

Measurement of Antibody Titers

Measurement of antibody titers mice can be performed as follows. Mice are bled four to seven days following each immunization starting after the second immunization, for a total of five bleeds. Antibody titers may be measured as spore forming peptide-binding antibody using a sandwich ELISA with plastic multi-well plates coated with a spore forming peptide.

Spore forming peptide-dependent lymphoproliferation can be measured using spleen cells harvested approximately one week following the final, sixth, immunization. Freshly harvested cells, 105 per well, may e.g. be cultured for 5 days in the presence of spore forming peptide at a concentration of 5 μM for stimulation.

Preparation of polyclonal antibodies for passive protection can be performed as follows. Twenty non-transgenic mice may be immunized with a spore forming peptide or other immunogen, optionally plus adjuvant, and then euthanized at 4-5 months. Blood may then be collected from immunized mice. Optionally, IgG is separated from other blood components. Antibody specific for the immunogen may be partially purified by affinity chromatography. An average of about 0.5-1 mg of immunogen-specific antibody may be obtained per mouse, giving a total of 5-10 mg.

Passive immunization with antibodies to a spore forming peptide can be performed as follows. Groups of 7-9 month old mice each can be injected with 0.5 mg in PBS of polyclonal anti-spore forming peptide or specific anti-spore forming peptide monoclonals as shown below. All antibody preparations should be purified to have low endotoxin levels. Monoclonals can be prepared against a fragment by injecting the fragment or longer form of a spore forming peptide into a mouse, preparing hybridomas and screening the hybridomas for an antibody that specifically binds to a desired fragment of a spore forming peptide without binding to other nonoverlapping fragments of a spore forming peptide.

Mice can be injected intraperitoneally (i.p.) as needed over a 4 month period to maintain a circulating antibody concentration measured by ELISA titer of greater than 1/1000 defined by ELISA to a CotSA or other immunogen according to this invention. Titers can be monitored as above and mice can be euthanized at the end of 4 months of injections.

The invention claimed is:

1. A method for detecting a spore related peptide from a Mycobacteria species in a sample, comprising determining the presence in said sample of a full-length spore related peptide selected from the group consisting of SEQ ID NO:2, 4, 6, 8, 10, 12, 16, 18, 20, 22, 24, 26, CotA, CotD, CotT, CotSA, SpoVK, SpoVE, Soj, SpoIIIE, and YrbC, or an immunogenic fragment thereof, from a Mycobacteria species selected from the group consisting of *Mycobacterium marinum, Mycobacterium bovis, Mycobacterium tuberculosis*, and *Mycobacterium avium* subspecies *paratuberculosis* by detecting the binding of said full-length spore related peptide, or said immunogenic fragment thereof, to a binding molecule specific for said full-length spore related peptide, or said immunogenic fragment thereof.

2. A method for inducing an immune response to a spore related peptide of Mycobacteria, comprising administering to a patient in need thereof a therapeutically active amount of a full-length spore related peptide from a Mycobacteria species selected from the group consisting of *Mycobacterium marinum, Mycobacterium bovis, Mycobacterium tuberculosis*, and *Mycobacterium avium* subspecies *paratuberculosis*, an immunogenic fragment thereof, or a binding molecule specific for said full-length spore related peptide or said immunogenic fragment thereof, wherein said full-length spore related peptide is selected from the group consisting of SEQ ID NO: 2, 4, 6, 8, 10, 12, 16, 18, 20, 22, 24, 26, CotA, CotD, CotT, CotSA, SpoVK, SpoVE, Soj, SpoIIIE, and YrbC.

3. A pharmaceutical composition comprising a full-length spore related peptide, or an immunogenic fragment thereof, from a Mycobacteria species selected from the group consisting of *Mycobacterium marinum, Mycobacterium bovis, Mycobacterium tuberculosis*, and *Mycobacterium avium* subspecies *paratuberculosis*, which is effective to induce an immunogenic response against said full-length spore related peptide from said Mycobacteria species, or an antibody thereto, in a patient, and a pharmaceutically acceptable adjuvant, wherein said full-length spore related peptide is selected from the group consisting of SEQ ID NO: 2, 4, 6, 8, 10, 12, 16, 18, 20, 22, 24, 26, CotA, CotD, CotT, CotSA, SpoVK, SpoVE, Soj, SpoIIIE, and YrbC.

4. A pharmaceutical composition according to claim 3, wherein the antibody is an antibody specific for said full-length spore related peptide.

5. A binding molecule which is capable of specifically binding to a full-length spore related peptide from a Mycobacteria species selected from the group consisting of *Mycobacterium marinum, Mycobacterium bovis, Mycobacterium tuberculosis*, and *Mycobacterium avium* subspecies *paratuberculosis*, wherein said full-length spore related peptide is selected from the group consisting of SEQ ID NO: 2, 4, 6, 8, 10, 12, 16, 18, 20, 22, 24, 26, CotA, CotD, CotT, CotSA, SpoVK, SpoVE, Soj, SpoIIIE, and YrbC.

6. A kit comprising a first binding molecule according to claim 5 and a second binding molecule capable of binding specifically to a complex between said first binding molecule and a full-length spore related peptide, or an immunogenic fragment of said full-length spore related peptide, from a Mycobacteria species selected from the group consisting of *Mycobacterium marinum, Mycobacterium bovis, Mycobacterium tuberculosis*, and *Mycobacterium avium* subspecies *paratuberculosis*, wherein said full-length spore related peptide is selected from the group consisting of SEQ ID NO: 2, 4, 6, 8, 10, 12, 16, 18, 20, 22, 24, 26, CotA, CotD, CotT, CotSA, SpoVK, SpoVE, Soj, SpoIIIE, and YrbC.

7. A kit according to claim 6, wherein at least one of said first and second binding molecules further comprise(s) a detectable moiety.

* * * * *